United States Patent
Fischer et al.

(10) Patent No.: US 10,188,108 B2
(45) Date of Patent: Jan. 29, 2019

(54) FUSED BICYCLIC HETEROCYCLE DERIVATIVES AS PESTICIDES

(71) Applicant: BAYER CROPSCIENCE AKTIENGESELLSCHAFT, Monheim am Rhein (DE)

(72) Inventors: Rüdiger Fischer, Pulheim (DE); David Wilcke, Düsseldorf (DE); Dominik Hager, Monheim (DE); Kerstin Ilg, Köln (DE); Sascha Eilmus, Leichlingen (DE); Ulrich Görgens, Ratingen (DE); Andreas Turberg, Haan (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/565,087

(22) PCT Filed: Apr. 5, 2016

(86) PCT No.: PCT/EP2016/057389
§ 371 (c)(1),
(2) Date: Oct. 6, 2017

(87) PCT Pub. No.: WO2016/162318
PCT Pub. Date: Oct. 13, 2016

(65) Prior Publication Data
US 2018/0116222 A1  May 3, 2018

(30) Foreign Application Priority Data
Apr. 8, 2015 (EP) .................................... 15162775

(51) Int. Cl.
C07D 519/00 (2006.01)
A01N 43/90 (2006.01)
C07D 471/04 (2006.01)

(52) U.S. Cl.
CPC .......... *A01N 43/90* (2013.01); *C07D 471/04* (2013.01); *C07D 519/00* (2013.01)

(58) Field of Classification Search
None
See application file for complete search history.

(56) References Cited

FOREIGN PATENT DOCUMENTS

| | | | |
|---|---|---|---|
| EP | 0052016 A1 | 11/1981 |
| EP | 0120589 A1 | 10/1984 |
| WO | 97/11075 A1 | 3/1997 |
| WO | 2009/023179 A2 | 2/2009 |
| WO | 2010/125985 A1 | 11/2010 |
| WO | 2011/041713 A2 | 4/2011 |
| WO | 2011/073316 A1 | 6/2011 |
| WO | 2012/074135 A1 | 6/2012 |
| WO | 2012/086848 A1 | 6/2012 |
| WO | 2013/018371 A1 | 2/2013 |
| WO | 2013/018928 A1 | 2/2013 |
| WO | 2013/191113 A1 | 12/2013 |
| WO | 2014/142292 A1 | 9/2014 |
| WO | 2014/148451 A1 | 9/2014 |
| WO | 2015/000715 A1 | 1/2015 |
| WO | 2016/129684 A1 | 8/2016 |
| WO | 2017/061497 A1 | 4/2017 |

OTHER PUBLICATIONS

Ji, Xiao-Ming et al., "Direct Sulfenylation of Imidazoheterocycles with Disulfides in an Iodine-Hydrogen Peroxide System", Synthesis, Feb. 17, 2015, pp. 659-671, vol. 47, No. 05, XP055193243.

Guzel, Yahya et al., Investigation of Antiulcer Activities of Imidazo [1,2-alpha]pyridinyl-2-alkylaminobenzoxazoles and 5,6,7,8-Tetahydroimidazo[1,2-alpha]pyridinyl-benzoxazoles with Electron-Topological (ET) Method, Archive der Pharmazie, Jan. 1, 2002, pp. 27-32, vol. 335, No. 1, XP055271943.

Katsura, Yousuke et al., "Studies on Antiulcer Drugs. I. Synthesis and Antiulcer Activities of Imidazo[1,2-alpha] pyridinyl-2-oxobenzoxazolidines-3-oxo-2H-1,4-benzoxazines and Related Compounds", Chemical and Pharmaceutical bulletin, Nov. 1, 1991, pp. 2937-2943, vol. 39, No. 11, XP008056522.

Hand, Elli S. et al., "Imidazo[1,2-alpha]pyridines—Novel Substitution Reactions", The Journal of Organic Chemistry, Oct. 1, 1976, pp. 3549-3556, vol. 41, No. 22, XP055272058.

Patil, Shashikant M. et al., "DMSO-POCI3: a reagent for methylthiolation of imidazo[1,2-alpha]pyridines and othero imidazo-fused heterocycles", Tetrahedron, Jul. 12, 2013, pp. 8255-8262, vol. 69, No. 38, XP028688559.

Grassy, Gerard et al., "Inhibitory effects on platelet aggregation and cyclic AMP phosphodiesterase of azaindolizine-type compounds", Chemometrics and Intelligent Laboratory Systems, Aug. 1, 1993, pp. 71-84, vol. 20, No. 1, XP026502520.

Mohan, Darapaneni Chandra et al., "Copper(I) Iodide Catalyzed Aerobic Oxidative C—N and C—S bond formations through C—H Activation: Synthesis of Functionalized Imidazo[1,2-alpha]pyridines", Asian Journal of Organic Chemistry, Mar. 11, 2014, pp. 609-613, vol. 3, No. 5, XP002757603.

(Continued)

*Primary Examiner* — Heidi Reese
(74) *Attorney, Agent, or Firm* — McBee Moore Woodward & Vanik IP, LLC

(57) ABSTRACT

The invention relates to novel compounds of the formula (I)

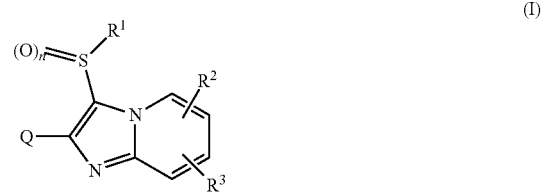

in which $R^1$, $R^2$, $R^3$, Q and n have the meanings given above, to their use as acaricides and/or insecticides for controlling animal pests and to processes and intermediates for their preparation.

14 Claims, No Drawings

(56) References Cited

OTHER PUBLICATIONS

Teulade, Jean Claude et al., "Nucleophilic aromatic substitution reaction of some 3-nitroimidazo[1,2-alpha]pyridines with thioglycolate anion in DMF", Journal of Organic Chemistry, Feb. 5, 1981, pp. 1026-1030, vol. 46, No. 5, XP002757604.
Ishida, Yasuo et al., "Studies on sulfonylureas with fused heterocycles. Part 1. Synthesis of novel herbicidal sulfonylurea compounds with an imidazo[1,2-a]pyridine moiety", Database Chemical Abstracts Service, Columbus, Ohio, XP002757605.
European Patent Application No. 15191440.5 dated Oct. 26, 2015.
European Patent Application No. 15197267.6 dated Dec. 1, 2015.
European Patent Application No. 16152384.0 dated Jan. 22, 2016.
International Search Report of International Patent Application No. PCT/EP2016/057389 dated Jun. 29, 2016.

FUSED BICYCLIC HETEROCYCLE DERIVATIVES AS PESTICIDES

CROSS-REFERENCE TO RELATED APPLICATIONS

This application is a National Stage entry of International Application No. PCT/EP2016/057389, filed 5 Apr. 2016, which claims priority to European Patent Application No. 15162775.9, filed 08 Apr. 2015.

BACKGROUND

Field of the Invention

The present invention relates to novel fused bicyclic heterocycle derivatives of the formula (I), to their use as acaricides and/or insecticides for controlling animal pests, particularly arthropods and especially insects and arachnids, and to processes and intermediates for their preparation.

Description of Related Art

Fused bicyclic heterocycle derivatives having insecticidal properties have already been described in the literature, for example in WO 2010/125985, WO 2012/074135, WO 2012/086848, WO 2013/018928, WO 2013/191113, WO 2014/142292, WO 2014/148451, WO 2015/000715, EP 15191440.5, EP 15197267.6 and EP 16152384.0.

However, the active compounds already known according to the documents cited above have some disadvantages on application, whether because they exhibit only a narrow range of application or because they do not have satisfactory insecticidal or acaricidal activity.

SUMMARY

Novel fused bicyclic heterocycle derivatives have now been found, and these have advantages over the compounds already known, examples of which are better biological or environmental properties, a wider range of application methods, better insecticidal or acaricidal activity, and also good compatibility with crop plants. The fused bicyclic heterocycle derivatives can be used in combination with further agents for improving efficacy, especially against insects that are difficult to control.

The present invention therefore provides novel compounds of the formula (I)

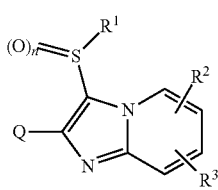

(I)

in which (configuration 1a)

$R^1$ represents ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_1$-$C_6$)-haloalkoxy-($C_1$-$C_6$)-alkyl, ($C_2$-$C_6$)-alkenyl, ($C_2$-$C_6$)-alkenyloxy-($C_1$-$C_6$)-alkyl, ($C_2$-$C_6$)-haloalkenyloxy-($C_1$-$C_6$)-alkyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_6$)-alkyl, ($C_2$-$C_6$)-haloalkynyloxy-($C_1$-$C_6$)-alkyl, ($C_2$-$C_6$)-haloalkynyl, ($C_2$-$C_6$)-cyanoalkynyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, amino, ($C_1$-$C_6$)-alkylamino, di-($C_1$-$C_6$)-alkylamino, ($C_3$-$C_8$)-cycloalkylamino, ($C_1$-$C_6$)-alkylcarbonylamino, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkylsulphinyl-($C_1$-$C_6$)-alkyl, ($C_1$-$C_6$)-haloalkylsulphinyl-($C_1$-$C_6$)-alkyl, ($C_1$-$C_6$)-alkylsulphonyl-($C_1$-$C_6$)-alkyl, ($C_1$-$C_6$)-haloalkylsulphonyl-($C_1$-$C_6$)-alkyl, ($C_1$-$C_6$)-alkoxy-($C_1$-$C_6$)-alkylthio-($C_1$-$C_6$)-alkyl, ($C_1$-$C_6$)-alkoxy-($C_1$-$C_6$)-alkylsulphinyl-($C_1$-$C_6$)-alkyl, ($C_1$-$C_6$)-alkoxy-($C_1$-$C_6$)-alkylsulphonyl-($C_1$-$C_6$)-alkyl, ($C_1$-$C_6$)-alkylcarbonyl-($C_1$-$C_6$)-alkyl, ($C_1$-$C_6$)-haloalkylcarbonyl-($C_1$-$C_6$)-alkyl, ($C_1$-$C_6$)-alkoxycarbonyl-($C_1$-$C_6$)-alkyl, ($C_1$-$C_6$)-haloalkoxycarbonyl-($C_1$-$C_6$)-alkyl, ($C_1$-$C_6$)-alkylsulphonylamino, aminosulphonyl-($C_1$-$C_6$)-alkyl, ($C_1$-$C_6$)-alkylaminosulphonyl-($C_1$-$C_6$)-alkyl, di-($C_1$-$C_6$)-alkylaminosulphonyl-($C_1$-$C_6$)-alkyl, or represents ($C_1$-$C_6$)-alkyl, ($C_1$-$C_6$)-alkoxy, ($C_2$-$C_6$)-alkenyl, ($C_2$-$C_6$)-alkynyl, ($C_3$-$C_8$)-cycloalkyl, each of which is optionally mono- or polysubstituted by identical or different substituents from the group consisting of aryl, hetaryl and heterocyclyl, where aryl, hetaryl and heterocyclyl may each optionally be mono- or polysubstituted by identical or different substituents from the group consisting of halogen, cyano, nitro, hydroxy, amino, carboxy, carbamoyl, aminosulphonyl, ($C_1$-$C_6$)-alkyl, ($C_3$-$C_6$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, ($C_1$-$C_6$)-alkylsulphimino, ($C_1$-$C_6$)-alkylsulphimino-($C_1$-$C_6$)-alkyl, ($C_1$-$C_6$)-alkylsulphimino-($C_2$-$C_6$)-alkylcarbonyl, ($C_1$-$C_6$)-alkylsulphoximino, ($C_1$-$C_6$)-alkylsulphoximino-($C_1$-$C_6$)-alkyl, ($C_1$-$C_6$)-alkylsulphoximino-($C_2$-$C_6$)-alkylcarbonyl, ($C_1$-$C_6$)-alkoxycarbonyl, ($C_1$-$C_6$)-alkylcarbonyl, ($C_3$-$C_6$)-trialkylsilyl and benzyl, or $R^1$ represents aryl, hetaryl or heterocyclyl, each of which is optionally mono- or polysubstituted by identical or different substituents from the group consisting of halogen, cyano, nitro, hydroxy, amino, carboxy, carbamoyl, ($C_1$-$C_6$)-alkyl, ($C_3$-$C_8$)-cycloalkyl, ($C_1$-$C_6$)-alkoxy, ($C_1$-$C_6$)-haloalkyl, ($C_1$-$C_6$)-haloalkoxy, ($C_1$-$C_6$)-alkylthio, ($C_1$-$C_6$)-alkylsulphinyl, ($C_1$-$C_6$)-alkylsulphonyl, ($C_1$-$C_6$)-alkylsulphimino, ($C_1$-$C_6$)-alkylsulphimino-($C_1$-$C_6$)-alkyl, ($C_1$-$C_6$)-alkylsulphimino-($C_2$-$C_6$)-alkylcarbonyl, ($C_1$-$C_6$)-alkylsulphoximino, ($C_1$-$C_6$)-alkylsulphoximino-($C_1$-$C_6$)-alkyl, ($C_1$-$C_6$)-alkylsulphoximino-($C_2$-$C_6$)-alkylcarbonyl, ($C_1$-$C_6$)-alkoxycarbonyl, ($C_1$-$C_6$)-alkylcarbonyl, ($C_3$-$C_6$)-trialkylsilyl, (=O) (only in the case of heterocyclyl) and (=O)$_2$ (only in the case of heterocyclyl), $R^2$, $R^3$ independently of one another represent hydrogen, cyano, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, hydroxycarbonyl-($C_1$-$C_6$)-alkoxy, ($C_1$-$C_6$)-alkoxycarbonyl-($C_1$-$C_6$)-alkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-haloalkynyl, ($C_2$-$C_6$)-cyanoalkynyl, ($C_1$-$C_6$)-alkoxy, ($C_1$-$C_6$)-haloalkoxy, ($C_1$-$C_6$)-cyanoalkoxy, ($C_1$-$C_6$)-alkoxycarbonyl-($C_1$-$C_6$)-alkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-haloalkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulphinyl, ($C_1$-$C_6$)-haloalkylsulphinyl, (C$_1$-C$_6$)-alkoxy-(C$_1$-C$_6$)-alkylsulphinyl, (C$_1$-C$_6$)-alkylsulphinyl-(C$_1$-C$_6$)-alkyl, (C$_1$-C$_6$)-alkylsulphonyl, (C$_1$-C$_6$)-haloalkylsulphonyl, (C$_1$-C$_6$)-alkoxy-(C$_1$-C$_6$)-alkylsulphonyl, (C$_1$-C$_6$)-alkylsulphonyl-(C$_1$-C$_6$)-alkyl, (C$_1$-C$_6$)-alkylsulphonyloxy, (C$_1$-C$_6$)-alkylcarbonyl, (C$_1$-C$_6$)-alkylthiocarbonyl, (C$_1$-C$_6$)-haloalkylcarbonyl, (C$_1$-C$_6$)-alkylcarbonyloxy, (C$_1$-C$_6$)-alkoxycarbonyl, (C$_1$-C$_6$)-haloalkoxycarbonyl, aminocarbonyl, (C$_1$-C$_6$)-alkylaminocarbonyl, (C$_1$-C$_6$)-alkylaminothiocarbonyl, di-(C$_1$-C$_6$)-alkylaminocarbonyl, di-(C$_1$-C$_6$)-alkylaminothiocarbonyl, (C$_2$-C$_6$)-alkenylaminocarbonyl, di-(C$_2$-C$_6$)-alkenylaminocarbonyl, (C$_3$-C$_8$)-cycloalkylaminocarbonyl, (C$_1$-C$_6$)-alkylsulphonylamino, (C$_1$-C$_6$)-alkylamino, di-(C$_1$-C$_6$)-alkylamino, aminosulphonyl, (C$_1$-C$_6$)-alkylaminosulphonyl, di-(C$_1$-C$_6$)-alkylaminosulphonyl, (C$_1$-C$_6$)-alkylsulphoximino, aminothiocarbonyl, (C$_1$-C$_6$)-alkylaminothiocarbonyl, di-(C$_1$-C$_6$)-alkylaminothiocarbonyl, (C$_3$-C$_8$)-cycloalkylamino, NHCO—(C$_1$-C$_6$)-alkyl ((C$_1$-C$_6$)-alkylcarbonylamino), represent aryl or hetaryl, each of which is optionally mono- or polysubstituted by identical or different substituents, where (in the case of hetaryl) optionally at least one carbonyl group may be present, and/or where suitable substituents are in each case: cyano, carboxyl, halogen, nitro, acetyl, hydroxy, amino, SCN, tri-(C$_1$-C$_6$)-alkylsilyl, (C$_3$-C$_8$)-cycloalkyl, (C$_3$-C$_8$)-cycloalkyl-(C$_3$-C$_8$)-cycloalkyl, (C$_1$-C$_6$)-alkyl-(C$_3$-C$_8$)-cycloalkyl, halo-(C$_3$-C$_8$)-cycloalkyl, (C$_1$-C$_6$)-alkyl, (C$_1$-C$_6$)-haloalkyl, (C$_1$-C$_6$)-cyanoalkyl, (C$_1$-C$_6$)-hydroxyalkyl, hydroxycarbonyl-(C$_1$-C$_6$)-alkoxy, (C$_1$-C$_6$)-alkoxycarbonyl-(C$_1$-C$_6$)-alkyl, (C$_1$-C$_6$)-alkoxy-(C$_1$-C$_6$)-alkyl, (C$_2$-C$_6$)-alkenyl, (C$_2$-C$_6$)-haloalkenyl, (C$_2$-C$_6$)-cyanoalkenyl, (C$_2$-C$_6$)-alkynyl, (C$_2$-C$_6$)-haloalkynyl, (C$_2$-C$_6$)-cyanoalkynyl, (C$_1$-C$_6$)-alkoxy, (C$_1$-C$_6$)-haloalkoxy, (C$_1$-C$_6$)-cyanoalkoxy, (C$_1$-C$_6$)-alkoxycarbonyl-(C$_1$-C$_6$)-alkoxy, (C$_1$-C$_6$)-alkoxy-(C$_1$-C$_6$)-alkoxy, (C$_1$-C$_6$)-alkylhydroxyimino, (C$_1$-C$_6$)-alkoxyimino, (C$_1$-C$_6$)-alkyl-(C$_1$-C$_6$)-alkoxyimino, (C$_1$-C$_6$)-haloalkyl-(C$_1$-C$_6$)-alkoxyimino, (C$_1$-C$_6$)-alkylthio, (C$_1$-C$_6$)-haloalkylthio, (C$_1$-C$_6$)-alkoxy-(C$_1$-C$_6$)-alkylthio, (C$_1$-C$_6$)-alkylthio-(C$_1$-C$_6$)-alkyl, (C$_1$-C$_6$)-alkylsulphinyl, (C$_1$-C$_6$)-haloalkylsulphinyl, (C$_1$-C$_6$)-alkoxy-(C$_1$-C$_6$)-alkylsulphinyl, (C$_1$-C$_6$)-alkylsulphinyl-(C$_1$-C$_6$)-alkyl, (C$_1$-C$_6$)-alkylsulphonyl, (C$_1$-C$_6$)-haloalkylsulphonyl, (C$_1$-C$_6$)-alkoxy-(C$_1$-C$_6$)-alkylsulphonyl, (C$_1$-C$_6$)-alkylsulphonyl-(C$_1$-C$_6$)-alkyl, (C$_1$-C$_6$)-alkylsulphonyloxy, (C$_1$-C$_6$)-alkylcarbonyl, (C$_1$-C$_6$)-haloalkylcarbonyl, (C$_1$-C$_6$)-alkylcarbonyloxy, (C$_1$-C$_6$)-alkoxycarbonyl, (C$_1$-C$_6$)-haloalkoxycarbonyl, aminocarbonyl, (C$_1$-C$_6$)-alkylaminocarbonyl, di-(C$_1$-C$_6$)-alkylaminocarbonyl, (C$_2$-C$_6$)-alkenylaminocarbonyl, di-(C$_2$-C$_6$)-alkenylaminocarbonyl, (C$_3$-C$_8$)-cycloalkylaminocarbonyl, (C$_1$-C$_6$)-alkylsulphonylamino, (C$_1$-C$_6$)-alkylamino, di-(C$_1$-C$_6$)-alkylamino, aminosulphonyl, (C$_1$-C$_6$)-alkylaminosulphonyl, di-(C$_1$-C$_6$)-alkylaminosulphonyl, (C$_1$-C$_6$)-alkylsulphoximino, aminothiocarbonyl, (C$_1$-C$_6$)-alkylaminothiocarbonyl, di-(C$_1$-C$_6$)-alkylaminothiocarbonyl, (C$_3$-C$_8$)-cycloalkylamino, (C$_1$-C$_6$)-alkylcarbonylamino, Q represents a partially saturated or saturated heterocyclic or heteroaromatic 8-, 9- or 10-membered fused bicyclic ring system, where optionally at least one carbonyl group may be present and/or where the ring system is optionally mono- or polysubstituted by identical or different substituents, and where the substituents independently of one another may be selected from hydrogen, cyano, halogen, nitro, acetyl, hydroxy, amino, SCN, tri-(C$_1$-C$_6$)-alkylsilyl, (C$_3$-C$_8$)-cycloalkyl, (C$_3$-C$_8$)-cycloalkyl-(C$_3$-C$_8$)-cycloalkyl, (C$_1$-C$_6$)-alkyl-(C$_3$-C$_8$)-cycloalkyl, halo-(C$_3$-C$_8$)-cycloalkyl, (C$_1$-C$_6$)-alkyl, (C$_1$-C$_6$)-haloalkyl, (C$_1$-C$_6$)-cyanoalkyl, (C$_1$-C$_6$)-hydroxyalkyl, hydroxycarbonyl-(C$_1$-C$_6$)-alkoxy, (C$_1$-C$_6$)-alkoxycarbonyl-(C$_1$-C$_6$)-alkyl, (C$_1$-C$_6$)-alkoxy-(C$_1$-C$_6$)-alkyl, (C$_2$-C$_6$)-alkenyl, (C$_2$-C$_6$)-haloalkenyl, (C$_2$-C$_6$)-cyanoalkenyl, (C$_2$-C$_6$)-alkynyl, (C$_2$-C$_6$)-alkynyloxy-(C$_1$-C$_4$)-alkyl, (C$_2$-C$_6$)-haloalkynyl, (C$_2$-C$_6$)-cyanoalkynyl, (C$_1$-C$_6$)-alkoxy, (C$_1$-C$_6$)-haloalkoxy, (C$_1$-C$_6$)-haloalkoxy-(C$_1$-C$_6$)-alkyl, (C$_2$-C$_6$)-alkenyloxy-(C$_1$-C$_6$)-alkyl, (C$_2$-C$_6$)-haloalkenyloxy-(C$_1$-C$_6$)-alkyl, (C$_1$-C$_6$)-cyanoalkoxy, (C$_1$-C$_6$)-alkoxycarbonyl-(C$_1$-C$_6$)-alkoxy, (C$_1$-C$_6$)-alkoxy-(C$_1$-C$_6$)-alkoxy, (C$_1$-C$_6$)-alkylhydroxyimino, (C$_1$-C$_6$)-alkoxyimino, (C$_1$-C$_6$)-alkyl-(C$_1$-C$_6$)-alkoxyimino, (C$_1$-C$_6$)-haloalkyl-(C$_1$-C$_6$)-alkoxyimino, (C$_1$-C$_6$)-alkylthio, (C$_1$-C$_6$)-haloalkylthio, (C$_1$-C$_6$)-alkoxy-(C$_1$-C$_6$)-alkylthio, (C$_1$-C$_6$)-alkylthio-(C$_1$-C$_6$)-alkyl, (C$_1$-C$_6$)-alkylsulphinyl, (C$_1$-C$_6$)-haloalkylsulphinyl, (C$_1$-C$_6$)-alkoxy-(C$_1$-C$_6$)-alkylsulphinyl, (C$_1$-C$_6$)-alkylsulphinyl-(C$_1$-C$_6$)-alkyl, (C$_1$-C$_6$)-alkylsulphonyl, (C$_1$-C$_6$)-haloalkylsulphonyl, (C$_1$-C$_6$)-alkoxy-(C$_1$-C$_6$)-alkylsulphonyl, (C$_1$-C$_6$)-alkylsulphonyl-(C$_1$-C$_6$)-alkyl, (C$_1$-C$_6$)-alkylsulphonyloxy, (C$_1$-C$_6$)-alkylcarbonyl, (C$_1$-C$_6$)-alkylcarbonyl-(C$_1$-C$_6$)-alkyl, (C$_1$-C$_6$)-alkylthiocarbonyl, (C$_1$-C$_6$)-haloalkylcarbonyl, (C$_1$-C$_6$)-alkylcarbonyloxy, (C$_1$-C$_6$)-alkoxycarbonyl, (C$_1$-C$_6$)-haloalkoxycarbonyl, aminocarbonyl, (C$_1$-C$_6$)-alkylaminocarbonyl, (C$_1$-C$_6$)-alkylaminothiocarbonyl, di-(C$_1$-C$_6$)-alkylaminocarbonyl, di-(C$_1$-C$_6$)-alkylaminothiocarbonyl, (C$_2$-C$_6$)-alkenylaminocarbonyl, di-(C$_2$-C$_6$)-alkenylaminocarbonyl, (C$_3$-C$_8$)-cycloalkylaminocarbonyl, (C$_1$-C$_6$)-alkylsulphonylamino, (C$_1$-C$_6$)-alkylamino, di-(C$_1$-C$_6$)-alkylamino, aminosulphonyl, (C$_1$-C$_6$)-alkylaminosulphonyl, di-(C$_1$-C$_6$)-alkylaminosulphonyl, (C$_1$-C$_6$)-alkylsulphoximino, aminothiocarbonyl, (C$_1$-C$_6$)-alkylaminothiocarbonyl, di-(C$_1$-C$_6$)-alkylaminothiocarbonyl, (C$_3$-C$_8$)-cycloalkylamino, NHCO—(C$_1$-C$_6$)-alkyl ((C$_1$-C$_6$)-alkylcarbonylamino), or where the substituents independently of one another may be selected from phenyl or a 5- or 6-membered heteroaromatic ring, where phenyl or the ring may optionally be mono- or polysubstituted by identical or different substituents from the group consisting of C$_1$-C$_6$-alkyl, C$_2$-C$_6$-alkenyl, C$_2$-C$_6$-alkynyl, C$_3$-C$_6$-cycloalkyl, C$_1$-C$_6$-haloalkyl, C$_2$-C$_6$-haloalkenyl, C$_2$-C$_6$-haloalkynyl, C$_3$-C$_6$-halocycloalkyl, halogen, CN, NO$_2$, C$_1$-C$_4$-alkoxy, C$_1$-C$_4$-haloalkoxy, n represents 0, 1 or 2.

DETAILED DESCRIPTION OF A PREFERRED EMBODIMENT

Configuration 1b

R$^1$, R$^2$, R$^3$ and n have the meanings given in Configuration 1a and

Q represents a partially saturated or saturated heterocyclic or heteroaromatic 8-, 9-, 10-, 11- or 12-membered fused bicyclic or tricyclic ring system, where optionally at least one carbonyl group may be present and/or where the ring system is optionally mono- or polysubstituted by identical or different substituents, and where the substituents independently of one another may be selected from cyano, halogen, nitro, acetyl, hydroxy, amino, SCN, tri-(C$_1$-C$_6$)-alkylsilyl, (C$_3$-C$_8$)-cycloalkyl, (C$_3$-C$_8$)-cycloalkyl-(C$_3$-C$_8$)-cycloalkyl, (C$_1$-C$_6$)-alkyl-(C$_3$-C$_8$)-cycloalkyl, halo-(C$_3$-C$_8$)-cycloalkyl, (C$_1$-C$_6$)-alkyl, (C$_1$-C$_6$)-haloalkyl, (C$_1$-C$_6$)-cyanoalkyl, (C$_1$-C$_6$)-hydroxyalkyl, hydroxycarbonyl-$(C_1-C_6)$-alkoxy, $(C_1-C_6)$-alkoxycarbonyl-$(C_1-C_6)$-alkyl, $(C_1-C_6)$-alkoxy-$(C_1-C_6)$-alkyl, $(C_2-C_6)$-alkenyl, $(C_2-C_6)$-haloalkenyl, $(C_2-C_6)$-cyanoalkenyl, $(C_2-C_6)$-alkynyl, $(C_2-C_6)$-alkynyloxy-$(C_1-C_4)$-alkyl, $(C_2-C_6)$-haloalkynyl, $(C_2-C_6)$-cyanoalkynyl, $(C_1-C_6)$-alkoxy, $(C_1-C_6)$-haloalkoxy, $(C_1-C_6)$-haloalkoxy-$(C_1-C_6)$-alkyl, $(C_2-C_6)$-alkenyloxy-$(C_1-C_6)$-alkyl, $(C_2-C_6)$-haloalkenyloxy-$(C_1-C_6)$-alkyl, $(C_1-C_6)$-cyanoalkoxy, $(C_1-C_6)$-alkoxycarbonyl-$(C_1-C_6)$-alkoxy, $(C_1-C_6)$-alkoxy-$(C_1-C_6)$-alkoxy, $(C_1-C_6)$-alkylhydroxyimino, $(C_1-C_6)$-alkoxyimino, $(C_1-C_6)$-alkyl-$(C_1-C_6)$-alkoxyimino, $(C_1-C_6)$-haloalkyl-$(C_1-C_6)$-alkoxyimino, $(C_1-C_6)$-alkylthio, $(C_1-C_6)$-haloalkylthio, $(C_1-C_6)$-alkoxy-$(C_1-C_6)$-alkylthio, $(C_1-C_6)$-alkylthio-$(C_1-C_6)$-alkyl, $(C_1-C_6)$-alkylsulphinyl, $(C_1-C_6)$-haloalkylsulphinyl, $(C_1-C_6)$-alkoxy-$(C_1-C_6)$-alkylsulphinyl, $(C_1-C_6)$-alkylsulphinyl-$(C_1-C_6)$-alkyl, $(C_1-C_6)$-alkylsulphonyl, $(C_1-C_6)$-haloalkylsulphonyl, $(C_1-C_6)$-alkoxy-$(C_1-C_6)$-alkylsulphonyl, $(C_1-C_6)$-alkylsulphonyl-$(C_1-C_6)$-alkyl, $(C_1-C_6)$-alkylsulphonyloxy, $(C_1-C_6)$-alkylcarbonyl, $(C_1-C_6)$-alkylcarbonyl-$(C_1-C_6)$-alkyl, $(C_1-C_6)$-alkylthiocarbonyl, $(C_1-C_6)$-haloalkylcarbonyl, $(C_1-C_6)$-alkylcarbonyloxy, $(C_1-C_6)$-alkoxycarbonyl, $(C_1-C_6)$-haloalkoxycarbonyl, aminocarbonyl, $(C_1-C_6)$-alkylaminocarbonyl, $(C_1-C_6)$-alkylaminothiocarbonyl, di-$(C_1-C_6)$-alkylaminocarbonyl, di-$(C_1-C_6)$-alkylaminothiocarbonyl, $(C_2-C_6)$-alkenylaminocarbonyl, di-$(C_2-C_6)$-alkenylaminocarbonyl, $(C_3-C_8)$-cycloalkylaminocarbonyl, $(C_1-C_6)$-alkylsulphonylamino, $(C_1-C_6)$-alkylamino, di-$(C_1-C_6)$-alkylamino, aminosulphonyl, $(C_1-C_6)$-alkylaminosulphonyl, di-$(C_1-C_6)$-alkylaminosulphonyl, $(C_1-C_6)$-alkylsulphoximino, aminothiocarbonyl, $(C_1-C_6)$-alkylaminothiocarbonyl, di-$(C_1-C_6)$-alkylaminothiocarbonyl, $(C_3-C_8)$-cycloalkylamino, NHCO—$(C_1-C_6)$-alkyl (($(C_1-C_6)$-alkylcarbonylamino), or where the substituents independently of one another may be selected from phenyl or a 5- or 6-membered heteroaromatic ring, where phenyl or the ring may optionally be mono- or polysubstituted by identical or different substituents from the group consisting of $C_1-C_6$-alkyl, $C_2-C_6$-alkenyl, $C_2-C_6$-alkynyl, $C_3-C_6$-cycloalkyl, $C_1-C_6$-haloalkyl, $C_2-C_6$-haloalkenyl, $C_2-C_6$-haloalkynyl, $C_3-C_6$-halocycloalkyl, halogen, CN, NO$_2$, $C_1-C_4$-alkoxy, $C_1-C_4$-haloalkoxy.

It has additionally been found that the compounds of the formula (I) have very good efficacy as pesticides, preferably as insecticides and/or acaricides, and additionally generally have very good plant compatibility, in particular with respect to crop plants.

A general definition of the compounds of the invention is provided by the formula (I). Preferred substituents or ranges of the radicals given in the formulae mentioned above and below are illustrated hereinafter:

Configuration 2a $R^1$ preferably represents $(C_1-C_4)$-alkyl, $(C_1-C_4)$-hydroxyalkyl, $(C_1-C_4)$-haloalkyl, $(C_1-C_4)$-cyanoalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_2-C_4)$-alkynyl, $(C_2-C_4)$-alkynyloxy-$(C_1-C_4)$-alkyl, $(C_2-C_4)$-haloalkynyloxy-$(C_1-C_4)$-alkyl, $(C_2-C_4)$-haloalkynyl, $(C_2-C_4)$-cyanoalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkylamino, di-$(C_1-C_4)$-alkylamino, $(C_3-C_6)$-cycloalkylamino, $(C_1-C_4)$-alkylcarbonylamino, $(C_1-C_4)$-alkylthio-$(C_1-C_4)$-alkyl, $(C_1-C_4)$-haloalkylthio-$(C_1-C_4)$-alkyl, $(C_1-C_4)$-alkylsulphinyl-$(C_1-C_4)$-alkyl, $(C_1-C_4)$-haloalkylsulphinyl-$(C_1-C_4)$-alkyl, $(C_1-C_4)$-alkylsulphonyl-$(C_1-C_4)$-alkyl, $(C_1-C_4)$-alkylcarbonyl-$(C_1-C_4)$-alkyl, $(C_1-C_4)$-haloalkylcarbonyl-$(C_1-C_4)$-alkyl, $(C_1-C_4)$-alkylsulphonylamino, or represents $(C_1-C_4)$-alkyl, $(C_1-C_4)$-alkoxy, $(C_2-C_4)$-alkenyl, $(C_2-C_4)$-alkynyl, $(C_3-C_6)$-cycloalkyl, each of which is optionally mono- or disubstituted by identical or different substituents from the group consisting of aryl, hetaryl and heterocyclyl, where aryl, hetaryl and heterocyclyl may in each case optionally be mono- or disubstituted by identical or different substituents from the group consisting of halogen, cyano, carbamoyl, aminosulphonyl, $(C_1-C_4)$-alkyl, $(C_3-C_4)$-cycloalkyl, $(C_1-C_4)$-alkoxy, $(C_1-C_4)$-haloalkyl, $(C_1-C_4)$-haloalkoxy, $(C_1-C_4)$-alkylthio, $(C_1-C_4)$-alkylsulphinyl, $(C_1-C_4)$-alkylsulphonyl, $(C_1-C_4)$-alkylsulphimino, or $R^1$ preferably represents aryl, hetaryl or heterocyclyl, each of which is optionally mono- or disubstituted by identical or different substituents from the group consisting of halogen, cyano, carbamoyl, $(C_1-C_4)$-alkyl, $(C_3-C_6)$-cycloalkyl, $(C_1-C_4)$-alkoxy, $(C_1-C_4)$-haloalkyl, $(C_1-C_4)$-haloalkoxy, $(C_1-C_4)$-alkylthio, $(C_1-C_4)$-alkylsulphinyl, $(C_1-C_4)$-alkylsulphonyl, $(C_1-C_4)$-alkylsulphimino, $(C_1-C_4)$-alkylsulphoximino, $(C_1-C_4)$-alkylcarbonyl, $(C_3-C_4)$-trialkylsilyl, (=O) (only in the case of heterocyclyl) and (=O)$_2$ (only in the case of heterocyclyl), $R^2$, $R^3$ independently of one another preferably represent hydrogen, cyano, halogen, nitro, acetyl, hydroxy, amino, SCN, tri-$(C_1-C_4)$-alkylsilyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkyl, $(C_1-C_4)$-haloalkyl, $(C_1-C_4)$-cyanoalkyl, $(C_1-C_4)$-hydroxyalkyl, $(C_1-C_4)$-alkoxy-$(C_1-C_4)$-alkyl, $(C_2-C_4)$-alkenyl, $(C_2-C_4)$-haloalkenyl, $(C_2-C_4)$-cyanoalkenyl, $(C_2-C_4)$-alkynyl, $(C_2-C_4)$-haloalkynyl, $(C_2-C_4)$-cyanoalkynyl, $(C_1-C_4)$-alkoxy, $(C_1-C_4)$-haloalkoxy, $(C_1-C_4)$-cyanoalkoxy, $(C_1-C_4)$-alkoxy-$(C_1-C_4)$-alkoxy, $(C_1-C_4)$-alkylhydroxyimino, $(C_1-C_4)$-alkoxyimino, $(C_1-C_4)$-alkyl-$(C_1-C_4)$-alkoxyimino, $(C_1-C_4)$-haloalkyl-$(C_1-C_4)$-alkoxyimino, $(C_1-C_4)$-alkylthio, $(C_1-C_4)$-haloalkylthio, $(C_1-C_4)$-alkylthio-$(C_1-C_4)$-alkyl, $(C_1-C_4)$-alkylsulphinyl, $(C_1-C_4)$-haloalkylsulphinyl, $(C_1-C_4)$-alkylsulphinyl-$(C_1-C_4)$-alkyl, $(C_1-C_4)$-alkylsulphonyl, $(C_1-C_4)$-haloalkylsulphonyl, $(C_1-C_4)$-alkylsulphonyl-$(C_1-C_4)$-alkyl, $(C_1-C_4)$-alkylsulphonyloxy, $(C_1-C_4)$-alkylcarbonyl, $(C_1-C_4)$-haloalkylcarbonyl, aminocarbonyl, aminothiocarbonyl, $(C_1-C_4)$-alkylaminocarbonyl, di-$(C_1-C_4)$-alkylaminocarbonyl, $(C_1-C_4)$-alkylsulphonylamino, $(C_1-C_4)$-alkylamino, di-$(C_1-C_4)$-alkylamino, aminosulphonyl, $(C_1-C_4)$-alkylaminosulphonyl, di-$(C_1-C_4)$-alkylaminosulphonyl, aminothiocarbonyl, NHCO—$(C_1-C_4)$-alkyl (($(C_1-C_4)$-alkylcarbonylamino), furthermore preferably represent phenyl or hetaryl, each of which is optionally mono- or disubstituted by identical or different substituents, where (in the case of hetaryl) optionally at least one carbonyl group may be present, and/or where possible substituents are in each case: cyano, halogen, nitro, acetyl, amino, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkyl, $(C_1-C_4)$-haloalkyl, $(C_1-C_4)$-cyanoalkyl, $(C_1-C_4)$-hydroxyalkyl, $(C_1-C_4)$-alkoxy-$(C_1-C_4)$-alkyl, $(C_2-C_4)$-alkenyl, $(C_2-C_4)$-haloalkenyl, $(C_2-C_4)$-cyanoalkenyl, $(C_2-C_4)$-alkynyl, $(C_2-C_4)$-haloalkynyl, $(C_2-C_4)$-cyanoalkynyl, $(C_1-C_4)$-alkoxy, $(C_1-C_4)$-haloalkoxy, $(C_1-C_4)$-cyanoalkoxy, $(C_1-C_4)$-alkoxy-$(C_1-C_4)$-alkoxy, $(C_1-C_4)$-alkylhydroxyimino, $(C_1-C_4)$- alkoxyimino, ($C_1$-$C_4$)-alkyl-($C_1$-$C_4$)-alkoxyimino, ($C_1$-$C_4$)-haloalkyl-($C_1$-$C_4$)-alkoxyimino, ($C_1$-$C_4$)-alkylthio, ($C_1$-$C_4$)-haloalkylthio, ($C_1$-$C_4$)-alkylthio-($C_1$-$C_4$)-alkyl, ($C_1$-$C_4$)-alkylsulphinyl, ($C_1$-$C_4$)-haloalkylsulphinyl, ($C_1$-$C_4$)-alkylsulphinyl-($C_1$-$C_4$)-alkyl, ($C_1$-$C_4$)-alkylsulphonyl, ($C_1$-$C_4$)-haloalkylsulphonyl, ($C_1$-$C_4$)-alkylsulphonyl-($C_1$-$C_4$)-alkyl, ($C_1$-$C_4$)-alkylsulphonyloxy, ($C_1$-$C_4$)-alkylcarbonyl, ($C_1$-$C_4$)-haloalkylcarbonyl, aminocarbonyl, ($C_1$-$C_4$)-alkylaminocarbonyl, di-($C_1$-$C_4$)-alkylaminocarbonyl, ($C_1$-$C_4$)-alkylsulphonylamino, ($C_1$-$C_4$)-alkylamino, di-($C_1$-$C_4$)-alkylamino, aminosulphonyl, ($C_1$-$C_4$)-alkylaminosulphonyl, di-($C_1$-$C_4$)-alkylaminosulphonyl, NHCO—($C_1$-$C_4$)-alkyl (($C_1$-$C_4$)-alkylcarbonylamino), Q preferably represents a heteroaromatic 8-, 9- or 10-membered fused bicyclic ring system, where the ring system is optionally mono- or polysubstituted by identical or different substituents, and where the substituents independently of one another may be selected from the group consisting of hydrogen, cyano, halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_4$)-alkyl, ($C_2$-$C_6$)-haloalkynyl, ($C_1$-$C_6$)-alkoxy, ($C_1$-$C_6$)-haloalkoxy, ($C_1$-$C_6$)-haloalkoxy-($C_1$-$C_6$)-alkyl, ($C_2$-$C_6$)-alkenyloxy-($C_1$-$C_6$)-alkyl, ($C_2$-$C_6$)-haloalkenyloxy-($C_1$-$C_6$)-alkyl, ($C_1$-$C_6$)-cyanoalkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulphinyl, ($C_1$-$C_6$)-haloalkylsulphinyl, ($C_1$-$C_6$)-alkoxy-($C_1$-$C_6$)-alkylsulphinyl, ($C_1$-$C_6$)-alkylsulphinyl-($C_1$-$C_6$)-alkyl, ($C_1$-$C_6$)-alkylsulphonyl, ($C_1$-$C_6$)-haloalkylsulphonyl, ($C_1$-$C_6$)-alkoxy-($C_1$-$C_6$)-alkylsulphonyl, ($C_1$-$C_6$)-alkylsulphonyl-($C_1$-$C_6$)-alkyl, ($C_1$-$C_6$)-alkylsulphonyloxy, ($C_1$-$C_6$)-alkylcarbonyl, ($C_1$-$C_6$)-alkylcarbonyl-($C_1$-$C_6$)-alkyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_3$-$C_8$)-cycloalkylaminocarbonyl, ($C_1$-$C_6$)-alkylsulphonylamino, ($C_1$-$C_6$)-alkylamino, di-($C_1$-$C_6$)-alkylamino, aminosulphonyl, ($C_1$-$C_6$)-alkylaminosulphonyl, di-($C_1$-$C_6$)-alkylaminosulphonyl, ($C_1$-$C_6$)-alkylsulphoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), or where the substituents independently of one another may be selected from phenyl or a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $C_1$-$C_4$-alkoxy, $C_1$-$C_4$-haloalkoxy, n preferably represents 0, 1 or 2.

Configuration 2b $R^1$, $R^2$, $R^3$ and n have the meanings given in Configuration 2a and Q preferably represents a heteroaromatic 8-, 9-, 10-, 11- or 12-membered fused bicyclic or tricyclic ring system, where the ring system is optionally mono- or polysubstituted by identical or different substituents, and where the substituents independently of one another may be selected from the group consisting of halogen, nitro, acetyl, hydroxy, amino, SCN, tri-($C_1$-$C_6$)-alkylsilyl, ($C_3$-$C_8$)-cycloalkyl, ($C_3$-$C_8$)-cycloalkyl-($C_3$-$C_8$)-cycloalkyl, ($C_1$-$C_6$)-alkyl-($C_3$-$C_8$)-cycloalkyl, halo-($C_3$-$C_8$)-cycloalkyl, ($C_1$-$C_6$)-alkyl, ($C_1$-$C_6$)-haloalkyl, ($C_1$-$C_6$)-cyanoalkyl, ($C_1$-$C_6$)-hydroxyalkyl, ($C_1$-$C_6$)-alkoxy-($C_1$-$C_6$)-alkyl, ($C_2$-$C_6$)-alkenyl, ($C_2$-$C_6$)-haloalkenyl, ($C_2$-$C_6$)-cyanoalkenyl, ($C_2$-$C_6$)-alkynyl, ($C_2$-$C_6$)-alkynyloxy-($C_1$-$C_4$)-alkyl, ($C_2$-$C_6$)-haloalkynyl, ($C_1$-$C_6$)-alkoxy, ($C_1$-$C_6$)-haloalkoxy, ($C_1$-$C_6$)-haloalkoxy-($C_1$-$C_6$)-alkyl, ($C_2$-$C_6$)-alkenyloxy-($C_1$-$C_6$)-alkyl, ($C_2$-$C_6$)-haloalkenyloxy-($C_1$-$C_6$)-alkyl, ($C_1$-$C_6$)-cyanoalkoxy, ($C_1$-$C_6$)-alkoxy-($C_1$-$C_6$)-alkoxy, ($C_1$-$C_6$)-alkylhydroxyimino, ($C_1$-$C_6$)-alkoxyimino, ($C_1$-$C_6$)-alkyl-($C_1$-$C_6$)-alkoxyimino, ($C_1$-$C_6$)-alkylthio, ($C_1$-$C_6$)-haloalkylthio, ($C_1$-$C_6$)-alkoxy-($C_1$-$C_6$)-alkylthio, ($C_1$-$C_6$)-alkylthio-($C_1$-$C_6$)-alkyl, ($C_1$-$C_6$)-alkylsulphinyl, ($C_1$-$C_6$)-haloalkylsulphinyl, ($C_1$-$C_6$)-alkoxy-($C_1$-$C_6$)-alkylsulphinyl, ($C_1$-$C_6$)-alkylsulphinyl-($C_1$-$C_6$)-alkyl, ($C_1$-$C_6$)-alkylsulphonyl, ($C_1$-$C_6$)-haloalkylsulphonyl, ($C_1$-$C_6$)-alkoxy-($C_1$-$C_6$)-alkylsulphonyl, ($C_1$-$C_6$)-alkylsulphonyl-($C_1$-$C_6$)-alkyl, ($C_1$-$C_6$)-alkylsulphonyloxy, ($C_1$-$C_6$)-alkylcarbonyl, ($C_1$-$C_6$)-alkylcarbonyl-($C_1$-$C_6$)-alkyl, ($C_1$-$C_6$)-alkylthiocarbonyl, ($C_1$-$C_6$)-haloalkylcarbonyl, ($C_1$-$C_6$)-alkylcarbonyloxy, ($C_1$-$C_6$)-alkoxycarbonyl, ($C_1$-$C_6$)-haloalkoxycarbonyl, aminocarbonyl, ($C_1$-$C_6$)-alkylaminocarbonyl, ($C_1$-$C_6$)-alkylaminothiocarbonyl, di-($C_1$-$C_6$)-alkylaminocarbonyl, di-($C_1$-$C_6$)-alkylaminothiocarbonyl, ($C_3$-$C_8$)-cycloalkylaminocarbonyl, ($C_1$-$C_6$)-alkylsulphonylamino, ($C_1$-$C_6$)-alkylamino, di-($C_1$-$C_6$)-alkylamino, aminosulphonyl, ($C_1$-$C_6$)-alkylaminosulphonyl, di-($C_1$-$C_6$)-alkylaminosulphonyl, ($C_1$-$C_6$)-alkylsulphoximino, aminothiocarbonyl, ($C_1$-$C_6$)-alkylaminothiocarbonyl, di-($C_1$-$C_6$)-alkylaminothiocarbonyl, ($C_3$-$C_8$)-cycloalkylamino, NHCO—($C_1$-$C_6$)-alkyl (($C_1$-$C_6$)-alkylcarbonylamino), or where the substituents independently of one another may be selected from phenyl or a 5- or 6-membered heteroaromatic ring, where phenyl or the ring may optionally be mono- or polysubstituted by identical or different substituents from the group consisting of $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, halogen, CN, $C_1$-$C_4$-alkoxy, $C_1$-$C_4$-haloalkoxy.

Configuration 3a $R^1$ particularly preferably represents ($C_1$-$C_4$)-alkyl, ($C_1$-$C_4$)-hydroxyalkyl, ($C_1$-$C_4$)-haloalkyl, ($C_2$-$C_4$)-alkenyl, ($C_2$-$C_4$)-haloalkenyl, ($C_2$-$C_4$)-alkynyl, ($C_2$-$C_4$)-haloalkynyl, ($C_3$-$C_6$)-cycloalkyl, ($C_1$-$C_4$)-alkylthio-($C_1$-$C_4$)-alkyl, ($C_1$-$C_4$)-alkylsulphinyl-($C_1$-$C_4$)-alkyl or ($C_1$-$C_4$)-alkylsulphonyl-($C_1$-$C_4$)-alkyl, $R^2$, $R^3$ independently of one another particularly preferably represent hydrogen, cyano, halogen, nitro, hydroxy, amino, SCN, tri-($C_1$-$C_4$)-alkylsilyl, ($C_3$-$C_6$)-cycloalkyl, ($C_3$-$C_6$)-cycloalkyl-($C_3$-$C_6$)-cycloalkyl, ($C_1$-$C_4$)-alkyl-($C_3$-$C_6$)-cycloalkyl, halo-($C_3$-$C_6$)-cycloalkyl, ($C_1$-$C_4$)-alkyl, ($C_1$-$C_4$)-haloalkyl, ($C_1$-$C_4$)-cyanoalkyl, ($C_1$-$C_4$)-alkoxy-($C_1$-$C_4$)-alkyl, ($C_2$-$C_4$)-alkenyl, ($C_2$-$C_4$)- haloalkenyl, $(C_2-C_4)$-cyanoalkenyl, $(C_2-C_4)$-alkynyl, $(C_2-C_4)$-haloalkynyl, $(C_2-C_4)$-cyanoalkynyl, $(C_1-C_4)$-alkoxy, $(C_1-C_4)$-haloalkoxy, $(C_1-C_4)$-cyanoalkoxy, $(C_1-C_4)$-alkylhydroxyimino, $(C_1-C_4)$-alkoxyimino, $(C_1-C_4)$-alkyl-$(C_1-C_4)$-alkoxyimino, $(C_1-C_4)$-alkylthio, $(C_1-C_4)$-haloalkylthio, $(C_1-C_4)$-alkylsulphinyl, $(C_1-C_4)$-haloalkylsulphinyl, $(C_1-C_4)$-alkylsulphonyl, $(C_1-C_4)$-haloalkylsulphonyl, $(C_1-C_4)$-alkylsulphonyloxy, $(C_1-C_4)$-alkylcarbonyl, $(C_1-C_4)$-haloalkylcarbonyl, aminocarbonyl, $(C_1-C_4)$-alkylaminocarbonyl, di-$(C_1-C_4)$-alkylaminocarbonyl, $(C_1-C_4)$-alkylsulphonylamino, $(C_1-C_4)$-alkylamino, di-$(C_1-C_4)$-alkylamino, aminosulphonyl, $(C_1-C_4)$-alkylaminosulphonyl, di-$(C_1-C_4)$-alkylaminosulphonyl, NHCO—$(C_1-C_4)$-alkyl ($(C_1-C_4)$-alkylcarbonylamino), furthermore particularly preferably represent phenyl or hetaryl, each of which is optionally mono- or disubstituted by identical or different substituents, where (in the case of hetaryl) optionally at least one carbonyl group may be present, and/or where possible substituents are in each case: cyano, halogen, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkyl, $(C_1-C_4)$-haloalkyl, $(C_1-C_4)$-cyanoalkyl, $(C_2-C_4)$-alkenyl, $(C_2-C_4)$-haloalkenyl, $(C_2-C_4)$-cyanoalkenyl, $(C_2-C_4)$-alkynyl, $(C_2-C_4)$-haloalkynyl, $(C_2-C_4)$-cyanoalkynyl, $(C_1-C_4)$-alkoxy, $(C_1-C_4)$-haloalkoxy, $(C_1-C_4)$-alkylhydroxyimino, $(C_1-C_4)$-alkoxyimino, $(C_1-C_4)$-alkyl-$(C_1-C_4)$-alkoxyimino, $(C_1-C_4)$-alkylthio, $(C_1-C_4)$-haloalkylthio, $(C_1-C_4)$-alkylsulphinyl, $(C_1-C_4)$-haloalkylsulphinyl, $(C_1-C_4)$-alkylsulphonyl, $(C_1-C_4)$-haloalkylsulphonyl, $(C_1-C_4)$-alkylsulphonyloxy, $(C_1-C_4)$-alkylcarbonyl, $(C_1-C_4)$-haloalkylcarbonyl, aminocarbonyl, $(C_1-C_4)$-alkylaminocarbonyl, di-$(C_1-C_4)$-alkylaminocarbonyl, $(C_1-C_4)$-alkylsulphonylamino, $(C_1-C_4)$-alkylamino, di-$(C_1-C_4)$-alkylamino, aminosulphonyl, $(C_1-C_4)$-alkylaminosulphonyl, di-$(C_1-C_4)$-alkylaminosulphonyl, NHCO—$(C_1-C_4)$-alkyl ($(C_1-C_4)$-alkylcarbonylamino), Q particularly preferably represents a heteroaromatic 9-membered fused bicyclic ring system from the group consisting of Q1 to Q19,

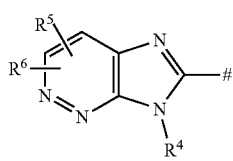
Q17

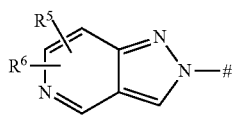
Q18

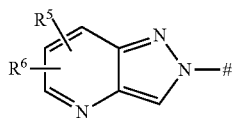
Q19

R[4] particularly preferably represents $(C_1-C_4)$-alkyl, $(C_1-C_4)$-haloalkyl, $(C_1-C_4)$-cyanoalkyl, $(C_1-C_4)$-hydroxyalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_2-C_4)$-alkynyl, $(C_2-C_4)$-alkynyloxy-$(C_1-C_4)$-alkyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkylthio-$(C_1-C_4)$-alkyl, $(C_1-C_4)$-alkylsulphinyl-$(C_1-C_4)$-alkyl, $(C_1-C_4)$-alkylsulphonyl-$(C_1-C_4)$-alkyl or $(C_1-C_4)$-alkylcarbonyl-$(C_1-C_4)$-alkyl, R[5], R[6] independently of one another particularly preferably represent hydrogen, cyano, halogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, $(C_1-C_4)$-alkoxy, $(C_1-C_4)$-haloalkoxy, $(C_1-C_4)$-alkoxyimino, $(C_1-C_4)$-alkylthio, $(C_1-C_4)$-haloalkylthio, $(C_1-C_4)$-alkylsulphinyl, $(C_1-C_4)$-haloalkylsulphinyl, $(C_1-C_4)$-alkylsulphonyl, $(C_1-C_4)$-haloalkylsulphonyl, $(C_1-C_4)$-alkylsulphonyloxy, $(C_1-C_4)$-alkylcarbonyl, $(C_1-C_4)$-haloalkylcarbonyl, aminocarbonyl, $(C_1-C_4)$-alkylaminocarbonyl, di-$(C_1-C_4)$-alkylaminocarbonyl, $(C_1-C_4)$-alkylsulphonylamino, $(C_1-C_4)$-alkylamino, di-$(C_1-C_4)$-alkylamino, aminosulphonyl, $(C_1-C_4)$-alkylaminosulphonyl or di-$(C_1-C_4)$-alkylaminosulphonyl, n particularly preferably represents 0, 1 or 2.

Configuration 3b

R[1], R[2], R[3], R[5], R[6] and n have the meanings given in Configuration 3a and Q particularly preferably represents a heteroaromatic 9-membered or 12-membered fused bicyclic or tricyclic ring system from the group consisting of Q1 to Q20,

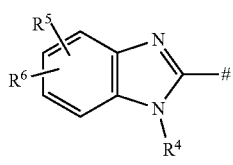
Q1

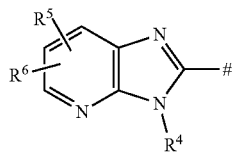
Q2

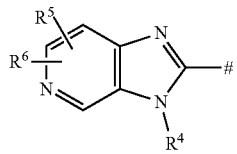
Q3

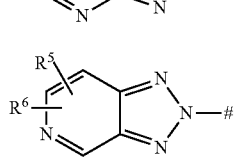
Q4

Q5

Q6

Q7

Q8

Q9

Q10

Q11

Q12

Q13

-continued

Q14
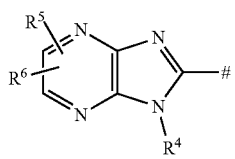

Q15
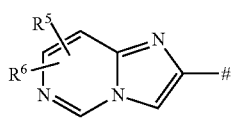

Q16
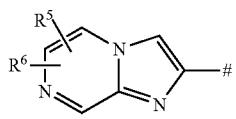

Q17
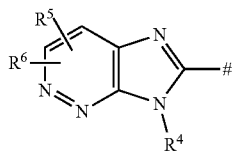

Q18
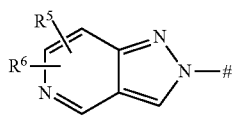

Q19
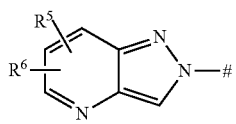

Q20
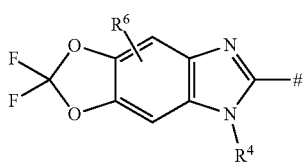

$R^4$ particularly preferably represents hydrogen, $(C_1-C_4)$-alkyl, $(C_1-C_4)$-haloalkyl, $(C_1-C_4)$-cyanoalkyl, $(C_1-C_4)$-hydroxyalkyl, $(C_1-C_4)$-alkoxy-$(C_1-C_4)$-alkyl, $(C_1-C_4)$-haloalkoxy-$(C_1-C_4)$-alkyl, $(C_2-C_4)$-alkenyl, $(C_2-C_4)$-alkenyloxy-$(C_1-C_4)$-alkyl, $(C_2-C_4)$-haloalkenyloxy-$(C_1-C_4)$-alkyl, $(C_2-C_4)$-haloalkenyl, $(C_2-C_4)$-cyanoalkenyl, $(C_2-C_4)$-alkynyl, $(C_2-C_4)$-alkynyloxy-$(C_1-C_4)$-alkyl, $(C_2-C_4)$-haloalkynyl, $(C_3-C_6)$-cycloalkyl, $(C_3-C_6)$-cycloalkyl-$(C_3-C_6)$-cycloalkyl, $(C_1-C_4)$-alkyl-$(C_3-C_6)$-cycloalkyl, halo-$(C_3-C_6)$-cycloalkyl, $(C_1-C_4)$-alkylthio-$(C_1-C_4)$-alkyl, $(C_1-C_4)$-alkylsulphinyl-$(C_1-C_4)$-alkyl, $(C_1-C_4)$-alkylsulphonyl-$(C_1-C_4)$-alkyl or $(C_1-C_4)$-alkylcarbonyl-$(C_1-C_4)$-alkyl.

Configuration 4a $R^1$ very particularly preferably represents methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^2$, $R^3$ independently of one another very particularly preferably represent hydrogen, cyano, halogen, $(C_1-C_4)$-alkyl, $(C_1-C_4)$-haloalkyl, $(C_1-C_4)$-haloalkoxy, $(C_1-C_4)$-alkylthio, $(C_1-C_4)$-alkylsulphinyl, $(C_1-C_4)$-alkylsulphonyl, $(C_1-C_4)$-haloalkylthio, $(C_1-C_4)$-haloalkylsulphinyl, $(C_1-C_4)$-haloalkylsulphonyl or NHCO—$(C_1-C_4)$-alkyl ($(C_1-C_4)$-alkylcarbonylamino), Q very particularly preferably represents a heteroaromatic 9-membered fused bicyclic ring system from the group consisting of Q2, Q3, Q5, Q6, Q8, Q9, Q10, Q11, Q12, Q13, Q15, Q16, Q17, Q18 and Q19, Q2
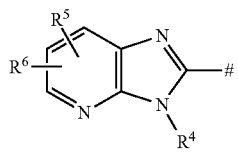

Q3
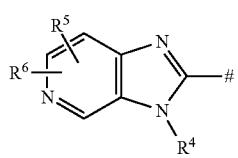

Q5
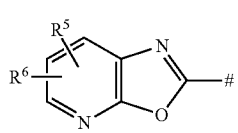

Q6
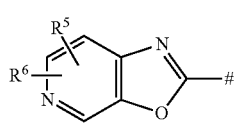

Q8
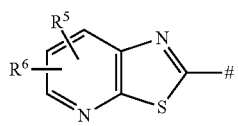

Q9
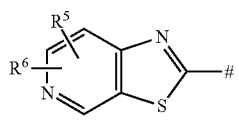

Q10
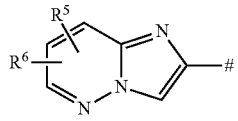

Q11
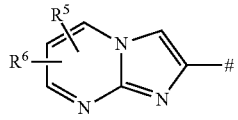

Q12
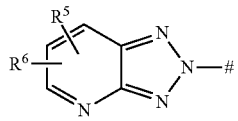

Q13
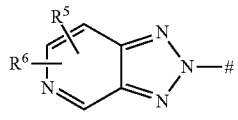

Q15
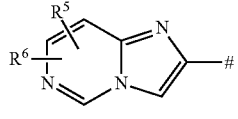

-continued

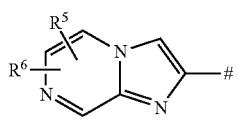 Q16

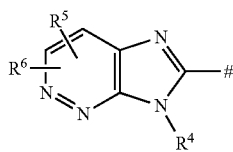 Q17

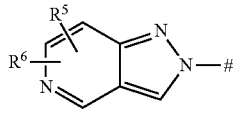 Q18

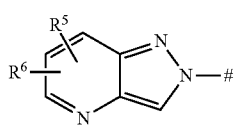 Q19

$R^4$ very particularly preferably represents $(C_1-C_4)$-alkyl or $(C_1-C_4)$-alkoxy-$(C_1-C_4)$-alkyl, $R^5$, $R^6$ independently of one another very particularly preferably represent hydrogen, cyano, halogen, $(C_1-C_4)$-alkyl, $(C_1-C_4)$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_8)$-cycloalkyl, $(C_3-C_8)$-cycloalkyl-$(C_3-C_8)$-cycloalkyl, $(C_1-C_4)$-alkyl-$(C_3-C_8)$-cycloalkyl, $(C_1-C_4)$-alkoxy, $(C_1-C_4)$-haloalkoxy, $(C_1-C_4)$-alkoxyimino, $(C_1-C_4)$-alkylthio, $(C_1-C_4)$-haloalkylthio, $(C_1-C_4)$-alkylsulphinyl, $(C_1-C_4)$-haloalkylsulphinyl, $(C_1-C_4)$-alkylsulphonyl, $(C_1-C_4)$-haloalkylsulphonyl, $(C_1-C_4)$-alkylcarbonyl, $(C_1-C_4)$-haloalkylcarbonyl, $(C_1-C_4)$-alkylaminocarbonyl, di-$(C_1-C_4)$-alkylaminocarbonyl, $(C_1-C_4)$-alkylsulphonylamino, $(C_1-C_4)$-alkylaminosulphonyl or di-$(C_1-C_4)$-alkylaminosulphonyl, n very particularly preferably represents 0, 1 or 2.

Configuration 4b $R^1$, $R^5$, $R^6$ and n have the meanings given in Configuration 4a and $R^2$, $R^3$ independently of one another very particularly preferably represent hydrogen, cyano, halogen, $(C_1-C_4)$-alkyl, $(C_1-C_4)$-alkoxy, $(C_1-C_4)$-haloalkyl, $(C_1-C_4)$-haloalkoxy, $(C_1-C_4)$-alkylthio, $(C_1-C_4)$-alkylsulphinyl, $(C_1-C_4)$-alkylsulphonyl, $(C_1-C_4)$-haloalkylthio, $(C_1-C_4)$-haloalkylsulphinyl, $(C_1-C_4)$-haloalkylsulphonyl or NHCO—$(C_1-C_4)$-alkyl ($(C_1-C_4)$-alkylcarbonylamino), Q very particularly preferably represents a heteroaromatic 9-membered or 12-membered fused bicyclic or tricyclic ring system from the group consisting of Q1, Q2, Q3, Q4, Q5, Q6, Q7, Q8, Q9, Q10, Q11, Q15, Q16, Q17 and Q20, $R^4$ very particularly preferably represents hydrogen, $(C_1-C_4)$-alkyl or $(C_1-C_4)$-alkoxy-$(C_1-C_4)$-alkyl.

Configuration 5a $R^1$ most preferably represents methyl, ethyl, n-propyl, isopropyl or cyclopropyl, $R^2$, $R^3$ independently of one another most preferably represent hydrogen, cyano, halogen, $(C_1-C_4)$-alkyl, $(C_1-C_4)$-haloalkyl, $(C_1-C_4)$-haloalkoxy, $(C_1-C_4)$-alkylthio, $(C_1-C_4)$-alkylsulphinyl, $(C_1-C_4)$-alkylsulphonyl, $(C_1-C_4)$-haloalkylthio, $(C_1-C_4)$-haloalkylsulphinyl, $(C_1-C_4)$-haloalkylsulphonyl or NHCO—$(C_1-C_4)$-alkyl ($(C_1-C_4)$-alkylcarbonylamino), Q most preferably represents a heteroaromatic 9-membered fused bicyclic ring system from the group consisting of Q2, Q3, Q10, Q15 and Q17,

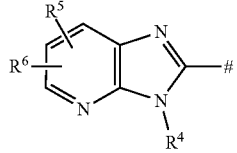 Q2

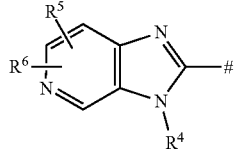 Q3

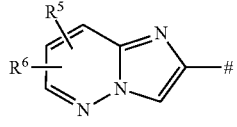 Q10

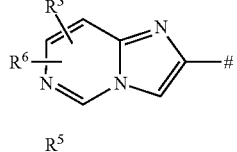 Q15

Q17

$R^4$ most preferably represents methyl, ethyl, isopropyl, methoxymethyl or methoxyethyl, (with particular emphasis methyl), $R^5$ most preferably represents hydrogen, cyano, halogen, $(C_1-C_4)$-alkyl, $(C_1-C_4)$-haloalkyl, $(C_3-C_6)$-cycloalkyl, $(C_1-C_4)$-alkoxy, $(C_1-C_4)$-haloalkoxy, $(C_1-C_4)$-alkoxyimino, $(C_1-C_4)$-alkylthio, $(C_1-C_4)$-haloalkylthio, $(C_1-C_4)$-alkylsulphinyl, $(C_1-C_4)$-haloalkylsulphinyl, $(C_1-C_4)$-alkylsulphonyl, $(C_1-C_4)$-haloalkylsulphonyl, $(C_1-C_4)$-alkylaminocarbonyl, di-$(C_1-C_4)$-alkylaminocarbonyl, $(C_1-C_4)$-alkylsulphonylamino, $(C_1-C_4)$-alkylaminosulphonyl or di-$(C_1-C_4)$-alkylaminosulphonyl, $R^6$ most preferably represents hydrogen, n most preferably represents 0, 1 or 2.

Configuration 5b $R^1$ most preferably represents methyl, ethyl, n-propyl, isopropyl or cyclopropyl, $R^2$, $R^3$ independently of one another most preferably represent hydrogen, cyano, halogen, $(C_1-C_4)$-alkyl, $(C_1-C_4)$-alkoxy, $(C_1-C_4)$-haloalkyl, $(C_1-C_4)$-haloalkoxy, $(C_1-C_4)$-alkylthio, $(C_1-C_4)$-alkylsulphinyl, $(C_1-C_4)$-alkylsulphonyl, $(C_1-C_4)$-haloalkylthio, $(C_1-C_4)$-haloalkylsulphinyl, $(C_1-C_4)$-haloalkylsulphonyl or NHCO—$(C_1-C_4)$-alkyl ($(C_1-C_4)$-alkylcarbonylamino), Q most preferably represents a 9- or 12-membered fused bicyclic or tricyclic ring system from the group consisting of Q1, Q2, Q3, Q4, Q5, Q7, Q8 and Q20, $R^4$ most preferably represents hydrogen, methyl, ethyl, isopropyl, methoxymethyl or methoxyethyl, R⁵ most preferably represents hydrogen, cyano, halogen, $(C_1-C_4)$-alkyl, $(C_1-C_4)$-haloalkyl, $(C_3-C_6)$-cycloalkyl, $(C_1-C_4)$-alkoxy, $(C_1-C_4)$-haloalkoxy, $(C_1-C_4)$-alkoxyimino, $(C_1-C_4)$-alkylthio, $(C_1-C_4)$-haloalkylthio, $(C_1-C_4)$-alkylsulphinyl, $(C_1-C_4)$-haloalkylsulphinyl, $(C_1-C_4)$-alkylsulphonyl, $(C_1-C_4)$-haloalkylsulphonyl, $(C_1-C_4)$-alkylaminocarbonyl, di-$(C_1-C_4)$-alkylaminocarbonyl, $(C_1-C_4)$-alkylsulphonylamino, $(C_1-C_4)$-alkylaminosulphonyl or di-$(C_1-C_4)$-alkylaminosulphonyl, R⁶ most preferably represents hydrogen, n most preferably represents 0, 1 or 2.

Configuration 5c

R¹ most preferably represents ethyl,

R² most preferably represents hydrogen, methyl, ethyl, n-propyl, isopropyl, n-butyl, isobutyl, tert-butyl, methoxy, ethoxy, fluorine, chlorine, bromine, iodine, fluoromethyl, difluoromethyl, trifluoromethyl, fluoroethyl, difluoroethyl, trifluoroethyl, tetrafluoroethyl, pentafluoroethyl, methylthio, ethylthio, methylsulphinyl, ethylsulphinyl, methylsulphonyl, ethylsulphonyl, trifluoromethoxy, difluorochloromethoxy, dichlorofluoromethoxy, trifluoromethylthio, trifluoromethylsulphonyl or trifluoromethylsulphinyl, R³ most preferably represents hydrogen, cyano, fluorine, chlorine, bromine, iodine, methyl, ethyl, isopropyl, fluoromethyl, difluoromethyl, trifluoromethyl, trifluoromethoxy, methylthio, ethylthio, methylsulphinyl, ethylsulphinyl, methylsulphonyl, ethylsulphonyl, trifluoromethylthio, trifluoromethylsulphinyl or trifluoromethylsulphonyl, Q most preferably represents a 9- or 12-membered fused bicyclic or tricyclic ring system from the group consisting of Q1, Q2, Q3, Q4, Q5, Q7, Q8 and Q20, R⁴ most preferably represents hydrogen or methyl, R⁵ most preferably represents cyano, fluoromethyl, difluoromethyl, trifluoromethyl, fluoroethyl, difluoroethyl, trifluoroethyl, tetrafluoroethyl, pentafluoroethyl, trifluoromethoxy, trifluoromethylthio, trifluoromethylsulphinyl or trifluoromethylsulphonyl, R⁶ most preferably represents hydrogen, n most preferably represents 0, 1 or 2.

Configuration 6a

R¹ especially represents ethyl,

R², R³ especially represent hydrogen,

Q especially represents a heteroaromatic 9-membered fused bicyclic ring system from the group consisting of Q3,

Q3

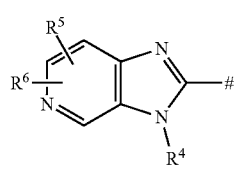

R⁴ especially represents methyl,

R⁵ especially represents trifluoromethyl,

R⁶ especially represents hydrogen, n especially represents 0 or 2.

Configuration 6b

R¹ especially represents ethyl,

R² especially represents hydrogen, methyl, methoxy, chlorine, trifluoromethyl, ethylthio (SC₂H₅) or ethylsulphonyl (SO₂C₂H₅), R³ especially represents hydrogen, Q especially represents a 9- or 12-membered fused bicyclic or tricyclic ring system from the group consisting of Q1, Q2, Q3, Q4, Q5, Q7, Q8 and Q20, R⁴ especially represents hydrogen or methyl, R⁵ especially represents trifluoromethyl, R⁶ especially represents hydrogen, n especially represents 0, 1 or 2.

Configuration 6c

R¹, R², R³ and n have the meanings given in Configuration 6b and

Q especially represents a ring from the group consisting of

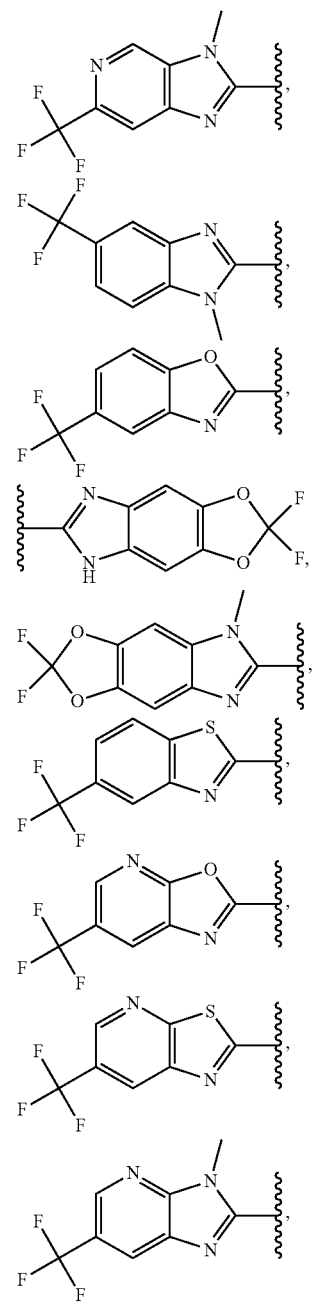

where the bond from Q to the remainder of the molecule is identified by a wavy line.

In a preferred embodiment, the invention relates to compounds of the formula (I) where Q represents Q1 and $R^1$, $R^2$, $R^3$, $R^4$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q2 and $R^1$, $R^2$, $R^3$, $R^4$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q3 and $R^1$, $R^2$, $R^3$, $R^4$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q4 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q5 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q6 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q7 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q8 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q9 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q10 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q11 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q12 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q13 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q14 and $R^1$, $R^2$, $R^3$, $R^4$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q15 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q16 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q17 and $R^1$, $R^2$, $R^3$, $R^4$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q18 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q19 and $R^1$, $R^2$, $R^3$, $R^5$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where Q represents Q20 and $R^1$, $R^2$, $R^3$, $R^6$ and n have the meanings described in configuration (3a) or configuration (3b) or configuration (4a) or configuration (4b) or configuration (5a) or configuration (5b) or configuration (5c) or configuration (6a) or configuration (6b).

In a preferred embodiment, the invention relates to compounds of the formula (I) where $R^1$ represents ethyl, $R^3$ represents hydrogen, $R^4$ represents methyl, $R^5$ represents trifluoromethyl, $R^6$ represents hydrogen and $R^2$, Q and n have the meanings described in configuration (3a) or configuration (3b) or configuration (4a) or configuration (4b) or configuration (5a) or configuration (5b) or configuration (5c) or configuration (6a) or configuration (6b).

In the preferred definitions, unless stated otherwise, halogen is selected from the group consisting of fluorine, chlorine, bromine and iodine, preferably in turn from the group consisting of fluorine, chlorine and bromine.

In the particularly preferred definitions, unless stated otherwise, halogen is selected from the group consisting of fluorine, chlorine, bromine and iodine, preferably in turn from the group consisting of fluorine, chlorine and bromine.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. From among these alkyl radicals, particular preference is given to $C_1$-$C_6$-alkyl radicals. Special preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

The term "alkoxy", either on its own or else in combination with further terms, for example haloalkoxy, is understood to mean in the present case an O-alkyl radical, where the term "alkyl" is as defined above.

Halogen-substituted radicals, for example haloalkyl, are mono- or polyhalogenated, up to the maximum number of possible substituents. In the case of polyhalogenation, the halogen atoms can be identical or different. In this case, halogen is fluorine, chlorine, bromine or iodine, especially fluorine, chlorine or bromine.

Unless stated otherwise, optionally substituted radicals may be mono- or polysubstituted, where the substituents in the case of polysubstitutions may be the same or different.

The radical definitions or elucidations given above in general terms or within areas of preference apply to the end products and correspondingly to the starting materials and intermediates. These radical definitions can be combined with one another as desired, i.e. including combinations between the respective ranges of preference.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the definitions listed above as being very particularly preferred.

Most preference according to the invention is given to using compounds of the formula (I) which contain a combination of the meanings listed above as being most preferable.

Especially used according to the invention are compounds of the formula (I) which contain a combination of the meanings listed above as being especially emphasized.

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

The compounds of the formula (I) according to the invention can be obtained by the processes shown in the following schemes:

Process A

The compounds of the formula (I) in which Q represents Q1 to Q9 or Q20 can be prepared by known methods, for example analogously to the processes described in WO2009/131237, WO2010/125985, WO2011/043404, WO2011/040629, WO2012/086848, WO2013/018928 or WO2015/000715.

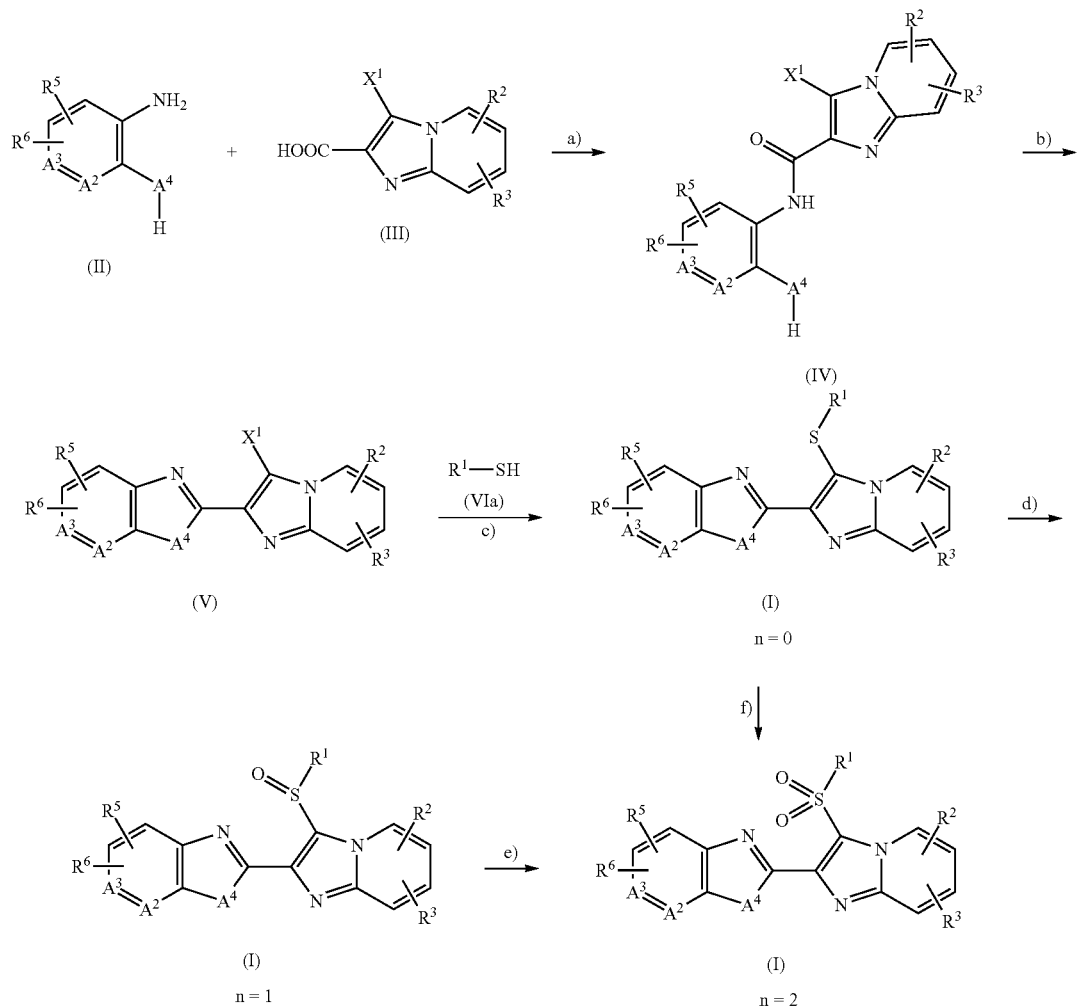

The radicals $R^1$, $R^2$, $R^3$, $R^4$, $R^5$, $R^6$ and n have the meanings described above, $A^2$ and $A^3$ represent CH or N (where $A^2$ and $A^3$ may not simultaneously represent N), $A^4$ represents O, S or N—$R^4$ and $X^1$ represents halogen.

Step a)

The compounds of the formula (IV) can be prepared in analogy to the process described in U.S. Pat. No. 5,576,335 by the reaction of compounds of the formula (II) with carboxylic acids of the formula (III) in the presence of a condensing agent or a base.

Compounds of the formula (II) are either commercially available or can be prepared by known methods, for example analogously to the processes described in US2003/69257, WO2006/65703, WO2009/131237, WO2010/125985, WO2011/043404, WO2011/040629, WO2012/086848, WO2013/018928 or WO2015/000715.

Carboxylic acids of the formula (III) are either commercially available or can be prepared by known methods, for example from 2-aminopyridine derivatives analogously to the processes described in WO2011/41713.

The reaction of the compounds of the formula (II) with carboxylic acids of the formula (III) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate.

The reaction can be carried out under reduced pressure, at atmospheric pressure or under elevated pressure and at temperatures of 0 to 180° C.; with preference, the reaction is carried out at atmospheric pressure and temperatures of 20 to 140° C.

Step b)

The compounds of the formula (V) can be prepared by condensing the compounds of the formula (IV), for example analogously to the processes described in WO2009/131237, WO2010/125985, WO2011/043404, WO2011/040629, WO2012/086848, WO2013/018928 or WO2015/000715.

The conversion to compounds of the formula (V) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be carried out in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be carried out under reduced pressure, at atmospheric pressure or under elevated pressure, and at temperatures of 0° C. to 200° C.

Step c)

The compounds of the formula (I) where n represents 0 can be prepared by reacting the compounds of the formula (V) with the compounds of the formula (VIa) in the presence of a base.

Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formula (I) where n is 0 can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given here to caesium carbonate, sodium carbonate and potassium carbonate. Further suitable bases are alkali metal hydrides, for example sodium hydride.

The reaction can be carried out under reduced pressure, at atmospheric pressure or under elevated pressure, and at temperatures of 0° C. to 200° C.

In the reaction described, $X^1$ is preferably a fluorine or chlorine atom.

Step d)

The compounds of the formula (I) where n represents 1 can be prepared by oxidizing the compounds of the formula (I) where n represents 0. The oxidation is generally carried out in a solvent selected from customary solvents which are inert under the prevailing reaction conditions. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide, meta-chloroperbenzoic acid or sodium periodate.

The reaction can be carried out under reduced pressure, at atmospheric pressure or under elevated pressure, and at temperatures of from −20° C. to 120° C.

Step e)

The compounds of the formula (I) where n represents 2 can be prepared by oxidizing the compounds of the formula (I) where n represents 1. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of from −20° C. to 120° C.

Step f)

The compounds of the formula (I) where n represents 2 can also be prepared in a one-step process by oxidizing the compounds of the formula (I) where n represents 0. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of from −20° C. to 120° C.

Process B

The compounds of the formula (I) in which Q represents Q10, Q11, Q15 or Q16 can be prepared by known methods, for example analogously to the processes described in US2009/203705, US2012/258951, WO2013/3298 or J. Med. Chem. 31, (1988) 1590-1595.

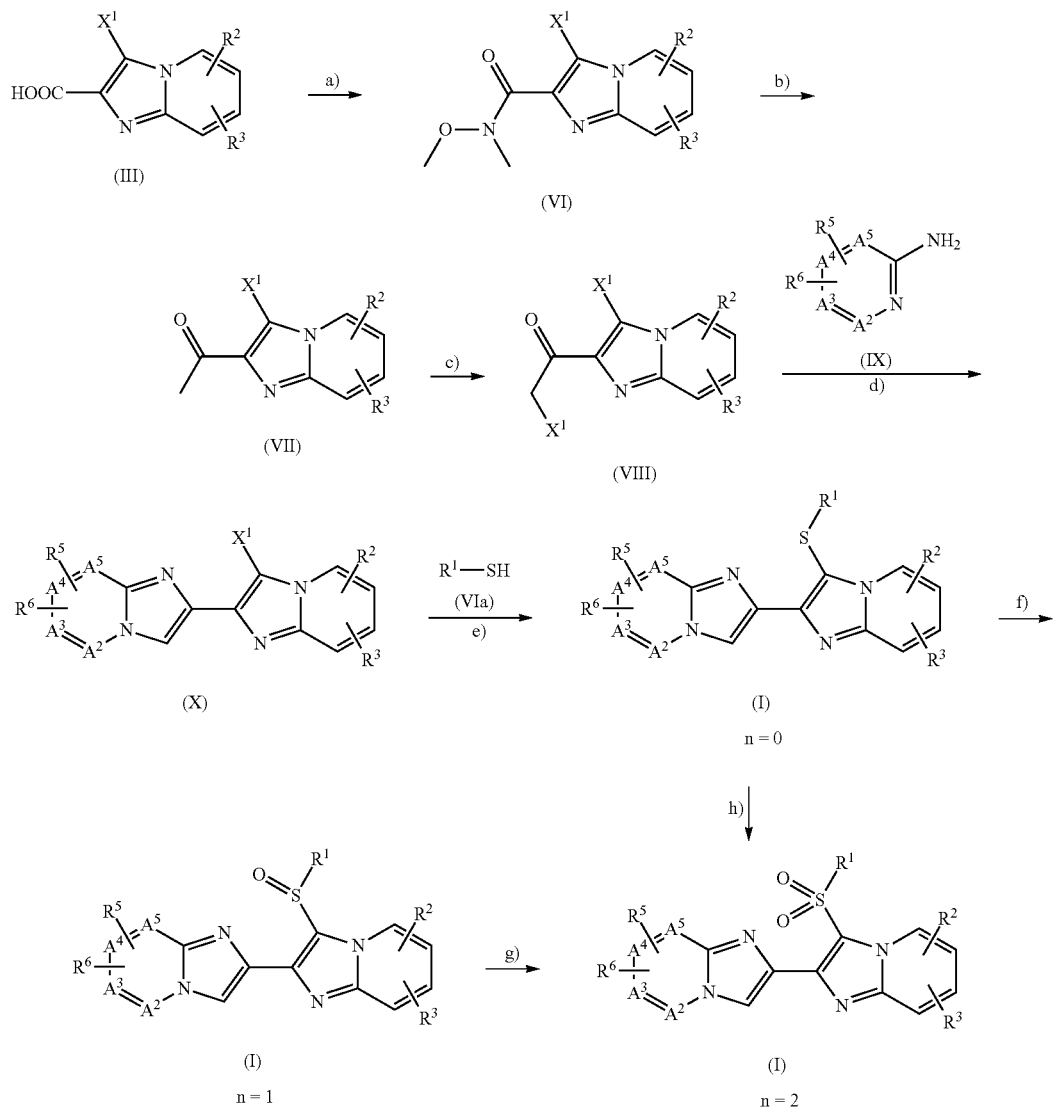

The radicals $R^1$, $R^2$, $R^3$, $R^5$, $R^6$ and n have the meanings described above. $A^2$, $A^3$, $A^4$ and $A^5$ represent CH or N (where $A^2$, $A^3$, $A^4$ and $A^5$ do not simultaneously represent N) and $X^1$ represents halogen.

Step a)

Carboxylic acids of the formula (III) are converted analogously to the process described in WO2011/75643 or EP2671582 in the presence of O,N-dimethylhydroxylamine hydrochloride into Weinreb amides of the formula (VI).

Carboxylic acids of the formula (III) are either commercially available or can be prepared by known methods, for example from 2-aminopyridine derivatives analogously to the processes described in WO2011/41713.

Step b, c)

Compounds of the formula (VI) can then be converted by known methods, for example analogously to the process described in WO2011/75643, using a Grignard reagent such as, for example, methylmagnesium bromide into ketones of the formula (VII). Compounds of the formula (VIII) are accessible by subsequent halogenation analogously, for example, to the known method described in US2012/302573.

Step d)

The compounds of the formula (X) can be prepared by cyclizing the compounds of the formula (VIII) with amines of the formula (IX). The cyclization is carried out, for example, in ethanol, acetonitrile or N,N-dimethylformamide according to known methods analogously, for example, to the processes described in WO2005/66177, WO2012/88411, WO2013/3298, US2009/203705, US2012/258951, WO2012/168733, WO2014/187762 or J. Med. Chem. 31 (1988) 1590-1595.

The compounds of the formula (IX) are commercially available.

Step e)

The compounds of the formula (I) where n represents 0 can be prepared by reacting the compounds of the formula (X) with the compounds of the formula (VIa) in the presence of a base. Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

Step f, g)

The compounds of the formula (I) where n represents 1 can be prepared by oxidizing the compounds of the formula (I) where n represents 0. The oxidation is carried out according to known methods using a suitable oxidizing agent such as, for example, hydrogen peroxide, meta-chloroperbenzoic acid or sodium periodate.

The compounds of the formula (I) where n represents 2 can be prepared by oxidizing the compounds of the formula (I) where n represents 1.

The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water. Examples of suitable oxidizing agents are hydrogen peroxide and meta-chloroperbenzoic acid.

Step h)

The compounds of the formula (I) where n represents 2 can also be prepared in a one-step process by oxidizing the compounds of the formula (I) where n represents 0. The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water. Examples of suitable oxidizing agents are hydrogen peroxide and meta-chloroperbenzoic acid.

Process C

The compounds of the formula (I) in which Q represents Q17 can be prepared by known methods, for example analogously to the processes described in WO2014/142292.

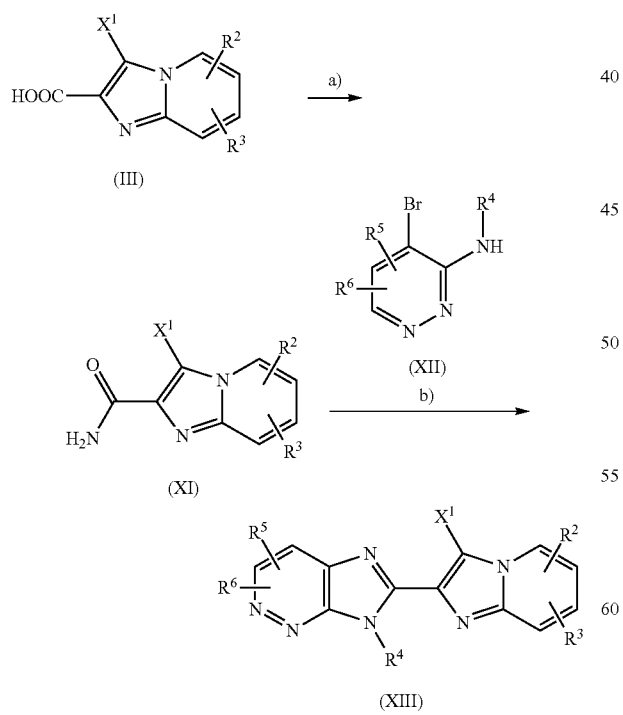

The radicals $R^2$, $R^3$, $R^4$, $R^5$ and $R^6$ have the meanings described above. $X^1$ represents halogen.

Step a)

The compounds of the formula (XI) can be prepared in analogy to the process described in U.S. Pat. No. 5,374,646 or Bioorganic and Medicinal Chemistry Letters 2003, 13, 1093-1096 by reacting compounds of the formula (III) with an ammonia source in the presence of a condensing agent.

Carboxylic acids of the formula (III) are either commercially available or can be prepared by known methods, for example from 2-aminopyridine derivatives analogously to the processes described in WO2011/41713. In most cases, the ammonia source used is ammonium hydroxide.

The reaction of the compounds of the formula (III) with the ammonia source is preferably carried out in a solvent selected from customary solvents which are inert under the prevailing reaction conditions. Preference is given to ethers such as, for example, dioxane or tetrahydrofuran.

A suitable condensing agent is, for example, carbonyldiimidazole.

The reaction can be carried out under reduced pressure, at atmospheric pressure or under elevated pressure. Preferably, the reaction is carried out at atmospheric pressure and temperatures from 20 to 70° C.

Step b)

The compounds of the formula (XIII) can be prepared in analogy to the process described in WO2014/142292 by reacting compounds of the formula (XI) with compounds of the formula (XII) in the presence of a palladium catalyst in basic media.

Compounds of the formula (XII) can be prepared, for example, analogously to the processes described in WO2014/142292. Suitable for use as palladium catalyst may be, for example, [1,1'-bis-(diphenylphosphino)ferrocene]dichloropalladium(II). Frequently, the bases used are inorganic bases such as potassium tert-butoxide.

The reaction is carried out in a solvent. Frequently, use is made of toluene.

The reaction can be carried out under reduced pressure, at atmospheric pressure or under elevated pressure. Preferably, the reaction is carried out at atmospheric pressure and temperatures from 20 to 110° C.

The further conversion of compounds of the formula (XIII) to compounds of the formula (I) is carried out analogously to process A.

Process D

The compounds of the formula (I) in which Q represents Q14 can be prepared by known methods, for example analogously to the processes described in WO2011/073149.

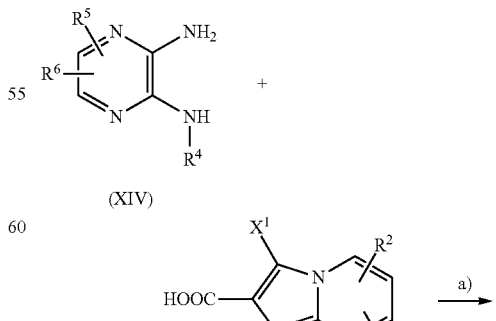

-continued

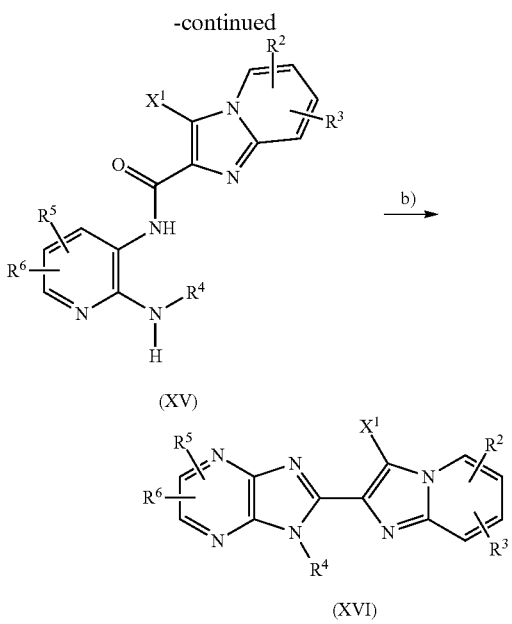

(XV)

(XVI)

The radicals $R^2$, $R^3$, $R^4$, $R^5$ and $R^6$ have the meanings described above. $X^1$ represents halogen.

Step a)

The compounds of the formula (XV) can be prepared in analogy to the process described in WO2011/073149 or U.S. Pat. No. 5,576,335 by the reaction of compounds of the formula (XIV) with a carboxylic acid of the formula (III) in the presence of a condensing agent or a base.

Compounds of the formula (XIV) are either commercially available or can be prepared by known methods, for example analogously to the processes described in WO2008/51493 or in Bioorganic and Medicinal Chemistry 2014, 22, 13, 3515-3526.

Carboxylic acids of the formula (III) are either commercially available or can be prepared by known methods, for example from 2-aminopyridine derivatives analogously to the processes described in WO2011/41713.

The reaction of the compounds of the formula (XIV) with carboxylic acids of the formula (III) can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI) or 1,3-dicyclohexylcarbodiimide.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given to sodium acetate, sodium phosphate, potassium phosphate, caesium carbonate, sodium carbonate, potassium carbonate, sodium hydrogencarbonate, potassium hydrogencarbonate.

The reaction can be carried out under reduced pressure, at atmospheric pressure or under elevated pressure and at temperatures of 0° C. to 180° C.; with preference, the reaction is carried out at atmospheric pressure and temperatures of 20 to 140° C.

Step b)

The compounds of the formula (XVI) can be prepared by condensing the compounds of the formula (XV), for example analogously to the processes described in WO2009/131237, WO2010/125985, WO2011/043404, WO2011/040629, WO2012/086848, WO2013/018928 or WO2015/000715.

The conversion to compounds of the formula (XVI) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

The reaction can be carried out in the presence of a condensing agent, an acid, a base or a chlorinating agent.

Examples of suitable condensing agents are carbodiimides such as 1-(3-dimethylaminopropyl)-3-ethylcarbodiimide hydrochloride (EDCI) or 1,3-dicyclohexylcarbodiimide; anhydrides such as acetic anhydride, trifluoroacetic anhydride; a mixture of triphenylphosphine, a base and carbon tetrachloride, or a mixture of triphenylphosphine and an azo diester, for example diethylazodicarboxylic acid.

Examples of suitable acids which can be used in the reaction described are sulphonic acids such as para-toluenesulphonic acid; carboxylic acids such as acetic acid, or polyphosphoric acids.

Examples of suitable bases are nitrogen heterocycles such as pyridine, picoline, 2,6-lutidine, 1,8-diazabicyclo[5.4.0]-7-undecene (DBU); tertiary amines such as triethylamine and N,N-diisopropylethylamine; inorganic bases such as potassium phosphate, potassium carbonate and sodium hydride.

An example of a suitable chlorinating agent is phosphorus oxychloride.

The reaction can be carried out under reduced pressure, at atmospheric pressure or under elevated pressure, and at temperatures of 0° C. to 200° C.

The further conversion of compounds of the formula (XVI) to compounds of the formula (I) is carried out analogously to process A.

Process E

The compounds of the formula (I) in which Q represents Q12, Q13, Q18 or Q19 can be prepared by known methods, for example analogously to the processes described in WO2010/091310, WO 2012/66061 or WO2013/099041.

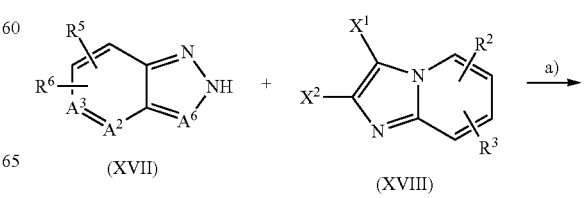

(XVII)    (XVIII)

-continued

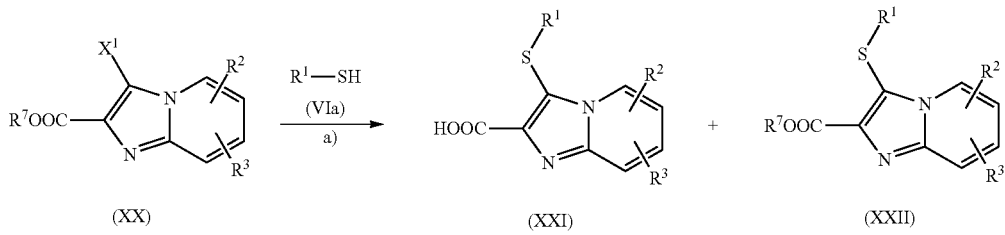

(XIX)

The radicals $R^2$, $R^3$, $R^5$ and $R^6$ have the meanings described above. $A^2$, $A^3$ and $A^6$ represent CH or N (where $A^2$ and $A^3$ may not simultaneously represent N). $X^1$ and $X^2$ represent halogen.

Step a)

The compounds of the formula (XIX) can be prepared by reacting compounds of the formula (XVII) with compounds of the formula (XVIII) under basic conditions, for example analogously to the processes described in WO2010/091310, WO 2012/66061 or WO2013/099041.

Compounds of the formula (XVII) are either commercially available or can be prepared by known methods, for example analogously to the processes described in WO2005/100353, WO 2012/66061 or in European Journal of Medicinal Chemistry 2010, 45, 2214-2222.

Compounds of the formula (XVIII) are either commercially available or can be prepared by known methods, for example analogously to the processes described in WO2013/43518, EP2168965 or in Journal of Medicinal Chemistry 2003, 46, 1449-1455.

In most cases, the bases used are inorganic bases such as sodium hydride, potassium carbonate or caesium carbonate.

In most cases, the conversion into compounds of the formula (XIX) is carried out in a solvent, preferably in a nitrile such as, for example, acetonitrile or propionitrile, or in an aprotic polar solvent such as, for example, N,N-dimethylformamide or N-methylpyrrolidone.

The reaction can be carried out under reduced pressure, at atmospheric pressure or under elevated pressure, and at temperatures of 0° C. to 200° C.

Alternatively, the conversion of compounds of the formula (XVII) with compounds of the formula (XVIII) into compounds of the formula (XIX) can also be effected by palladium-catalysed N-arylation, e.g. analogously to the processes described in Angewandte Chemie Int. Ed. 2011, 50, 8944-8947.

The further conversion of compounds of the formula (XIX) to compounds of the formula (I) is carried out analogously to process A.

Process F

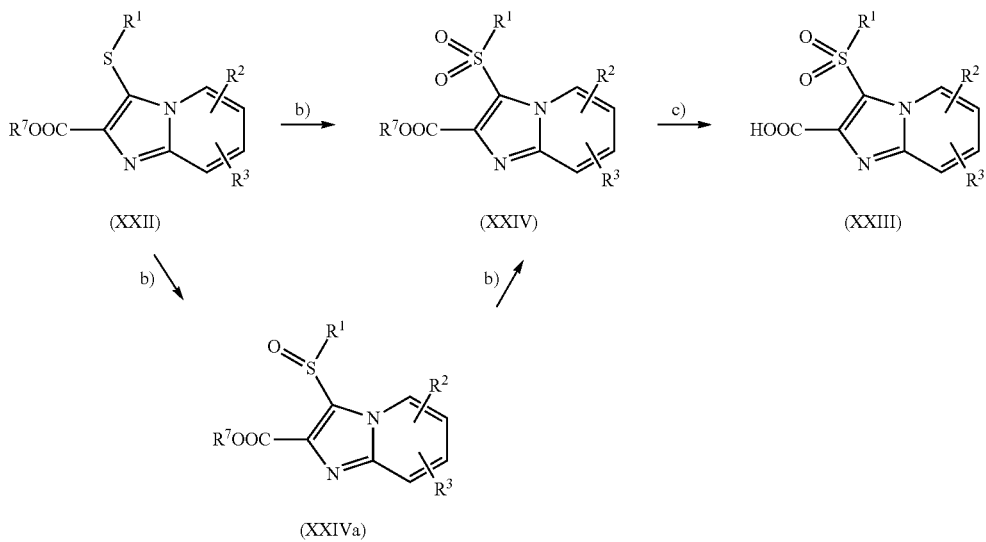

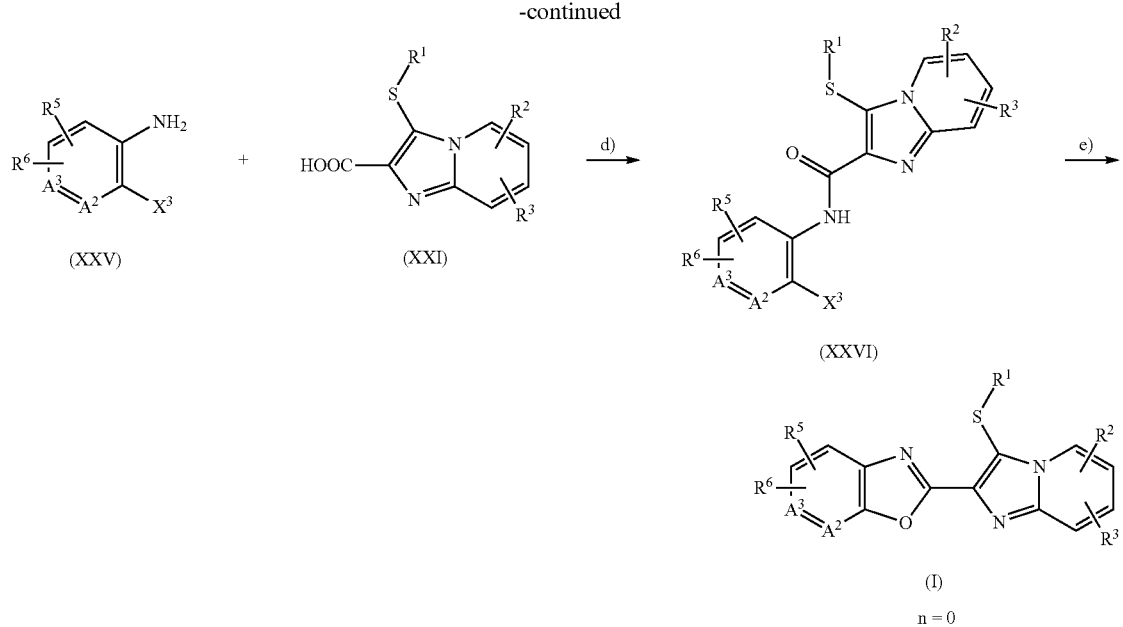

The radicals $R^1$, $R^2$, $R^3$, $R^5$, $R^6$ and n have the meanings described above, $A^2$ and $A^3$ represent CH or N, $X^1$ represents halogen, $X^3$ represents halogen and $R^7$ represents $(C_1-C_4)$-alkyl.

Step a)

The compounds of the formulae (XXI) and (XXII) can be prepared by reacting the compounds of the formula (XX) with the compounds of the formula (VIa) in the presence of a base.

The compounds of the formula (XX) are either commercially available or can be prepared by known methods, for example from 2-aminopyridine derivatives analogously to the processes described in WO2011/41713.

Mercaptan derivatives of the formula (VIa), for example methyl mercaptan, ethyl mercaptan or isopropyl mercaptan, are either commercially available or can be prepared by known methods, for example analogously to the processes described in US2006/25633, US2006/111591, U.S. Pat. No. 2,820,062, Chemical Communications, 13 (2000), 1163-1164 or Journal of the American Chemical Society, 44 (1922), p. 1329.

The conversion to compounds of the formulae (XXI) and (XXII) can be carried out neat or in a solvent; preferably, the reaction is carried out in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide.

Examples of suitable bases are inorganic bases from the group consisting of acetates, phosphates and carbonates of alkali metals or alkaline earth metals. Preference is given here to caesium carbonate, sodium carbonate and potassium carbonate. Further suitable bases are alkali metal hydrides, for example sodium hydride.

The reaction can be carried out under reduced pressure, at atmospheric pressure or under elevated pressure, and at temperatures of 0° C. to 200° C.

Step b)

The compounds of the formula (XXIV) can be prepared by oxidizing the compounds of the formula (XXII). The oxidation is generally carried out in a solvent. Preference is given to halogenated hydrocarbons, for example dichloromethane, chloroform, carbon tetrachloride, 1,2-dichloroethane or chlorobenzene; alcohols such as methanol or ethanol; formic acid, acetic acid, propionic acid or water.

Examples of suitable oxidizing agents are hydrogen peroxide and meta-chloroperbenzoic acid.

The reaction can be carried out under reduced pressure, at atmospheric pressure or under elevated pressure, and at temperatures of from −20° C. to 120° C.

The compounds of the formula (XXIVa) can be prepared analogously by oxidizing the compounds of the formula (XXII).

The compounds of the formula (XXIV) can be prepared analogously by oxidizing the compounds of the formula (XXIVa).

Step c)

The compounds of the formula (XXIII) can be prepared by hydrolysing the compounds of the formula (XXIV) in the presence of a base. The hydrolysis is generally carried out in a solvent. Preference is given to alcohols such as methanol or ethanol; water; ethers, for example diisopropyl ether, dioxane, tetrahydrofuran, 1,2-dimethoxyethane, tert-butyl methyl ether; nitriles, for example acetonitrile or propionitrile; aromatic hydrocarbons, for example toluene or xylene; aprotic polar solvents, for example N,N-dimethylformamide, N-methylpyrrolidone or dimethyl sulphoxide; or mixtures of the solvents mentioned.

Examples of suitable bases are inorganic bases from the group consisting of acetates, phosphates and carbonates of alkali metals or alkaline earth metals. Preference is given here to caesium carbonate, sodium carbonate and potassium carbonate.

The reaction can be carried out under reduced pressure, at atmospheric pressure or under elevated pressure, and at temperatures of from −20° C. to 200° C.

The further conversion of compounds of the formula (XXIII) to compounds of the formula (I) is carried out analogously to process A.

Step d)

The compounds of the formula (XXVI) can be prepared by the reaction of compounds of the formula (XXV) with carboxylic acids of the formula (XXI) in the presence of a condensing agent or a base.

The compounds of the formula (XXV) are either commercially available or can be prepared by known methods, for example analogously to the processes described in US2003/069257, US2012/0319050, WO2011/107998 or WO2010/91310.

The reaction of the compounds of the formula (XXV) with carboxylic acids of the formula (XXI) can be effected neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable condensing agents are, for example, carbodiimides such as 1-(3-dimethylaminopropyl)-3-ethylcarbodiimide hydrochloride (EDCI), 1,3-dicyclohexylcarbodiimide, thionyl chloride or oxalyl chloride.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate. Further suitable bases are alkali metal hydrides, for example sodium hydride.

The reaction can be carried out under reduced pressure, at atmospheric pressure or under elevated pressure and at temperatures of 0° C. to 180° C.; with preference, the reaction is carried out at atmospheric pressure and temperatures of 20 to 140° C.

Step e)

The compounds of the formula (I) where n represents 0 can be prepared by condensing the compounds of the formula (XXVI) in the presence of a base.

The conversion to compounds of the formula (I) where n represents 0 can be carried out neat or in a solvent, preference being given to conducting the reaction in a solvent selected from customary solvents that are inert under the prevailing reaction conditions. Preference is given to ethers, for example diisopropyl ether, dioxane, tetrahydrofuran, 1,2-dimethoxyethane, tert-butyl methyl ether; halogenated hydrocarbons, for example dichloromethane, chloroform, carbon tetrachloride, 1,2-dichloroethane or chlorobenzene; nitriles, for example acetonitrile or propionitrile; aromatic hydrocarbons, for example toluene or xylene; aprotic polar solvents, for example N,N-dimethylformamide or N-methylpyrrolidone, or nitrogen compounds, for example pyridine.

Suitable bases are inorganic bases which are typically used in such reactions. Preference is given to using bases selected by way of example from the group consisting of acetates, phosphates, carbonates and hydrogencarbonates of alkali metals or alkaline earth metals. Particular preference is given here to sodium acetate, sodium phosphate, potassium phosphate, caesium carbonate, sodium carbonate, potassium carbonate, sodium hydrogencarbonate, potassium hydrogencarbonate.

The reaction can be carried out under reduced pressure, at atmospheric pressure or under elevated pressure, and at temperatures of 0° C. to 200° C.

The invention also provides compounds of the formula (III)

in which $X^1$ represents halogen (preferably chlorine, bromine, iodine or fluorine; particularly preferably chlorine or bromine, very particularly preferably chlorine), $R^2$ and $R^3$ have the meanings given above, where $R^2$ and $R^3$ do not simultaneously represent hydrogen, where $R^2$ does not represent 8-trifluoromethyl, where $R^3$ does not represent 8-trifluoromethyl, except for the compounds below:

| X | $R^2$ | $R^3$ |
|---|---|---|
| chlorine | 6-(4-chlorophenyl) | H |
| fluorine | 7-methyl | H |
| bromine | 5-methyl | H |
| fluorine | 6-chloro | H |
| fluorine | 8-methyl | H |
| fluorine | 6-bromine | H |
| chlorine | 6-trifluoromethyl | H |

Particular emphasis is given to compounds of the formula (III) in which $X^1$ and $R^2$ have the meanings given above and $R^3$ represents hydrogen, where $R^2$ may not represent hydrogen, except for the compounds below:

| X | $R^2$ | $R^3$ |
|---|---|---|
| chlorine | 6-(4-chlorophenyl) | H |
| fluorine | 7-methyl | H |
| bromine | 5-methyl | H |
| fluorine | 6-chloro | H |
| fluorine | 8-methyl | H |
| fluorine | 6-bromine | H |
| chlorine | 6-trifluoromethyl | H |
| chlorine | 8-trifluoromethyl | H |

Very particular emphasis is given to compounds of the formula (III) in which $R^2$ represents 6-chloro (6-Cl), 7-chloro (7-Cl), 8-chloro (8-Cl), 5-trifluoromethyl (5-CF$_3$), 6-trifluoromethyl (6-CF$_3$), 7-trifluoromethyl (7-CF$_3$), 5-methyl (5-CH$_3$), 6-methyl (6-CH$_3$), 7-methyl (7-CH$_3$), 6-methoxy (6-OCH$_3$), 5-ethylthio (5-SC$_2$H$_5$), 7-ethylthio (7-SC$_2$H$_5$), 8-ethylthio (8-SC$_2$H$_5$) or 8-ethylsulphonyl (8-SO$_2$C$_2$H$_5$), $R^3$ represents hydrogen and X represents chlorine or bromine (with special emphasis chlorine).

The invention also provides compounds of the formula (V)

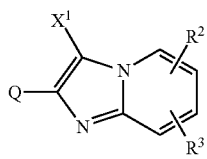

in which Q, $X^1$, $R^2$ and $R^3$ have the meanings given above.

The invention also provides compounds of the formula (XXII)

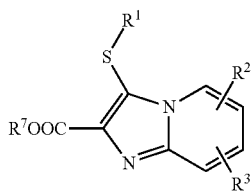

in which $R^1$, $R^2$ and $R^3$ have the meanings given above and $R^7$ represents ($C_1$-$C_4$)-alkyl (preferably methyl or ethyl, particularly preferably ethyl).

The invention also provides compounds of the formula (XXIII)

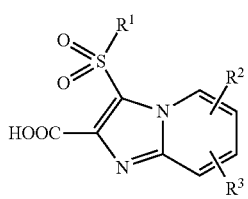

in which $R^1$, $R^2$ and $R^3$ have the meanings given above.

The invention also provides compounds of the formula (XXIV)

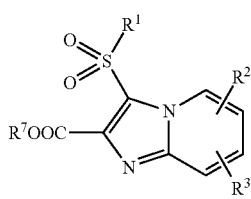

in which $R^1$, $R^2$, $R^3$ and $R^7$ have the meanings given above.

The invention also provides compounds of the formula (XXIVa)

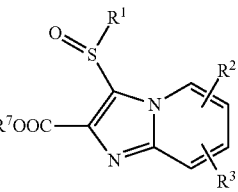

in which $R^1$, $R^2$, $R^3$ and $R^7$ have the meanings given above.

The invention also provides compounds of the formula (XXVI)

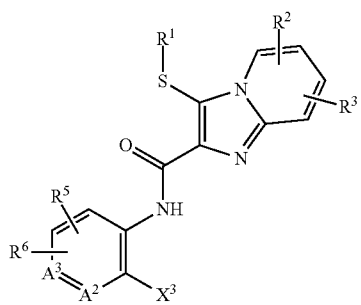

in which $X^3$ represents halogen (preferably chlorine, bromine, iodine or fluorine; particularly preferably chlorine or bromine, very particularly preferably chlorine), $A^2$ and $A^3$ represent CH or N, $R^1$, $R^2$, $R^3$, $R^5$ and $R^6$ have the meanings given above.

Methods and Uses

The invention also relates to methods for controlling animal pests, in which compounds of the formula (I) are allowed to act on animal pests and/or their habitat. The control of the animal pests is preferably carried out in agriculture and forestry, and in material protection. Preferably excluded from this are methods for the surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always comprises the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" is understood as meaning the entirety of all measures, processes and procedures whose aim it is to prevent disorders—in particular infective diseases—and to serve to keep humans, animals and/or the environment healthy and/or to maintain cleanliness. According to the invention, this includes in particular measures for cleaning, disinfecting and sterilizing, for example, textiles or solid surfaces, mainly of glass, wood, concrete, porcelain, ceramic, plastic or else of metal(s), and keeping them clean of hygiene pests and/or their faeces. Excluded according to the invention are in this respect again processes for the surgical or therapeutic treatment of the human or animal body and diagnostic processes undertaken on the human or animal body.

The term "hygiene sector" thus includes all areas, technical fields and commercial utilizations in which such hygiene measures, processes and procedures are of importance, for example hygiene in kitchens, bakeries, airports, baths, swimming pools, shopping centres, hotels, hospitals, stables, etc.

Accordingly, the term "hygiene pest" is understood as meaning one or more animal pests whose presence in the hygiene sector is problematic, in particular for health reasons. Accordingly, the main aim is to minimize or prevent hygiene pests or contact therewith in the hygiene sector. This can be effected, in particular, by using a pesticide, where the agent can be employed both prophylactically and only in the case of infestation to control the pest. It is also possible to use agents which act by avoiding or reducing contact with the pest. Hygiene pests are, for example, the organisms mentioned below.

Thus, the term "hygiene protection" includes all actions which serve to maintain and/or improve such hygiene measures, processes and procedures.

The compounds of the formula (I) can preferably be used as pesticides. They are active against normally sensitive and resistant species and also against all or some stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus* (=*Hyperodes*) spp., *Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., *Oulema oryzae, Oxycetonia jucunda, Phaedon cochleariae, Phyllophaga* spp., *Phyllophaga hel-* leri, *Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Dermaptera, for example *Anisolabis maritime, Forficula auricularia, Labidura riparia*;

from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda*;

from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes chittendeni, Dialeurodes citri, Diaphorina citri, Diaspis* spp., *Diuraphis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lopholeucaspis japonica, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigoniclla spectra, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rho-*

*palosiphum padi*, *Rhopalosiphum rufiabdominale*, *Saissetia* spp., for example *Saissetia coffeae*, *Saissetia miranda*, *Saissetia neglecta*, *Saissetia oleae*, *Scaphoideus titanus*, *Schizaphis graminum*, *Selenaspidus articulatus*, *Sitobion avenae*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., for example *Toxoptera aurantii*, *Toxoptera citricidus*, *Trialeurodes vaporariorum*, *Trioza* spp., for example *Trioza diospyri*, *Typhlocyba* spp., *Unaspis* spp., *Viteus vitifolii*, *Zygina* spp.;

from the suborder of the Heteroptera, for example *Aelia* spp., *Anasa tristis*, *Antestiopsis* spp., *Boisea* spp., *Blissus* spp., *Calocoris* spp., *Campylomma livida*, *Cavelerius* spp., *Cimex* spp., for example *Cimex adjunctus*, *Cimex hemipterus*, *Cimex lectularius*, *Cimex pilosellus*, *Collaria* spp., *Creontiades dilutus*, *Dasynus piperis*, *Dichelops furcatus*, *Diconocoris hewetti*, *Dysdercus* spp., *Euschistus* spp., for example *Euschistus heros*, *Euschistus servus*, *Euschistus tristigmus*, *Euschistus variolarius*, *Eurydema* spp., *Eurygaster* spp., *Halyomorpha halys*, *Heliopeltis* spp., *Horcias nobilellus*, *Leptocorisa* spp., *Leptocorisa varicornis*, *Leptoglossus occidentalis*, *Leptoglossus phyllopus*, *Lygocoris* spp., for example *Lygocoris pabulinus*, *Lygus* spp., for example *Lygus elisus*, *Lygus hesperus*, *Lygus lineolaris*, *Macropes excavatus*, *Megacopta cribraria*, *Miridae*, *Monalonion atratum*, *Nezara* spp., for example *Nezara viridula*, *Nysius* spp., *Oebalus* spp., *Pentomidae*, *Piesma quadrata*, *Piezodorus* spp., for example *Piezodorus guildinii*, *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the Hymenoptera, for example *Acromyrmex* spp., *Athalia* spp., for example *Athalia rosae*, *Atta* spp., *Camponotus* spp., *Dolichovespula* spp., *Diprion* spp., for example *Diprion similis*, *Hoplocampa* spp., for example *Hoplocampa cookei*, *Hoplocampa testudinea*, *Lasius* spp., *Linepithema humile*, *Monomorium pharaonis*, *Paratrechina* spp., *Paravespula* spp., *Plagiolepis* spp., *Sirex* spp., *Solenopsis invicta*, *Tapinoma* spp., *Technomyrmex albipes*, *Urocerus* spp., *Vespa* spp., for example *Vespa crabro*, *Wasmannia auropunctata*, *Xeris* spp.;

from the order of the Isopoda, for example *Armadillidium vulgare*, *Oniscus asellus*, *Porcellio scaber*;

from the order of the Isoptera, for example *Coptotermes* spp., for example *Coptotermes formosanus*, *Cornitermes cumulans*, *Cryptotermes* spp., *Incisitermes* spp., *Kalotermes* spp., *Microtermes obesi*, *Nasutitermes* spp., *Odontotermes* spp., *Porotermes* spp., *Reticulitermes* spp., for example *Reticulitermes flavipes*, *Reticulitermes hesperus*;

from the order of the Lepidoptera, for example *Achroia grisella*, *Acronicta major*, *Adoxophyes* spp., for example *Adoxophyes orana*, *Aedia leucomelas*, *Agrotis* spp., for example *Agrotis segetum*, *Agrotis ipsilon*, *Alabama* spp., for example *Alabama argillacea*, *Amyelois transitella*, *Anarsia* spp., *Anticarsia* spp., for example *Anticarsia gemmatalis*, *Argyroploce* spp., *Autographa* spp., *Barathra brassicae*, *Blastodacna atra*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., for example *Chilo plejadellus*, *Chilo suppressalis*, *Choreutis pariana*, *Choristoneura* spp., *Chrysodeixis chalcites*, *Clysia ambiguella*, *Cnaphalocerus* spp., *Cnaphalocrocis medinalis*, *Cnephasia* spp., *Conopomorpha* spp., *Conotrachelus* spp., *Copitarsia* spp., *Cydia* spp., for example *Cydia nigricana*, *Cydia pomonella*, *Dalaca noctuides*, *Diaphania* spp., *Diparopsis* spp., *Diatraea saccharalis*, *Earias* spp., *Ecdytolopha aurantium*, *Elasmopalpus lignosellus*, *Eldana saccharina*, *Ephestia* spp., for example *Ephestia elutella*, *Ephestia kuehniella*, *Epinotia* spp., *Epiphyas postvittana*, *Erannis* spp., *Erschoviella musculana*, *Etiella* spp., *Eudocima* spp., *Eulia* spp., *Eupoecilia ambiguella*, *Euproctis* spp., for example *Euproctis chrysorrhoea*, *Euxoa* spp., *Feltia* spp., *Galleria mellonella*, *Gracillaria* spp., *Grapholitha* spp., for example *Grapholita molesta*, *Grapholita prunivora*, *Hedylepta* spp., *Helicoverpa* spp., for example *Helicoverpa armigera*, *Helicoverpa zea*, *Heliothis* spp., for example *Heliothis virescens*, *Hofmannophila pseudospretella*, *Homoeosoma* spp., *Homona* spp., *Hyponomeuta padella*, *Kakivoria flavofasciata*, *Lampides* spp., *Laphygma* spp., *Laspeyresia molesta*, *Leucinodes orbonalis*, *Leucoptera* spp., for example *Leucoptera coffeella*, *Lithocolletis* spp., for example *Lithocolletis blancardella*, *Lithophane antennata*, *Lobesia* spp., for example *Lobesia botrana*, *Loxagrotis albicosta*, *Lymantria* spp., for example *Lymantria dispar*, *Lyonetia* spp., for example *Lyonetia clerkella*, *Malacosoma neustria*, *Maruca testulalis*, *Mamestra brassicae*, *Melanitis leda*, *Mocis* spp., *Monopis obviella*, *Mythimna separata*, *Nemapogon cloacellus*, *Nymphula* spp., *Oiketicus* spp., *Omphisa* spp., *Operophtera* spp., *Oria* spp., *Orthaga* spp., *Ostrinia* spp., for example *Ostrinia nubilalis*, *Oulema melanopus*, *Oulema oryzae*, *Panolis flammea*, *Parnara* spp., *Pectinophora* spp., for example *Pectinophora gossypiella*, *Perileucoptera* spp., *Phthorimaea* spp., for example *Phthorimaea operculella*, *Phyllocnistis citrella*, *Phyllonorycter* spp., for example *Phyllonorycter blancardella*, *Phyllonorycter crataegella*, *Pieris* spp., for example *Pieris rapae*, *Platynota stultana*, *Plodia interpunctella*, *Plusia* spp., *Plutella xylostella* (=*Plutella maculipennis*), *Prays* spp., *Prodenia* spp., *Protoparce* spp., *Pseudaletia* spp., for example *Pseudaletia unipuncta*, *Pseudoplusia includens*, *Pyrausta nubilalis*, *Rachiplusia nu*, *Schoenobius* spp., for example *Schoenobius bipunctifer*, *Scirpophaga* spp., for example *Scirpophaga innotata*, *Scotia segetum*, *Sesamia* spp., for example *Sesamia inferens*, *Sparganothis* spp., *Spodoptera* spp., for example *Spodoptera eradiana*, *Spodoptera exigua*, *Spodoptera frugiperda*, *Spodoptera praefica*, *Stathmopoda* spp., *Stenoma* spp., *Stomopteryx subsecivella*, *Synanthedon* spp., *Tecia solanivora*, *Thaumetopoea* spp., *Thermesia gemmatalis*, *Tinea cloacella*, *Tinea pellionella*, *Tineola bisselliella*, *Tortrix* spp., *Trichophaga tapetzella*, *Trichoplusia* spp., for example *Trichoplusia ni*, *Tryporyza incertulas*, *Tuta absoluta*, *Virachola* spp.;

from the order of the Orthoptera or Saltatoria, for example *Acheta domesticus*, *Dichroplus* spp., *Gryllotalpa* spp., for example *Gryllotalpa gryllotalpa*, *Hieroglyphus* spp., *Locusta* spp., for example *Locusta migratoria*, *Melanoplus* spp., for example *Melanoplus devastator*, *Paratlanticus ussuriensis*, *Schistocerca gregaria*;

from the order of the Phthiraptera, for example *Damalinia* spp., *Haematopinus* spp., *Linognathus* spp., *Pediculus* spp., *Phylloxera vastatrix*, *Phthirus pubis*, *Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis*, *Ctenocephalides felis*, *Pulex irritans*, *Tunga penetrans*, *Xenopsylla cheopis*; from the order of the Thysanoptera, for example *Anaphothrips obscurus*, *Baliothrips biformis*, *Chaetanaphothrips leeuweni*, *Drepanothrips reuteri*, *Enneothrips flavens*, *Frankliniella* spp., for example *Frankliniella fusca*, *Frankliniella occidentalis*, *Frankliniella schultzei*, *Frankliniella tritici*, *Frankliniella* vaccinii, Frankliniella williamsi, Haplothrips spp., Heliothrips spp., Hercinothrips femoralis, Rhipiphorothrips cruentatus, Scirtothrips spp., Taeniothrips cardamomi, Thrips spp., for example Thrips palmi, Thrips tabaci;

from the order of the Zygentoma (=Thysanura), for example Ctenolepisma spp., Lepisma saccharina, Lepismodes inquilinus, Thermobia domestica;

from the class of the Symphyla, for example Scutigerella spp., for example Scutigerella immaculata; pests from the phylum of the Mollusca, in particular from the class of the Bivalvia, for example Dreissena spp.;

and also from the class of the Gastropoda, for example Arion spp., for example Arion ater rufus, Biomphalaria spp., Bulinus spp., Deroceras spp., for example Deroceras laeve, Galba spp., Lymnaea spp., Oncomelania spp., Pomacea spp., Succinea spp.;

animal and human parasites from the phyla of the Platyhelminthes and Nematoda, for example Aelurostrongylus spp., Amidostomum spp., Ancylostoma spp., Angiostrongylus spp., Anisakis spp., Anoplocephala spp., Ascaris spp., Ascaridia spp., Baylisascaris spp., Brugia spp., Bunostomum spp., Capillaria spp., Chabertia spp., Clonorchis spp., Cooperia spp., Crenosoma spp., Cyathostoma spp., Dicrocoelium spp., Dictyocaulus spp., Diphyllobothrium spp., Dipylidium spp., Dirofilaria spp., Dracunculus spp., Echinococcus spp., Echinostoma spp., Enterobius spp., Eucoleus spp., Fasciola spp., Fascioloides spp., Fasciolopsis spp., Filaroides spp., Gongylonema spp., Gyrodactylus spp., Habronema spp., Haemonchus spp., Heligmosomoides spp., Heterakis spp., Hymenolepis spp., Hyostrongylus spp., Litomosoides spp., Loa spp., Metastrongylus spp., Metorchis spp., Mesocestoides spp., Moniezia spp., Muellerius spp., Necator spp., Nematodirus spp., Nippostrongylus spp., Oesophagostomum spp., Ollulanus spp., Onchocerca spp., Opisthorchis spp., Oslerus spp., Ostertagia spp., Oxyuris spp., Paracapillaria spp., Parafilaria spp., Paragonimus spp., Paramphistomum spp., Paranoplocephala spp., Parascaris spp., Passalurus spp., Protostrongylus spp., Schistosoma spp., Setaria spp., Spirocerca spp., Stephanofilaria spp., Stephanurus spp., Strongyloides spp., Strongylus spp., Syngamus spp., Taenia spp., Teladorsagia spp., Thelazia spp., Toxascaris spp., Toxocara spp., Trichinella spp., Trichobilharzia spp., Trichostrongylus spp., Trichuris spp., Uncinaria spp., Wuchereria spp.;

plant pests from the phylum of the Nematoda, i.e. phytoparasitic nematodes, especially Aglenchus spp., for example Aglenchus agricola, Anguina spp., for example Anguina tritici, Aphelenchoides spp., for example Aphelenchoides arachidis, Aphelenchoides fragariae, Belonolaimus spp., for example Belonolaimus gracilis, Belonolaimus longicaudatus, Belonolaimus nortoni, Bursaphelenchus spp., for example Bursaphelenchus cocophilus, Bursaphelenchus eremus, Bursaphelenchus xylophilus, Cacopaurus spp., for example Cacopaurus pestis, Criconemella spp., for example Criconemella curvata, Criconemella onoensis, Criconemella ornata, Criconemella rusium, Criconemella xenoplax (=Mesocriconema xenoplax), Criconemoides spp., for example Criconemoides ferniae, Criconemoides onoense, Criconemoides ornatum, Ditylenchus spp., for example Ditylenchus dipsaci, Dolichodorus spp., Globodera spp., for example Globodera pallida, Globodera rostochiensis, Helicotylenchus spp., for example Helicotylenchus dihystera, Hemicriconemoides spp., Hemicycliophora spp., Heterodera spp., for example Heterodera avenae, Heterodera glycines, Heterodera schachtii, Hoplolaimus spp., Longidorus spp., for example Longidorus africanus, Meloidogyne spp., for example Meloidogyne chitwoodi, Meloidogyne fallax, Meloidogyne hapla, Meloidogyne incognita, Meloinema spp., Nacobbus spp., Neotylenchus spp., Paralongidorus spp., Paraphelenchus spp., Paratrichodorus spp., for example Paratrichodorus minor, Pratylenchus spp., for example Pratylenchus penetrans, Pseudohalenchus spp., Psilenchus spp., Punctodera spp., Quinisulcius spp., Radopholus spp., for example Radopholus citrophilus, Radopholus similis, Rotylenchulus spp., Rotylenchus spp., Scutellonema spp., Subanguina spp., Trichodorus spp., for example Trichodorus obtusus, Trichodorus primitivus, Tylenchulus spp., Tylenchorhynchus spp., for example Tylenchorhynchus annulatus, Tylenchulus spp., for example Tylenchulus semipenetrans, Xiphinema spp., for example Xiphinema index.

In addition, it is possible to control, from the sub-kingdom of the Protozoa, the order of the Coccidia, for example Eimeria spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, corn cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulfan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds having unknown or nonspecific mechanisms of action, for example alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, for example *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.
(13) Oxidative phosphorylation decouplers that interrupt the H proton gradient, for example chlorfenapyr, DNOC and sulfluramid.
(14) Nicotinergic acetylcholine receptor antagonists, for example bensultap, cartap hydrochloride, thiocyclam, and thiosultap-sodium.
(15) Chitin biosynthesis inhibitors, type 0, for example bistrifluron, chlorfluazuron, diflubenzuron, flucycloxuron, flufenoxuron, hexaflumuron, lufenuron, novaluron, noviflumuron, teflubenzuron and triflumuron.
(16) Chitin biosynthesis inhibitors, type 1, for example buprofezin.
(17) Moulting inhibitors (especially for Diptera, i.e. dipterans), for example cyromazine.
(18) Ecdysone receptor agonists, for example chromafenozide, halofenozide, methoxyfenozide and tebufenozide.
(19) Octopaminergic agonists, for example amitraz.
(20) Complex-III electron transport inhibitors, for example hydramethylnon or acequinocyl or fluacrypyrim.
(21) Complex-I electron transport inhibitors, for example METI acaricides, e.g. fenazaquin, fenpyroximate, pyrimidifen, pyridaben, tebufenpyrad and tolfenpyrad or rotenone (Derris).
(22) Voltage-gated sodium channel blockers, for example indoxacarb or metaflumizone.
(23) Inhibitors of acetyl-CoA carboxylase, for example tetronic and tetramic acid derivatives, e.g. spirodiclofen, spiromesifen and spirotetramat.
(24) Complex-IV electron transport inhibitors, for example phosphines, e.g. aluminium phosphide, calcium phosphide, phosphine and zinc phosphide or cyanide.
(25) Complex-II electron transport inhibitors, for example cyenopyrafen and cyflumetofen.
(28) Ryanodine receptor effectors, for example diamides, e.g. chlorantraniliprole, cyantraniliprole and flubendiamide.

Further active compounds having an unknown or unclear mechanism of action, for example afidopyropen, afoxolaner, azadirachtin, benclothiaz, benzoximate, bifenazate, broflanilide, bromopropylate, chinomethionat, cryolite, cyclaniliprole, cycloaprid, cyhalodiamide, dicloromezotiaz, dicofol, diflovidazin, flometoquin, fluazaindolizine, fluensulphone, flufenerim, flufenoxystrobin, flufiprole, fluhexafon, fluopyram, fluralaner, fluxametamide, fufenozide, guadipyr, heptafluthrin, imidaclothiz, iprodione, lotilaner, meperfluthrin, paichongding, pyflubumide, pyridalyl, pyrifluquinazon, pyriminostrobin, sarolaner, tetramethylfluthrin, tetraniliprole, tetrachlorantraniliprole, tioxazafen, triflumezopyrim and iodomethane; and additionally preparations based on *Bacillus firmus* (I-1582, BioNeem, Votivo), and the following known active compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969), butyl [2-(2,4-dichlorophenyl)-3-oxo-4-oxaspiro[4.5]dec-1-en-1-yl]carbonate (known from CN 102060818), (3E)-3-[1-[(6-chloro-3-pyridyl)methyl]-2-pyridylidene]-1,1,1-trifluoropropan-2-one (known from WO2013/144213, N-(methylsulphonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926).

Fungicides

The active compounds specified herein by their common name are known and described, for example, in "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

(1) Ergosterol biosynthesis inhibitors, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33)

nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]-1H-imidazole 1-carbothioate, (1.65) pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-yl thiocyanate, (1.68) 5-(allylsulphanyl)-1-{[3-(2-chlorophenyl)-2-(2,4-difluorophenyl)oxiran-2-yl]methyl J}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-yl thiocyanate, (1.73) 1-{[rel(2R,3R)-3-(2-chlorophenyl)-2-(2,4-difluorophenyl)oxiran-2-yl]methyl}-1H-1,2,4-triazol-5-yl thiocyanate, (1.74) 5-(allylsulphanyl)-1-{[rel(2R,3S)-3-(2-chlorophenyl)-2-(2,4-difluorophenyl)oxiran-2-yl]methyl}-1H-1,2,4-triazole, (1.75) 5-(allylsulphanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain at complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxan, (2.23) thifluzamid, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy J}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)

pyridine-3-carboxamide, (2.43) isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain at complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl] ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl] phenyl}acetamide, (3.26) (2E)-2-{2-[({[(1E)-1-(3-{[(E)-1-fluoro-2-phenylvinyl]oxy}phenyl)ethylidene] amino}oxy)methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino] methyl}sulphanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl] phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Inhibitors of mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulphur and sulphur preparations including calcium polysulphide, (5.31) thiram, (5.32) tolylfluanid, (5.33) zineb, (5.34) ziram, (5.35) anilazine.

6) Compounds capable of inducing host defence, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of ATP production, for example (8.01) fentin acetate, (8.02) fentin chloride, (8.03) fentin hydroxide, (8.04) silthiofam.

9) Inhibitors of cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Inhibitors of signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) chinomethionat, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezine, (15.015) difenzoquat, (15.016) difenzoquat metilsulphate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and its salts, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanide, (15.048) triazoxide, (15.049) trichlamide, (15.050) zarilamid, (15.051) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1-(4-methoxyphenoxy)-3,3-dimethylbutan-2-yl 1H-imidazole-1-carboxylate, (15.056) 2,3,5,6-tetrachloro-4-(methylsulphonyl)pyridine, (15.057) 2,3-dibutyl-6-chlorothieno[2,3-d]pyrimidin-4 (3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl] pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarbonitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl) thiophene-2-sulphonohydrazide, (15.071) 5-fluoro-2-[(4-fluorobenzyl)oxy]pyrimidine-4-amine, (15.072) 5-fluoro-2-[(4-methylbenzyl)oxy]pyrimidine-4-amine, (15.073) 5-methyl-6-octyl[1,2,4]triazolo[1,5-a]pyrimidine-7-amine, (15.074) ethyl (2Z)-3-amino-2-cyano-3-phenylacrylate, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-yn-1-yloxy)phenyl]propanamide, (15.077) N-[(4-chlorophenyl)(cyano)methyl]-3-[3-methoxy-4-(prop-2-yn-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N—{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.086) N-methyl-2-(1-{[5-methyl-3-(trifluoromethyl)-1H-pyrazol-1-yl] acetyl}piperidin-4-yl)-N-[(1S)-1,2,3,4-tetrahydronaphthalen-1-yl]-1,3-thiazole-4-carboxamide, (15.087) pentyl {6-[({[(1-methyl-1H-tetrazol-5-yl)(phenyl)methylene]amino}oxy)methyl]pyridin-2-yl}carbamate, (15.088) phenazine-1-carboxylic acid, (15.089) quinolin-8-ol, (15.090) quinolin-8-ol sulphate (2:1), (15.091) tert-butyl {6-[({[(1-methyl-1H-tetrazol-5-yl)(phenyl)methylene]amino}oxy)methyl]pyridin-2-yl}carbamate, (15.092) (5-bromo-2-methoxy-4-methylpyridin-3-yl)(2,3,4-trimethoxy-6-methylphenyl) methanone, (15.093) N-[2-(4-{[3-(4-chlorophenyl)prop-2-yn-1-yl]oxy}-3-methoxyphenyl)ethyl]-N2-(methylsulphonyl)valinamide, (15.094) 4-oxo-4-[(2-phenylethyl)amino]butanoic acid, (15.095) but-3-yn-1-yl {6-[({[(Z)-(1-methyl-1H-tetrazol-5-yl)(phenyl)methylene]amino}oxy)methyl]pyridin-2-yl}carbamate, (15.096) 4-amino-5-fluoropyrimidin-2-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-

5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazole-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazole-5-amine, (15.139) 4-(2-chloro-4-fluorophenyl)-N-(2,6-difluorophenyl)-1,3-dimethyl-1H-pyrazole-5-amine, (15.140) 4-(2-chloro-4-fluorophenyl)-N-(2-chloro-6-fluorophenyl)-1,3-dimethyl-1H-pyrazole-5-amine, (15.141) 4-(2-bromo-4-fluorophenyl)-N-(2-chloro-6-fluorophenyl)-1,3-dimethyl-1H-pyrazole-5-amine, (15.142) N-(2-bromo-6-fluorophenyl)-4-(2-chloro-4-fluorophenyl)-1,3-dimethyl-1H-pyrazole-5-amine, (15.143) 4-(2-bromo-4-fluorophenyl)-N-(2-bromophenyl)-1,3-dimethyl-1H-pyrazole-5-amine, (15.144) 4-(2-bromo-4-fluorophenyl)-N-(2-bromo-6-fluorophenyl)-1,3-dimethyl-1H-pyrazole-5-amine, (15.145) 4-(2-bromo-4-fluorophenyl)-N-(2-chlorophenyl)-1,3-dimethyl-1H-pyrazole-5-amine, (15.146) N-(2-bromophenyl)-4-(2-chloro-4-fluorophenyl)-1,3-dimethyl-1H-pyrazole-5-amine, (15.147) 4-(2-chloro-4-fluorophenyl)-N-(2-chlorophenyl)-1,3-dimethyl-1H-pyrazole-5-amine, (15.148) 4-(2-bromo-4-fluorophenyl)-N-(2,6-difluorophenyl)-1,3-dimethyl-1H-pyrazole-5-amine, (15.149) 4-(2-bromo-4-fluorophenyl)-N-(2-fluorophenyl)-1,3-dimethyl-1H-pyrazole-5-amine, (15.150) N'-(4-{3-[(difluoromethyl)sulphanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulphanyl]phenoxy}phenyl)-N-ethyl-N-methylimidoformamide, (15.152) N'-(2,5-dimethyl-4-{3-[(2,2,2-trifluoroethyl)sulphanyl]phenoxy}phenyl)-N-ethyl-N-methylimidoformamide, (15.153) N'-(2,5-dimethyl-4-{3-[(2,2,3,3-tetrafluoropropyl)sulphanyl]phenoxy}phenyl)-N-ethyl-N-methylimidoformamide, (15.154) N'-(2,5-dimethyl-4-{3-[(pentafluoroethyl)sulphanyl]phenoxy}phenyl)-N-ethyl-N-methylimidoformamide, (15.155) N'-(4-{[3-(difluoromethoxy)phenyl]sulphanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulphanyl}phenyl)-N-ethyl-N-methylimidoformamide, (15.157) N'-(2,5-dimethyl-4-{[3-(2,2,2-trifluoroethoxy)phenyl]sulphanyl}phenyl)-N-ethyl-N-methylimidoformamide, (15.158) N'-(2,5-dimethyl-4-{[3-(2,2,3,3-tetrafluoropropoxy)phenyl]sulphanyl}phenyl)-N-ethyl-N-methylimidoformamide, (15.159) N'-(2,5-dimethyl-4-{[3-(pentafluoroethoxy)phenyl]sulphanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]

acetyl}piperidin-4-yl)-1,3-thiazol-4-yl]-4,5-dihydro-1,2-oxazol-5-yl}phenyl methanesulphonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulphonate, (15.172) 2-{(5R)-3-[2-(1-{[3,5-bis(difluoromethyl)-1H-pyrazol-1-yl]acetyl}piperidin-4-yl)-1, 3-thiazol-4-yl]-4,5-dihydro-1,2-oxazol-5-yl}phenyl methanesulphonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulphonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces micro-flavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, especially strain ATCC 74040, *Coniothyrium minitans*, especially strain CON/M/91-8 (Accession No. DSM-9660), *Lecanicillium* spp., especially strain HRO LEC 12, *Lecanicillium lecanii*, (formerly known as *Verticillium lecanii*), especially strain KV01, *Metarhizium anisopliae*, especially strain F52 (DSM3884/ATCC 90448), *Metschnikowia fructicola*, especially strain NRRL Y-30752, *Paecilomyces fumosoroseus* (new: *Isaria fumosorosea*), especially strain IFPC 200613, or strain Apopka 97 (Accession No. ATCC 20874), *Paecilomyces lilacinus*, especially *P. lilacinus* strain 251 (AGAL 89/030550), *Talaromyces flavus*, especially strain V117b, *Trichoderma atroviride*, especially strain SC1 (Accession Number CBS 122089), *Trichoderma harzianum*, especially *T. harzianum rifai* T39 (Accession Number CNCM I-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum, Artemisia absinthium*, azadirachtin, Biokeeper WP, *Cassia nigricans, Celastrus angulatus, Chenopodium anthelminticum*, chitin, Armour-Zen, Dryopteris filix-mas, *Equisetum arvense*, Fortune Aza, Fungastop, Heads Up (*Chenopodium quinoa* saponin extract), Pyrethrum/Pyrethrins, *Quassia amara, Quercus*, Quillaja, Regalia, "Requiem™ Insecticide", rotenone, ryania/ryanodine, *Symphytum officinale, Tanacetum vulgare*, thymol, Triact 70, TriCon, *Tropaeulum majus, Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material and vegetative and generative propagation material, for example cuttings, tubers, rhizomes, slips and seeds.

Treatment according to the invention of the plants and plant parts with the compounds of the formula (I) is carried out directly or by allowing the compounds to act on their surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better storage life and/or processability of the harvested products. Further and particularly emphasized examples of such properties are increased resistance of the plants against animal and microbial pests, such as insects, arachnids, nematodes, mites, slugs and snails owing, for example, to toxins formed in the plants, in particular those produced in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure of pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been pre-swollen in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of agrochemically active compounds. Alkyl naphthalenesulphonates, such as diisopropyl or diisobutyl naphthalenesulphonates, can be used with preference.

Suitable dispersants and/or emulsifiers which may be present in the seed-dressing formulations usable in accordance with the invention are all nonionic, anionic and cationic dispersants customary for the formulation of agrochemically active compounds. Nonionic or anionic dispersants or mixtures of nonionic or anionic dispersants/can be used with preference. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions.

Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable homeotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; and also nuisance and hygiene pests from the order of the Blattarida.

Arthropods further include:

from the subclass of the Acari (Acarina) and the order of the Metastigmata, for example from the family of Argasidae like *Argas* spp., *Ornithodorus* spp., *Otobius* spp., from the family of Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order of Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic protozoa include:

Mastigophora (*Flagellata*), for example Trypanosomatidae, for example *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example *Giardia lamblia*, *G. canis*;

Sarcomastigophora (Rhizopoda) such as Entamoebidae, for example *Entamoeba histolytica*, Hartmanellidae, for example *Acanthamoeba* sp., *Harmanella* sp.;

Apicomplexa (Sporozoa) such as Eimeridae, for example *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E.* spec., *E. stiedai*, *E. suis*, *E. tenella*, *E. truncata*, *E. truttae*, *E. zuernii*, *Globidium* spec., *Isospora belli*, *I. canis*, *I. felis*, *I. ohioensis*, *I. rivolta*, *I.* spec., *I. suis*, *Cystisospora* spec., *Cryptosporidium* spec., in particular *C. parvum*; such as Toxoplasmadidae, for example *Toxoplasma gondii*, *Hammondia heydornii*, *Neospora caninum*, *Besnoitia besnoitii*; such as Sarcocystidae, for example *Sarcocystis bovicanis*, *S. bovihominis*, *S. ovicanis*, *S. ovifelis*, *S. neurona*, *S.* spec., *S. suihominis*, such as Leucozoidae, for example *Leucozytozoon simondi*, such as Plasmodiidae, for example *Plasmodium berghei*, *P. falciparum*, *P. malariae*, *P. ovale*, *P. vivax*, *P.* spec., such as Piroplasmea, for example *Babesia argentina*, *B. bovis*, *B. canis*, *B.* spec., *Theileria parva*, *Theileria* spec., such as Adeleina, for example *Hepatozoon canis*, *H.* spec.

Pathogenic endoparasites which are helminths include Platyhelmintha (e.g. Monogenea, cestodes and trematodes), nematodes, Acanthocephala, and Pentastoma. These include: Monogenea: e.g.: *Gyrodactylus* spp., *Dactylogyrus* spp., *Polystoma* spp.;

cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

nematodes: Trichinellida, for example: *Trichuris* spp., *Capillaria* spp., *Paracapillaria* spp., *Eucoleus* spp., *Trichomosoides* spp., *Trichinella* spp.;

from the order of the Tylenchida, for example: *Micronema* spp., *Strongyloides* spp.;

from the order of the Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp.,

*Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

from the order of the Echinorhynchida, for example *Acanthocephalus* spp., *Echinorhynchus* spp., *Leptorhynchoides* spp.;

Pentastoma: from the order of the Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, in particular an arthropodicide such as an insecticide or an acaricide. A further aspect relates to the use of a compound of the formula (I) as an antiectoparasitic agent, in particular an arthropodicide such as an insecticide or an acaricide, for example in animal husbandry, in animal breeding, in animal houses or in the hygiene sector.

Anthelmintic Mixing Components

The following anthelmintic mixing components may be mentioned by way of example:

anthelmintically active compounds including trematicidally and cestocidally active compounds:

from the class of the macrocyclic lactones, e.g.: abamectin, doramectin, emamectin, eprinomectin, ivermectin, milbemycin, moxidectin, nemadectin, selamectin;

from the class of the benzimidazoles and probenzimidazoles, e.g.: albendazole, albendazole sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, e.g.: emodepside, PF1022;

from the class of the aminoacetonitrile derivatives, e.g.: monepantel;

from the class of the tetrahydropyrimidines, e.g.: morantel, pyrantel, oxantel;

from the class of the imidazothiazoles, e.g.: butamisole, levamisole, tetramisole;

from the class of the salicylanilides, e.g.: bromoxanide, brotianide, clioxanide, closantel, niclosamide, oxyclozanide, rafoxanide, tribromsalan;

from the class of the paraherquamides, e.g.: derquantel, paraherquamide;

from the class of the aminophenylamidines, e.g.: amidantel, deacylated amidantel (dAMD), tribendimidine;

from the class of the organophosphates, e.g.: coumaphos, crufomate, dichlorvos, haloxone, naphthalofos, trichlorfon;

from the class of the substituted phenols, e.g.: bithionol, disophenol, hexachlorophene, niclofolan, meniclopholan, nitroxynil;

from the class of the piperazinones, e.g.: praziquantel, epsiprantel;

from other diverse classes, e.g.: amoscanate, bephenium, bunamidine, clonazepam, clorsulon, diamfenetid, dichlorophen, diethylcarbamazine, emetine, hetolin, hycanthone, lucanthone, miracil, mirasan, niclosamide, niridazole, nitroxynil, nitroscanate, oltipraz, omphalotin, oxamniquin, paromomycin, piperazine, resorantel.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:
1) mosquitoes
   *Anopheles*: malaria, filariosis;
   *Culex*: Japanese encephalitis, filariasis, other viral diseases, transmission of worms;
   *Aedes*: yellow fever, dengue fever, filariasis, other viral diseases;
   Simulidae: transmission of worms, in particular *Onchocerca volvulus*;
2) lice: skin infections, epidemic typhus;
3) fleas: plague, endemic typhus;
4) flies: sleeping sickness (trypanosomiasis); cholera, other bacterial diseases;
5) mites: acariosis, epidemic typhus, rickettsialpox, tularaemia, Saint Louis encephalitis, tick-borne encephalitis (TBE), Crimean-Congo haemorrhagic fever, borreliosis;
6) ticks: borellioses such as *Borrelia duttoni*, tick-borne encephalitis, Q fever (*Coxiella burnetii*), babesioses (*Babesia canis canis*).

Examples of vectors in the context of the present invention are insects, such as aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

PREPARATION EXAMPLES 2-(3-Ethylsulphonylimidazo[1,2-a]pyridin-2-yl)-3-methyl-6-(trifluoromethyl)imidazo[4,5-c]pyridine
(I-1)

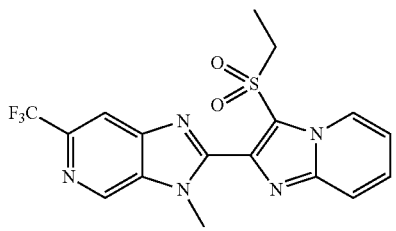 [SMILES: CCS(=O)(=O)c1c(-c2nc3cc(C(F)(F)F)ncc3n2C)nc2ccccn12]

52 mg (0.13 mmol) of 2-(3-ethylsulphanylimidazo[1,2-a]pyridin-2-yl)-3-methyl-6-(trifluoromethyl)-imidazo[4,5-c]pyridine were dissolved in 15 ml of dichloromethane, 31.8 mg (0.68 mmol) of formic acid and 133.9 mg (1.37 mmol) of hydrogen peroxide were added at room temperature and the mixture was then stirred at room temperature for 8 h. The mixture was diluted with water and sodium bisulphite solution was added, the mixture was stirred for 10 min and then stirred with 10% strength sodium bicarbonate solution. The organic phase was separated off, the aqueous phase was extracted twice with dichloromethane and the combined organic phases were then freed of the solvent under reduced pressure. The residue was purified by column chromatography purification by means of preparative HPLC using a water/acetonitrile gradient as mobile phase.

(log P (neutral): 2.07; MH$^+$: 410; $^1$H-NMR (400 MHz, D$_6$-DMSO) δ ppm: 1.28 (t, 3H), 3.87 (q, 2H), 4.08 (s, 3H), 7.41 (t, 1H), 7.75-7.79 (m, 1H), 7.99 (d, 1H), 8.29 (s, 1H), 9.07 (d, 1H), 9.28 (s, 1H).

2-(3-Ethylsulphanylimidazo[1,2-a]pyridin-2-yl)-3-methyl-6-(trifluoromethyl)imidazo[4,5-c]pyridine
(I-2)

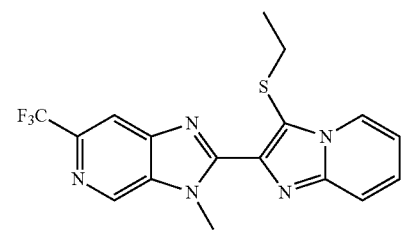 [SMILES: CCSc1c(-c2nc3cc(C(F)(F)F)ncc3n2C)nc2ccccn12]

101 mg (0.28 mmol) of 2-(3-chloroimidazo[1,2-a]pyridin-2-yl)-3-methyl-6-(trifluoromethyl)imidazo[4,5-c]pyridine and 73 mg (0.86 mmol) of sodium ethanethiolate were stirred in DMF at room temperature for 8 h. Water was added and the mixture was extracted twice with ethyl acetate. The combined organic phases were washed with a sodium chloride solution, removed, dried over sodium sulphate and freed of the solvent under reduced pressure.

(log P (neutral): 2.75; MH$^+$: 378; $^1$H-NMR (400 MHz, D$_6$-DMSO) δ ppm: 1.08 (t, 3H), 3.04 (q, 2H), 4.29 (s, 3H), 7.24 (t, 1H), 7.54-7.58 (m, 1H), 7.83 (d, 1H), 8.26 (s, 1H), 8.79 (d, 1H), 9.22 (s, 1H).

2-(3-Chloroimidazo[1,2-a]pyridin-2-yl)-3-methyl-6-(trifluoromethyl)imidazo[4,5-c]pyridine (V-1)

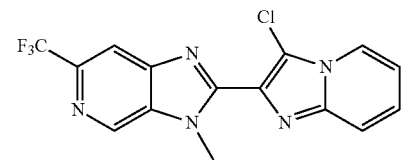 [SMILES: Cn1c(-c2nc3ccccn3c2Cl)nc2cc(C(F)(F)F)ncc21]

250 mg (1.30 mmol) of N$^3$-methyl-6-(trifluoromethyl)pyridine-3,4-diamine, 305 mg (1.30 mmol) of 3-chloroimidazo[1,2-a]pyridine-2-carboxylic acid hydrochloride and 251 mg (1.30 mmol) of 1-(3-dimethylaminopropyl)-3-ethylcarbodiimide hydrochloride (EDCI) were stirred in 5 ml of pyridine at 120° C. for 9 h. The reaction mixture was freed of the solvent under reduced pressure, then water was added and the mixture was extracted three times with ethyl acetate. The combined organic phases were dried over sodium sulphate, concentrated again and purified by column chromatography purification via preparative HPLC using a water/acetonitrile gradient as mobile phase.

(log P (neutral): 2.38; MH+: 352; ¹H-NMR (400 MHz, D₆-DMSO) δ ppm: 4.42 (s, 3H), 7.26 (t, 1H), 7.52-7.57 (m, 1H), 7.84 (d, 1H), 8.27 (s, 1H), 8.54 (d, 1H), 9.22 (s, 1H).

6-[3-(Ethylsulphonyl)imidazo[1,2-a]pyridin-2-yl]-2,2-difluoro-5-methyl-5H-[1,3]dioxolo[4,5-f]benzimidazole (I-41)

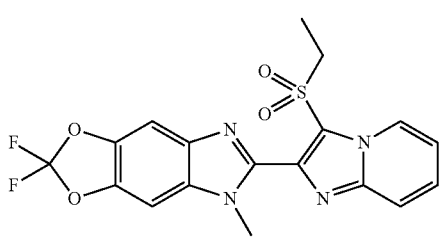 [SMILES: CCS(=O)(=O)c1c(-c2nc3cc4c(cc3n2C)OC(F)(F)O4)nc2ccccn12]

48 mg (0.11 mmol) of 6-[3-(ethylsulphonyl)imidazo[1,2-a]pyridin-2-yl]-2,2-difluoro-5H-[1,3]dioxolo[4,5-f]benzimidazole were dissolved in 5 ml of acetone, 32.7 mg (0.23 mmol) of potassium carbonate and 23.5 mg (0.16 mmol) of iodomethane were added at room temperature and the mixture was then heated at 60° C. for 4 h. The solvent was removed under reduced pressure, the residue was dissolved in ethyl acetate and the organic phase was washed with water. The aqueous phase was extracted twice with ethyl acetate, the combined organic phases were dried over sodium sulphate and the solvent was then removed under reduced pressure. The crude product was purified by MPLC using a cyclohexane/ethyl acetate gradient as mobile phase.

(log P (neutral): 2.62; MH+: 421; ¹H-NMR (600 MHz, CD₃CN)δ ppm: 1.32 (t, 3H), 3.82 (q, 2H), 3.92 (s, 3H), 7.20-7.22 (m, 1H), 7.42 (s, 1H), 7.50 (s, 1H), 7.61-7.64 (m, 1H), 7.78-7.80 (m, 1H), 9.10-9.12 (m, 1H).

6-[3-(Ethylsulphonyl)imidazo[1,2-a]pyridin-2-yl]-2,2-difluoro-5H-[1,3]dioxolo[4,5-f]benzimidazole (I-40)

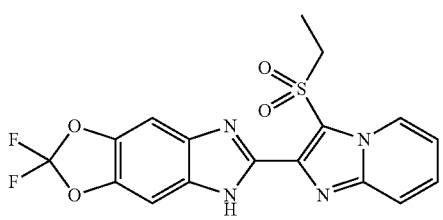 [SMILES: CCS(=O)(=O)c1c(-c2nc3cc4c(cc3[nH]2)OC(F)(F)O4)nc2ccccn12]

128 mg (0.33 mmol) of 1-[bis(dimethylamino)methylene]-1H-1,2,3-triazolo[4,5-b]pyridinium 3-oxide hexafluorophosphate (HATU) and 115 mg (0.89 mmol) of N-ethyldiisopropylamine were added to a solution of 57 mg (0.22 mmol) of 3-(ethylsulphonyl)imidazo[1,2-a]pyridine-2-carboxylic acid in 3 ml of tetrahydrofuran and 3 ml of dimethylformamide, and the mixture was stirred at room temperature for 15 min. A solution of 42.1 mg (0.22 mmol) of 2,2-difluoro-1,3-benzodioxole-5,6-diamine in 3 ml of tetrahydrofuran was then added dropwise, and the reaction mixture was stirred at room temperature overnight. Water was added and the mixture was extracted three times with ethyl acetate. The combined organic phases were dried over sodium sulphate and the solvent was then removed. The residue was dissolved in 20 ml of toluene, and 91.2 mg (0.48 mmol) of p-toluenesulphonic acid and molecular sieve were added. The reaction mixture was heated at 120° C. for 2 h. The mixture was diluted with water and extracted three times with ethyl acetate. The combined organic phases were washed twice with sodium bicarbonate solution and once with sodium chloride solution and dried over sodium sulphate, and the solvent was then removed. The crude product was purified by HPLC using a water/acetonitrile gradient as mobile phase.

(log P (neutral): 2.59; MH+: 407; ¹H-NMR (400 MHz, D₆-DMSO) δ ppm: 1.28 (t, 3H), 4.17 (q, 2H), 7.31-7.34 (m, 1H), 7.53 (s, 1H), 7.68-7.72 (m, 1H), 7.77 (s, 1H), 7.91 (d, 1H), 9.21 (d, 1H).

2-[3-(Ethylsulphonyl)imidazo[1,2-a]pyridin-2-yl]-6-(trifluoromethyl)[1,3]oxazolo[5,4-b]pyridine (I-44)

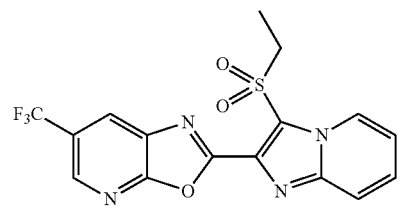 [SMILES: CCS(=O)(=O)c1c(-c2nc3cc(C(F)(F)F)cnc3o2)nc2ccccn12]

21 mg (0.05 mmol) of 2-[3-(ethylsulphanyl)imidazo[1,2-a]pyridin-2-yl]-6-(trifluoromethyl)[1,3]oxazolo[5,4-b]pyridine were dissolved in 10 ml of dichloromethane, 29.8 mg (0.17 mmol) of 3-chloroperoxybenzoic acid (MCPBA) were added at 0° C. and the mixture was then stirred at room temperature for 4 h. The mixture was diluted with water and sodium bisulphite solution was added, the mixture was stirred for 10 min and then stirred with 10% strength sodium bicarbonate solution.

The organic phase was separated off, the aqueous phase was extracted twice with dichloromethane and the combined organic phases were then freed of the solvent under reduced pressure. The residue was purified by column chromatography purification by means of preparative HPLC using a water/acetonitrile gradient as mobile phase.

(log P (neutral): 2.52; MH+: 397; ¹H-NMR (400 MHz, D₆-DMSO) δ ppm: 1.33 (t, 3H), 3.92 (q, 2H), 7.40-7.44 (m, 1H), 7.76-7.80 (m, 1H), 8.02 (d, 1H), 8.97-8.98 (m, 2H), 9.13 (d, 1H).

2-[3-(Ethylsulphanyl)imidazo[1,2-a]pyridin-2-yl]-6-(trifluoromethyl)[1,3]oxazolo[5,4-b]pyridine (I-60)

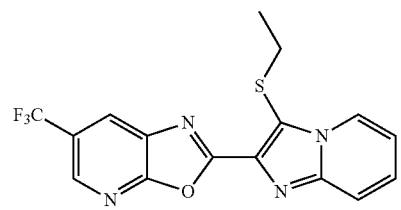 [SMILES: CCSc1c(-c2nc3cc(C(F)(F)F)cnc3o2)nc2ccccn12]

10.5 mg (0.09 mmol) of sodium carbonate were added to a solution of 39.8 mg (0.09 mmol) of N-[2-chloro-5-(trifluoromethyl)pyridin-3-yl]-3-(ethylsulphanyl)imidazo[1,2-a]pyridine-2-carboxamide in 1 ml of N,N-dimethylformamide, and the mixture was heated at 145° C. for 4 h. The reaction mixture was cooled to room temperature, poured onto ice-water and extracted twice with ethyl acetate. The combined organic phases were dried over sodium sulphate and the solvent was then removed. The crude product was purified by HPLC using a water/acetonitrile gradient as mobile phase.

(log P (neutral): 3.15; MH$^+$: 365; $^1$H-NMR (400 MHz, D$_6$-DMSO) δ ppm: 1.11 (t, 3H), 3.03 (q, 2H), 7.23-7.28 (m, 1H), 7.55-7.59 (m, 1H), 7.82 (d, 1H), 8.77 (d, 1H), 8.87 (s, 2H).

N-[2-Chloro-5-(trifluoromethyl)pyridin-3-yl]-3-(ethylsulphanyl)imidazo[1,2-a]pyridine-2-carboxamide (XXVI-1)

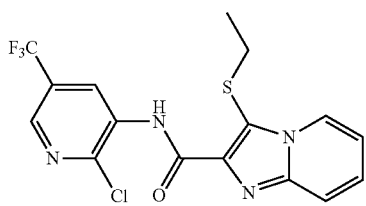 [SMILES: CCSc1c(C(=O)Nc2cc(C(F)(F)F)cnc2Cl)nc2ccccn12]

1.1 mg (9.37 mmol) of thionyl chloride were added dropwise to a solution of 298 mg (1.33 mmol) of 3-(ethylsulphanyl)imidazo[1,2-a]pyridine-2-carboxylic acid in 10 ml of acetonitrile, and the mixture was heated under reflux for 3 h. The solvent was removed under reduced pressure and the residue was twice co-evaporated with toluene. The residue was dissolved in 3 ml of N,N-dimethylformamide. Separately, 263 mg (1.33 mmol) of 2-chloro-5-(trifluoromethyl)pyridine-3-amine were added to a suspension at 0° C., of 107 mg (2.67 mmol) of sodium hydride in 7 ml of N,N-dimethylformamide, and the mixture was stirred for another 30 min. The acid chloride solution prepared beforehand was then slowly added dropwise at 0° C. The reaction mixture was stirred at room temperature for a further 2 h. The mixture was poured onto ice-water and extracted twice with ethyl acetate. The combined organic phases were dried over sodium sulphate and the solvent was then removed. The crude product was purified by HPLC using a water/acetonitrile gradient as mobile phase.

(log P (neutral): 4.39; MH$^+$: 401; $^1$H-NMR (400 MHz, D$_6$-DMSO) δ ppm: 1.09 (t, 3H), 2.98 (q, 2H), 7.22-7.25 (m, 1H), 7.55-7.60 (m, 1H), 7.82 (d, 1H), 8.66 (d, 1H), 8.73 (d, 1H), 9.07 (d, 1H).

In analogy to the examples and according to the above-described preparation processes, the following compounds of the formula (I) can be obtained:

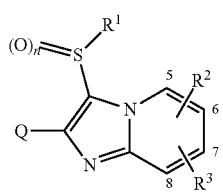

where R$^3$ represents hydrogen and where R$^1$, R$^2$, Q and n have the meanings given in the table below and where the bond from Q to the remainder of the molecule is indicated by a wavy line:

| Ex. | R$^1$ | n | R$^2$ | Q |
|-----|-------|---|-------|---|
| I-1 | C$_2$H$_5$ | 2 | H |  |
| I-2 | C$_2$H$_5$ | 0 | H | 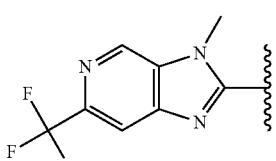 |
| I-3 | C$_2$H$_5$ | 0 | 6-Cl | 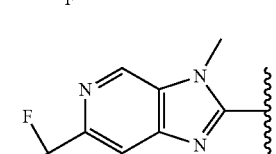 |
| I-4 | C$_2$H$_5$ | 2 | 6-Cl | 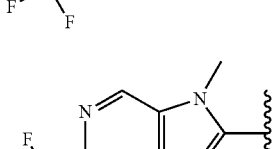 |
| I-5 | C$_2$H$_5$ | 0 | 6-CF$_3$ | 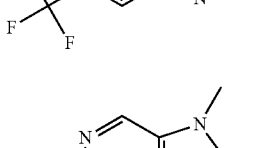 |
| I-6 | C$_2$H$_5$ | 2 | 6-CF$_3$ | 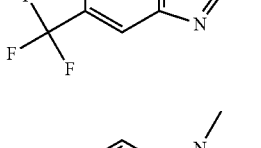 |
| I-7 | C$_2$H$_5$ | 1 | 6-Cl | 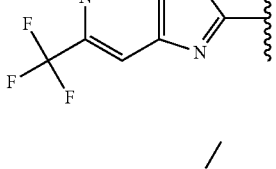 |
| I-8 | C$_2$H$_5$ | 1 | 6-CF$_3$ | 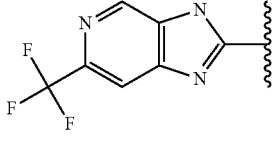 |

-continued

| Ex. | R¹ | n | R² | Q |
|---|---|---|---|---|
| I-9 | C₂H₅ | 0 | H | 5-CF₃-1-methylbenzimidazol-2-yl |
| I-10 | C₂H₅ | 2 | H | 5-CF₃-1-methylbenzimidazol-2-yl |
| I-11 | C₂H₅ | 1 | H | 5-CF₃-1-methylbenzimidazol-2-yl |
| I-12 | C₂H₅ | 2 | H | 5-CF₃-benzoxazol-2-yl |
| I-13 | C₂H₅ | 0 | 8-CF₃ | 6-CF₃-1-methylimidazo[4,5-c]pyridin-2-yl |
| I-14 | C₂H₅ | 0 | 8-Cl | 6-CF₃-1-methylimidazo[4,5-c]pyridin-2-yl |
| I-15 | C₂H₅ | 0 | 8-SC₂H₅ | 6-CF₃-1-methylimidazo[4,5-c]pyridin-2-yl |
| I-16 | C₂H₅ | 0 | 7-CF₃ | 6-CF₃-1-methylimidazo[4,5-c]pyridin-2-yl |
| I-17 | C₂H₅ | 2 | 7-CF₃ | 6-CF₃-1-methylimidazo[4,5-c]pyridin-2-yl |

-continued

| Ex. | R¹ | n | R² | Q |
|---|---|---|---|---|
| I-18 | C₂H₅ | 1 | 7-CF₃ | 6-CF₃-1-methylimidazo[4,5-c]pyridin-2-yl |
| I-19 | C₂H₅ | 2 | 8-Cl | 6-CF₃-1-methylimidazo[4,5-c]pyridin-2-yl |
| I-20 | C₂H₅ | 0 | 5-CF₃ | 6-CF₃-1-methylimidazo[4,5-c]pyridin-2-yl |
| I-21 | C₂H₅ | 2 | 5-CF₃ | 6-CF₃-1-methylimidazo[4,5-c]pyridin-2-yl |
| I-22 | C₂H₅ | 1 | 5-CF₃ | 6-CF₃-1-methylimidazo[4,5-c]pyridin-2-yl |
| I-23 | C₂H₅ | 2 | 7-Cl | 6-CF₃-1-methylimidazo[4,5-c]pyridin-2-yl |
| I-24 | C₂H₅ | 2 | 8-CF₃ | 6-CF₃-1-methylimidazo[4,5-c]pyridin-2-yl |
| I-25 | C₂H₅ | 1 | 8-CF₃ | 6-CF₃-1-methylimidazo[4,5-c]pyridin-2-yl |
| I-26 | C₂H₅ | 0 | 5-CH₃ | 5-CF₃-1-methylbenzimidazol-2-yl |

-continued

| Ex. | R¹ | n | R² | Q |
|---|---|---|---|---|
| I-27 | $C_2H_5$ | 0 | 5-$CF_3$ | 5-CF3, N-methyl benzimidazol-2-yl |
| I-28 | $C_2H_5$ | 0 | 6-$CF_3$ | 6-CF3, N-methyl benzimidazol-2-yl |
| I-29 | $C_2H_5$ | 0 | 6-Cl | 5-CF3, N-methyl benzimidazol-2-yl |
| I-30 | $C_2H_5$ | 0 | 7-$CF_3$ | 5-CF3, N-methyl benzimidazol-2-yl |
| I-31 | $C_2H_5$ | 0 | 5-$SC_2H_5$ | 5-CF3, N-methyl benzimidazol-2-yl |
| I-32 | $C_2H_5$ | 0 | 7-$SC_2H_5$ | 5-CF3, N-methyl benzimidazol-2-yl |
| I-33 | $C_2H_5$ | 2 | 7-$CH_3$ | 5-CF3, N-methyl benzimidazol-2-yl |
| I-34 | $C_2H_5$ | 2 | 7-$CF_3$ | 5-CF3, N-methyl benzimidazol-2-yl |

-continued

| Ex. | R¹ | n | R² | Q |
|---|---|---|---|---|
| I-35 | $C_2H_5$ | 2 | 6-$CH_3$ | 5-CF3, N-methyl benzimidazol-2-yl |
| I-36 | $C_2H_5$ | 2 | 6-$CF_3$ | 5-CF3, N-methyl benzimidazol-2-yl |
| I-37 | $C_2H_5$ | 0 | 7-$CH_3$ | 5-CF3, N-methyl benzimidazol-2-yl |
| I-38 | $C_2H_5$ | 0 | 6-$CH_3$ | 5-CF3, N-methyl benzimidazol-2-yl |
| I-39 | $C_2H_5$ | 2 | 8-$SO_2C_2H_5$ | CF3-imidazopyridine |
| I-40 | $C_2H_5$ | 2 | H | difluoro-dioxolo-benzimidazole |
| I-41 | $C_2H_5$ | 2 | H | difluoro-dioxolo-N-methylbenzimidazole |
| I-42 | $C_2H_5$ | 2 | 6-Cl | 5-CF3, N-methyl benzimidazol-2-yl |
| I-43 | $C_2H_5$ | 2 | H | 5-CF3 benzothiazol-2-yl |

-continued

| Ex. | R¹ | n | R² | Q |
|---|---|---|---|---|
| I-44 | C₂H₅ | 2 | H | 6-CF₃-[1,3]oxazolo[5,4-b]pyridin-2-yl |
| I-45 | C₂H₅ | 0 | 6-CH₃ | 1-methyl-6-CF₃-imidazo[4,5-c]pyridin-2-yl |
| I-46 | C₂H₅ | 2 | 5-CH₃ | 5-CF₃-1-methyl-benzimidazol-2-yl |
| I-47 | C₂H₅ | 2 | 6-CF₃ | 6-CF₃-[1,3]oxazolo[5,4-b]pyridin-2-yl |
| I-48 | C₂H₅ | 2 | 6-CH₃ | 1-methyl-6-CF₃-imidazo[4,5-c]pyridin-2-yl |
| I-49 | C₂H₅ | 2 | 7-CF₃ | 6-CF₃-[1,3]oxazolo[5,4-b]pyridin-2-yl |
| I-50 | C₂H₅ | 0 | 7-CF₃ | 6-CF₃-[1,3]oxazolo[5,4-b]pyridin-2-yl |
| I-51 | C₂H₅ | 2 | H | 6-CF₃-[1,3]thiazolo[5,4-b]pyridin-2-yl |
| I-52 | C₂H₅ | 0 | H | 1-methyl-6-CF₃-imidazo[4,5-b]pyridin-2-yl |
| I-53 | C₂H₅ | 2 | 6-CH₃ | 1-methyl-6-CF₃-imidazo[4,5-b]pyridin-2-yl |
| I-54 | C₂H₅ | 2 | 6-OCH₃ | 1-methyl-6-CF₃-imidazo[4,5-b]pyridin-2-yl |
| I-55 | C₂H₅ | 1 | 6-OCH₃ | 1-methyl-6-CF₃-imidazo[4,5-c]pyridin-2-yl |
| I-56 | C₂H₅ | 2 | 6-CH₃ | 6-CF₃-[1,3]oxazolo[5,4-b]pyridin-2-yl |
| I-57 | C₂H₅ | 0 | 5-CF₃ | 6-CF₃-[1,3]oxazolo[5,4-b]pyridin-2-yl |
| I-58 | C₂H₅ | 0 | 6-CF₃ | 6-CF₃-[1,3]oxazolo[5,4-b]pyridin-2-yl |
| I-59 | C₂H₅ | 2 | H | 1-methyl-6-CF₃-imidazo[4,5-b]pyridin-2-yl |
| I-60 | C₂H₅ | 0 | H | 6-CF₃-[1,3]oxazolo[5,4-b]pyridin-2-yl |

Preparation Examples of Intermediate Compounds 3-(Ethylsulphonyl)imidazo[1,2-a]pyridine-2-carboxylic acid (XXIII-1)

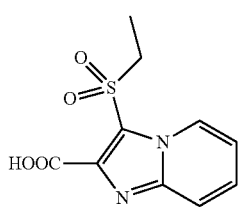

34.1 mg (1.42 mmol) of lithium hydroxide were added to a solution of 161 mg (0.57 mmol) of ethyl 3-(ethylsulphonyl)imidazo[1,2-a]pyridine-2-carboxylate in 5 ml of ethanol, and the mixture was stirred at room temperature for 3 h. The precipitate formed was collected.

(log P (acidic): 0.54; MH$^+$: 255; $^1$H-NMR (400 MHz, D$_6$-DMSO) δ ppm: 1.22 (t, 3H), 3.65 (q, 2H), 7.32 (t, 1H), 7.68 (t, 1H), 7.87 (d, 1H), 8.99 (d, 1H).

Ethyl 3-(ethylsulphonyl)imidazo[1,2-a]pyridine-2-carboxylate (XXIV-1)

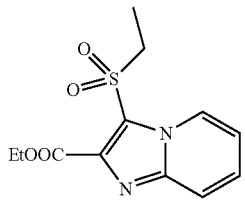 [SMILES: CCS(=O)(=O)c1c(C(=O)O)nc2ccccn12]

210 mg (0.83 mmol) of ethyl 3-(ethylsulphanyl)imidazo[1,2-a]pyridine-2-carboxylate were dissolved in 10 ml of dichloromethane, 434 mg (2.51 mmol) of 3-chloroperoxybenzoic acid (MCPBA) were added at 0° C. and the mixture was then stirred at room temperature for 2 h. The mixture was diluted with water and sodium bisulphite solution was added, the mixture was stirred for 10 min and then stirred with 10% strength sodium bicarbonate solution. The organic phase was separated off, the aqueous phase was extracted twice with dichloromethane and the combined organic phases were then freed of the solvent under reduced pressure.

(log P (neutral): 1.52; MH$^+$: 283; $^1$H-NMR (400 MHz, D$_6$-DMSO) δ ppm: 1.24 (t, 3H), 1.34 (t, 3H), 3.65 (q, 2H), 4.37 (q, 2H), 7.34 (t, 1H), 7.68-7.72 (m, 1H), 7.89 (d, 1H), 8.98 (d, 1H).

Ethyl 3-(ethylsulphanyl)imidazo[1,2-a]pyridine-2-carboxylate (XXII-1)

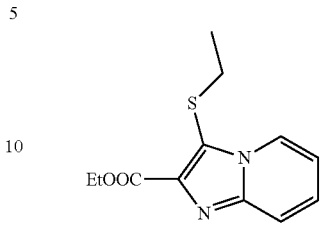

500 mg (2.22 mmol) of ethyl 3-chloroimidazo[1,2-a]pyridine-2-carboxylate were dissolved in 10 ml of N,N-dimethylformamide, 562 mg (6.67 mmol) of sodium thiomethoxide were added at room temperature and the mixture was then stirred at room temperature for 2.5 h. The reaction was diluted with water and extracted three times with ethyl acetate. The combined organic phases were dried over sodium sulphate and the solvent was then removed under reduced pressure. The crude product was purified by MPLC using a water/acetonitrile gradient as mobile phase.

(log P (neutral): 2.05; MH$^+$: 251; $^1$H-NMR (400 MHz, D$_6$-DMSO) δ ppm: 1.06 (t, 3H), 1.35 (t, 3H), 2.88 (q, 2H), 4.34 (q, 2H), 7.15-7.19 (t, 1H), 7.47-7.51 (m, 1H), 7.71 (d, 1H), 8.67 (d, 1H).

3-Chloro-7-(trifluoromethyl)imidazo[1,2-a]pyridine-2-carboxylic acid (III-1)

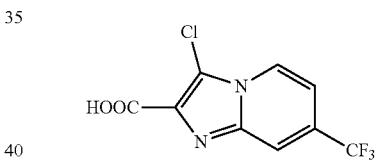

256 mg (10.6 mmol) of lithium hydroxide were added to a solution of 1.22 g (4.27 mmol) of ethyl 3-chloro-7-(trifluoromethyl)imidazo[1,2-a]pyridine-2-carboxylate in 20 ml of methanol, and the mixture was stirred at room temperature overnight. The solvent was removed, the residue was dissolved in water and the aqueous phase was extracted once with dichloromethane. The aqueous phase was then acidified with HCl solution and the precipitate formed was collected.

(log P (acidic): 1.50; MH$^+$: 265; $^1$H-NMR (400 MHz, D$_6$-DMSO) δ ppm: 7.38-7.42 (m, 1H), 8.26 (s, 1H), 8.62 (d, 1H).

Ethyl 3-chloro-7-(trifluoromethyl)imidazo[1,2-a]pyridine-2-carboxylate

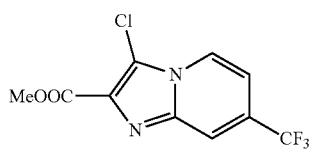 [SMILES: COC(=O)c1nc2cc(C(F)(F)F)ccn2c1Cl]

81.8 mg (0.61 mmol) of N-chlorosuccinimide (NCS) were added to a solution of 136 mg (0.55 mmol) of ethyl 7-(trifluoromethyl)imidazo[1,2-a]pyridine-2-carboxylate in 0.6 ml of N,N-dimethylformamide, and the mixture was stirred at 40° C. for 4 h. The reaction was quenched with sodium bisulphite solution and the aqueous phase was extracted three times with ethyl acetate. The combined organic phases were dried over sodium sulphate and the solvent was then removed under reduced pressure.

(log P (neutral): 2.10; MH+: 279; $^1$H-NMR (400 MHz, D$_6$-DMSO) δ ppm: 3.91 (s, 3H), 7.41-7.43 (m, 1H), 8.28 (s, 1H), 8.64 (d, 1H).

Ethyl 7-(trifluoromethyl)imidazo[1,2-a]pyridine-2-carboxylate

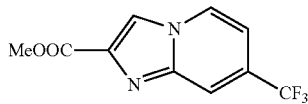

13.8 g (73.9 mmol) of methyl 3-bromo-2-oxopropanoate were added to a solution of 5.0 g (30.8 mmol) of 4-(trifluoromethyl)pyridine-2-amine in 70 ml of acetonitrile, and the mixture was stirred at 50° C. for 3 h. The precipitate formed was collected.

(log P (neutral): 1.59; MH+: 245; $^1$H-NMR (400 MHz, D$_6$-DMSO) δ ppm: 3.88 (s, 3H), 7.28-7.31 (m, 1H), 8.16 (s, 1H), 8.74 (s, 1H), 8.79 (d, 1H).

The log P values are measured according to EEC Directive 79/831 Annex V.A8 by HPLC (high-performance liquid chromatography) on a reversed-phase column (C 18). Temperature: 55° C.

The LC-MS determination in the acidic range is effected at pH 2.7 using 0.1% aqueous formic acid and acetonitrile (contains 0.1% formic acid) as eluents; linear gradient from 10% acetonitrile to 95% acetonitrile. Called log P (HCOOH) in the table.

LC-MS determination in the neutral range is effected at pH 7.8 with 0.001 molar aqueous ammonium hydrogencarbonate solution and acetonitrile as eluents; linear gradient from 10% acetonitrile to 95% acetonitrile. Called log P (neutral) in the table.

Calibration is carried out using unbranched alkan-2-ones (having 3 to 16 carbon atoms) with known log P values (log P values determined on the basis of the retention times by linear interpolation between two successive alkanones).

The NMR data of selected examples are listed either in conventional form (δ values, multiplet splitting, number of hydrogen atoms) or as NMR peak lists.

In each case, the solvent in which the NMR spectrum was recorded is stated.

NMR Peak List Method

The $^1$H NMR data of selected examples are stated in the form of $^1$H NMR peak lists. For each signal peak, first the δ value in ppm and then the signal intensity in round brackets are listed. The pairs of δ value-signal intensity numbers for different signal peaks are listed with separation from one another by semicolons.

The peak list for one example therefore has the form of:
δ$_1$ (intensity$_1$); δ$_2$ (intensity$_2$); . . . ; δ$_i$ (intensity$_i$); . . . ; δ$_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1$H NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional $^1$H-NMR printouts and thus usually contain all peaks listed in a conventional NMR interpretation.

In addition, like conventional $^1$H NMR printouts, they may show solvent signals, signals of stereoisomers of the target compounds which likewise form part of the subject-matter of the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional $^1$H NMR interpretation.

Further details of $^1$H NMR peak lists can be found in the Research Disclosure Database Number 564025

| LOGP_ NEUTRAL | LOGP_ HCOOH | NMR |
|---|---|---|
| 2.05 | 2.08 | Example I-1: $^1$H-NMR(400.0 MHz, d$_6$-DMSO): = 9.276(3.9); 9.220(0.4); 9.083(1.9); 9.065(2.0); 8.311(0.4); 8.292(4.1); 8.265(0.4); 8.008(1.7); 7.985(2.1); 7.787(1.0); 7.785(1.1); 7.770(1.2); 7.767(1.3); 7.747(0.9); 7.745(0.9); 7.425(1.0); 7.423(1.0); 7.408(1.9); 7.405(1.9); 7.391(0.9); 7.388(0.9); 4.421(1.8); 4.081(16.0); 3.902(1.1); 3.884(3.5); 3.865(3.5); 3.847(1.1); 3.309(74.3); 2.674(0.7); 2.670(1.0); 2.666(0.8); 2.523(3.0); 2.505(115.6); 2.501(152.9); 2.497(116.3); 2.332(0.7); 2.328(1.0); 2.323(0.7); 1.299(3.7); 1.280(8.1); 1.262(3.6); 1.234(0.4); 0.008(0.5); 0.000(15.0); −0.063(0.4) |
| 2.75 | 2.84 | Example I-2: $^1$H-NMR(400.0 MHz, d$_6$-DMSO): = 9.224(4.1); 8.823(0.3); 8.802(1.8); 8.785(1.8); 8.314(0.4); 8.261(4.0); 7.953(0.7); 7.841(1.7); 7.818(2.0); 7.577(1.0); 7.574(1.1); 7.560(1.2); 7.557(1.2); 7.552(1.0); 7.538(1.0); 7.535(0.9); 7.262(0.3); 7.255(1.0); 7.239(1.8); 7.237(1.8); 7.220(0.9); 6.838(0.3); 4.507(1.1); 4.422(2.0); 4.288(16.0); 4.019(0.6); 3.386(0.8); 3.318(63.2); 3.070(1.3); 3.052(4.1); 3.033(4.1); 3.015(1.4); 2.892(5.3); 2.875(0.2); 2.863(0.4); 2.812(0.4); 2.799(0.4); 2.732(4.6); 2.676(0.7); 2.671(1.0); 2.667(0.7); 2.524(2.6); 2.507(110.0); 2.502(145.5); 2.498(110.6); 2.333(0.7); 2.329(0.9); 2.325(0.8); 1.234(0.9); 1.221(0.4); 1.202(0.6); 1.183(0.3); |

| LOGP_NEUTRAL | LOGP_HCOOH | NMR |
|---|---|---|
| | 3.59 | 1.093(4.3); 1.075(8.9); 1.056(4.2); 0.146(1.0); 0.008(8.2); 0.000(197.0); −0.008(11.7); −0.150(1.0) Example I-3: $^1$H-NMR(400.0 MHz, $d_6$-DMSO): = 9.229(4.4); 8.886(2.9); 8.884(2.9); 8.268(4.7); 7.900(2.4); 7.876(2.8); 7.624(1.8); 7.619(1.9); 7.600(1.6); 7.595(1.7); 4.405(0.3); 4.278(16.0); 3.314(58.2); 3.090(1.3); 3.072(4.1); 3.053(4.2); 3.035(1.4); 2.670(1.0); 2.501(133.3); 2.497(109.0); 2.328(0.8); 1.234(0.5); 1.106(4.3); 1.087(8.7); 1.069(4.2); 0.000(33.0) |
| 2.61 | 2.67 | Example I-4: $^1$H-NMR(400.0 MHz, $d_6$-DMSO): = 9.278(4.2); 9.099(3.0); 9.097(2.9); 9.095(2.8); 8.313(0.3); 8.300(4.3); 8.071(2.3); 8.047(2.9); 7.866(2.0); 7.861(2.0); 7.842(1.6); 7.837(1.6); 4.086(16.0); 3.972(1.0); 3.953(3.5); 3.935(3.5); 3.917(1.1); 3.316(29.4); 2.671(0.4); 2.667(1.0); 2.506(52.4); 2.502(69.3); 2.497(54.6); 2.329(0.5); 2.324(0.4); 1.326(3.7); 1.308(8.0); 1.289(3.6); 0.000(21.5) |
| 3.75 | 3.81 | Example I-5: $^1$H-NMR(400.0 MHz, $d_6$-DMSO): = 9.250(3.7); 9.088(2.1); 8.313(0.9); 8.288(3.9); 8.060(1.5); 8.037(1.8); 7.811(1.5); 7.807(1.5); 7.787(1.3); 7.783(1.3); 4.292(16.0); 3.316(140.5); 3.127(1.2); 3.109(4.0); 3.090(4.0); 3.072(1.3); 2.675(1.2); 2.671(1.7); 2.666(1.3); 2.510(94.1); 2.506(185.5); 2.501(249.4); 2.497(190.6); 2.493(97.9); 2.333(1.2); 2.328(1.6); 2.324(1.2); 1.235(0.4); 1.110(4.2); 1.092(8.8); 1.073(4.0); 1.065(0.5); 0.008(3.0); 0.000(71.2); −0.008(3.0); −0.150(0.3) |
| 3.06 | 3.09 | Example I-6: $^1$H-NMR(400.0 MHz, $d_6$-DMSO): = 9.395(3.4); 9.293(4.6); 8.321(4.9); 8.226(2.1); 8.202(2.5); 8.046(2.4); 8.022(1.8); 4.133(0.4); 4.101(16.0); 4.034(1.3); 4.016(3.7); 3.998(3.8); 3.980(1.2); 3.316(88.5); 2.671(1.7); 2.506(213.5); 2.502(253.4); 2.328(1.6); 1.340(4.1); 1.321(8.2); 1.303(3.8); 0.000(1.5) |
| 2.83 | 2.93 | Example I-7: $^1$H-NMR(400.0 MHz, $d_6$-DMSO): = 9.405(2.9); 9.402(2.9); 9.260(4.2); 8.313(3.0); 8.247(4.6); 8.014(2.4); 7.990(2.8); 7.719(1.9); 7.714(1.8); 7.695(1.5); 7.690(1.6); 5.753(2.2); 4.443(16.0); 4.406(0.6); 4.085(0.4); 3.777(0.4); 3.757(1.1); 3.738(1.0); 3.723(1.3); 3.705(1.1); 3.686(0.4); 3.579(0.5); 3.561(1.2); 3.542(1.3); 3.527(1.0); 3.508(1.0); 3.490(0.5); 3.402(0.3); 3.370(0.5); 3.315(482.6); 2.670(8.1); 2.644(0.5); 2.505(967.2); 2.501(1216.0); 2.422(0.8); 2.413(0.8); 2.401(0.8); 2.395(0.8); 2.363(0.5); 2.328(7.7); 1.412(3.9); 1.393(8.1); 1.375(3.6); 1.306(0.3); 1.260(0.3); 1.245(0.3); 1.233(0.6); 0.000(10.5) |
| | 3.25 | Example I-8: $^1$H-NMR(400.0 MHz, $d_6$-DMSO): = 9.782(1.9); 9.275(3.5); 9.246(1.6); 8.959(0.9); 8.313(0.5); 8.284(1.7); 8.259(3.6); 8.257(3.7); 8.152(1.4); 8.129(1.7); 8.056(0.6); 8.032(0.8); 7.884(1.4); 7.879(1.4); 7.860(1.2); 7.855(1.2); 7.780(0.7); 7.776(0.7); 7.756(0.6); 7.752(0.6); 4.466(16.0); 4.417(7.8); 3.788(0.8); 3.770(0.9); 3.755(1.2); 3.737(1.1); 3.603(1.1); 3.585(1.2); 3.570(0.9); 3.551(0.8); 3.315(98.3); 2.675(0.7); 2.671(1.0); 2.666(0.7); 2.661(0.3); 2.524(2.3); 2.519(3.6); 2.511(54.7); 2.506(114.1); 2.502(153.7); 2.497(112.7); 2.492(55.0); 2.337(0.3); 2.333(0.7); 2.328(1.0); 2.324(0.7); 2.073(0.7); 1.428(3.6); 1.410(8.1); 1.391(3.5); 0.146(1.1); 0.008(8.5); 0.000(245.0); −0.009(9.1); −0.150(1.1) |
| 3.41 | 3.25 | Example I-9: $^1$H-NMR(400.0 MHz, $d_6$-DMSO): = 8.786(1.7); 8.768(1.8); 8.108(2.6); 7.902(1.7); 7.880(2.0); 7.819(1.7); 7.797(2.0); 7.675(1.5); 7.672(1.4); 7.653(1.2); 7.651(1.2); 7.554(0.9); 7.552(1.2); 7.537(1.1); 7.534(1.2); 7.529(0.8); 7.515(0.9); 7.512(0.9); 7.236(1.0); 7.234(1.0); 7.219(1.7); 7.217(1.8); 7.202(0.9); 7.200(0.8); 4.149(16.0); 3.318(51.5); 3.068(1.2); 3.050(4.0); 3.031(4.0); 3.013(1.3); 2.676(0.3); 2.671(0.5); 2.667(0.4); 2.507(60.2); 2.502(78.8); 2.498(57.5); 2.333(0.4); 2.329(0.5); 2.324(0.3); 1.398(1.4); 1.092(4.3); 1.073(8.9); 1.055(4.1); 0.000(3.9) |
| 2.64 | 2.70 | Example I-10: $^1$H-NMR(400.0 MHz, $d_6$-DMSO): = 9.095(1.8); 9.077(1.9); 8.313(0.5); 8.125(2.7); 7.991(1.7); 7.968(2.0); 7.945(1.7); 7.924(2.0); 7.767(1.0); 7.747(1.5); 7.726(1.7); 7.724(2.2); 7.699(1.3); 7.403(1.0); 7.386(1.7); 7.384(1.7); 7.369(0.9); 3.974(16.0); 3.944(1.0); 3.926(3.3); 3.907(3.4); 3.889(1.0); 3.317(130.6); 2.675(1.0); 2.671(1.4); 2.666(1.0); 2.524(3.6); 2.506(179.5); 2.501(236.7); 2.497(173.9); 2.333(1.0); 2.328(1.4); 2.324(1.1); 1.301(3.5); 1.283(7.8); 1.264(3.4); 0.146(0.6); 0.008(5.0); 0.000(138.8); −0.008(5.3); −0.149(0.7) |
| 2.85 | 2.92 | Example I-11: $^1$H-NMR(400.0 MHz, $d_6$-DMSO): = 9.291(1.7); 9.274(1.8); 8.314(0.4); 8.094(2.6); 7.930(3.2); 7.907(3.4); 7.688(1.2); 7.685(1.4); 7.663(1.2); 7.633(0.9); 7.630(1.0); 7.616(1.1); 7.613(1.2); 7.607(0.9); 7.593(0.9); 7.590(0.9); 7.243(0.9); 7.241(1.0); 7.226(1.7); 7.224(1.8); 7.209(0.9); 7.206(0.9); 4.329(16.0); 3.714(0.8); 3.696(1.0); 3.681(1.2); 3.662(1.2); 3.644(0.4); 3.559(0.4); 3.540(1.1); 3.522(1.3); 3.507(0.9); 3.489(0.8); 3.317(96.6); 2.675(0.9); 2.671(1.2); 2.666(0.9); 2.524(2.9); 2.510(73.1); 2.506(152.3); 2.501(204.3); 2.497(149.3); 2.493(73.0); 2.333(0.8); 2.328(1.2); 2.324(0.9); 1.388(3.8); 1.369(8.3); 1.351(3.7); 0.146(0.4); 0.008(2.9); 0.000(88.7); −0.008(3.4); −0.150(0.4) |
| 2.94 | 2.92 | Example I-12: $^1$H-NMR(601.6 MHz, CD3CN): = 9.178(1.8); 9.176(3.0); 9.175(1.8); 9.166(1.9); 9.165(3.0); 9.163(1.8); 8.216(3.2); 8.215(3.3); 8.213(3.1); 7.949(2.4); 7.935(3.1); 7.866(1.6); 7.864(2.7); 7.862(1.6); 7.851(2.0); 7.849(3.1); 7.847(2.0); 7.843(2.2); 7.841(2.1); 7.828(1.6); 7.826(1.6); 7.662(1.7); 7.660(1.7); 7.651(1.8); 7.649(2.1); 7.647(1.8); 7.645(1.6); 7.636(1.6); 7.634(1.6); 7.260(1.5); 7.258(1.5); 7.249(2.7); 7.247(2.6); 7.237(1.4); 7.235(1.3); 5.447(0.7); 3.879(2.3); 3.867(7.4); 3.855(7.5); 3.849(0.4); 3.842(2.4); 3.836(0.6); 3.824(0.6); 2.135(3.2); 2.051(0.3); 1.964(1.5); 1.956(3.4); 1.952(4.2); 1.948(21.5); 1.944(37.1); 1.940(52.4); 1.936(34.9); 1.932(18.0); 1.388(7.7); 1.376(16.0); 1.363(7.5); 1.303(0.7); 1.291(1.5); 1.278(0.8); 1.268(0.3); 0.000(3.0) |
| 3.71 | 1.40 | Example I-13: $^1$H-NMR(400.0 MHz, $d_6$-DMSO): = 9.231(4.1); 9.061(1.8); 9.044(1.9); 8.288(4.5); 8.047(1.7); 8.030(1.8); 7.381(1.1); 7.363(2.1); 7.346(1.1); 4.287(16.0); 3.331(187.0); 3.325(341.4); 3.102(1.3); 3.083(4.0); 3.065(4.1); 3.047(1.4); 2.671(1.2); 2.506(159.0); 2.502(194.2); 2.498(142.7); 2.329(1.2); 1.398(1.2); 1.235(0.6); 1.111(4.2); 1.093(8.7); 1.074(4.1); 0.000(4.6); −0.086(0.5) |
| 3.34 | 3.33 | Example I-14: $^1$H-NMR(400.0 MHz, $d_6$-DMSO): = 9.255(0.4); 9.233(3.3); 8.796(1.7); 8.794(1.8); 8.779(1.9); 8.777(1.9); 8.313(0.7); 8.276(3.5); 7.779(1.7); 7.777(1.9); 7.760(1.9); 7.758(1.9); 7.245(1.5); 7.227(2.4); 7.209(1.5); 4.318(2.1); 4.302(16.0); 3.374(0.5); 3.321(208.6); 3.083(1.2); 3.065(3.8); 3.047(3.9); |

| LOGP_NEUTRAL | LOGP_HCOOH | NMR |
|---|---|---|
| | | 3.028(1.2); 2.679(0.7); 2.675(1.4); 2.671(2.0); 2.666(1.5); 2.524(5.2); 2.510(119.9); 2.506(252.7); 2.502(340.5); 2.497(244.4); 2.492(115.6); 2.333(1.4); 2.328(1.9); 2.324(1.4); 2.319(0.7); 1.236(0.5); 1.097(4.3); 1.079(8.9); 1.060(4.1); 0.146(0.9); 0.008(7.1); 0.000(211.9); −0.009(7.6); −0.150(0.9) |
| 3.93 | 3.99 | Example I-15: $^1$H-NMR(400.0 MHz, d$_6$-DMSO): = 9.233(0.5); 9.215(3.1); 8.592(1.7); 8.577(1.7); 8.575(1.7); 8.314(0.5); 8.275(0.5); 8.260(3.3); 7.395(1.5); 7.379(1.7); 7.227(0.3); 7.207(1.5); 7.190(2.2); 7.172(1.2); 4.302(16.0); 3.316(96.3); 3.244(1.0); 3.226(3.2); 3.208(3.3); 3.189(1.0); 3.070(1.1); 3.066(0.8); 3.052(3.6); 3.033(3.7); 3.015(1.1); 2.675(0.9); 2.671(1.2); 2.666(0.9); 2.524(2.6); 2.519(4.1); 2.510(71.3); 2.506(153.0); 2.501(207.6); 2.497(150.8); 2.493(72.9); 2.333(0.9); 2.328(1.2); 2.324(0.9); 1.375(3.5); 1.356(7.7); 1.338(3.4); 1.098(0.7); 1.091(3.9); 1.079 (1.5); 1.072(8.4); 1.061(0.8); 1.054(3.8); 0.146(1.1); 0.008(8.4); 0.000(270.2); −0.009(10.6); −0.150(1.2) |
| 3.80 | 3.80 | Example I-16: $^1$H-NMR(400.0 MHz, d$_6$-DMSO): = 9.248(3.2); 8.988(1.4); 8.970(1.5); 8.369(2.0); 8.367(1.8); 8.290(3.4); 8.288(3.4); 7.481(1.3); 7.476(1.3); 7.463(1.3); 7.458(1.3); 4.292(16.0); 3.318(64.1); 3.120(1.2); 3.101(4.0); 3.083(4.0); 3.065(1.3); 2.676(0.5); 2.671(0.6); 2.667(0.5); 2.525(1.6); 2.520(2.5); 2.511(36.1); 2.507(76.5); 2.502(102.9); 2.498(73.3); 2.493(34.1); 2.334(0.4); 2.329(0.6); 2.324(0.4); 1.233(0.3); 1.107(4.4); 1.089(9.1); 1.071(4.1); 0.146(0.6); 0.008(5.5); 0.000(161.8); −0.009(5.6); −0.150(0.6) |
| 2.98 | 3.00 | Example I-17: $^1$H-NMR(400.0 MHz, d6-DMSO): = 9.289(3.7); 9.253(1.6); 9.234(1.7); 8.564(2.2); 8.319(4.0); 8.317(3.9); 7.680(1.4); 7.675(1.4); 7.661(1.4); 7.657(1.4); 4.094(16.0); 3.963(0.9); 3.944(3.2); 3.926(3.2); 3.907(0.9); 3.336(54.2); 3.330(43.0); 3.326(46.7); 2.671(0.4); 2.525(1.1); 2.511(27.5); 2.507(58.0); 2.502(78.0); 2.498(55.3); 2.493(25.7); 2.334(0.3); 2.329(0.4); 1.322(3.5); 1.304(8.1); 1.285(3.4); 0.008(0.7); 0.000(23.2); −0.009(0.8) |
| 3.25 | 3.29 | Example I-18: $^1$H-NMR(400.0 MHz, d$_6$-DMSO): = 9.507(1.6); 9.489(1.5); 9.273(3.6); 8.475(2.1); 8.312(0.4); 8.266(3.7); 7.527(1.4); 7.522(1.4); 7.508(1.3); 7.503(1.3); 4.457(16.0); 3.743(0.9); 3.724(0.9); 3.709(1.2); 3.691(1.2); 3.672(0.4); 3.577(1.2); 3.559(1.3); 3.544(0.9); 3.525(0.8); 3.508(0.3); 3.399(0.3); 3.329(149.5); 3.323(124.3); 2.675(0.9); 2.671(1.2); 2.524(3.0); 2.511(70.7); 2.507(147.2); 2.502(197.0); 2.498(141.0); 2.493(66.8); 2.333(0.8); 2.329(1.1); 2.324(0.8); 1.411(3.6); 1.392(8.0); 1.374(3.6); 0.146(0.4); 0.008(2.3); 0.000(70.4); −0.009(2.4) |
| 2.50 | 2.56 | Example I-19: $^1$H-NMR(400.0 MHz, d$_6$-DMSO): = 9.279(4.0); 9.045(2.1); 9.044(2.1); 9.028(2.3); 9.026(2.1); 8.307(4.3); 7.990(2.2); 7.971(2.4); 7.403(1.6); 7.385(2.6); 7.367(1.6); 5.753(1.1); 4.084(16.0); 3.894(1.0); 3.875(3.4); 3.857(3.5); 3.839(1.1); 3.317(87.8); 2.675(0.6); 2.671(0.8); 2.666(0.6); 2.506(103.4); 2.502(134.9); 2.497(98.6); 2.329(0.8); 1.299(3.6); 1.281(8.0); 1.263(3.6); 1.234(0.5); 0.146(0.7); 0.008(6.5); 0.000(153.0); −0.008(6.9); −0.150(0.7) |
| | 3.50 | Example I-20: $^1$H-NMR(400.0 MHz, d$_6$-DMSO): = 9.256(3.5); 8.313(0.5); 8.300(3.8); 8.176(1.5); 8.154(1.6); 7.898(1.4); 7.881(1.6); 7.669(1.0); 7.648(1.2); 7.629(0.9); 4.139(16.0); 3.373(0.5); 3.362(0.5); 3.352(0.7); 3.342(1.3); 3.320(261.2); 3.293(0.6); 2.963(0.9); 2.945(2.9); 2.926(3.0); 2.907(1.0); 2.675(1.0); 2.671(1.4); 2.666(1.0); 2.524(3.1); 2.511(80.7); 2.506(170.3); 2.502(229.0); 2.497(165.4); 2.493(79.0); 2.337(0.5); 2.333(1.0); 2.328(1.3); 2.324(0.9); 1.045(0.4); 1.030(0.4); 1.008(3.6); 0.989(7.7); 0.971(3.5); 0.146(0.6); 0.023(0.4); 0.008(4.7); 0.000(141.9); −0.008(4.4); −0.019(0.6); −0.150(0.6) |
| 2.66 | 2.69 | Example I-21: $^1$H-NMR(400.0 MHz, d$_6$-DMSO): = 9.292(4.3); 8.335(1.9); 8.308(5.3); 8.095(1.8); 8.076(2.2); 7.932(1.3); 7.910(1.6); 7.890(1.0); 4.080(16.0); 3.879(0.8); 3.861(2.6); 3.842(2.6); 3.823(0.9); 3.335(217.4); 3.329(279.2); 2.671(1.3); 2.506(172.3); 2.502(227.1); 2.498(172.5); 2.329(1.3); 2.073(0.4); 1.315(3.4); 1.297(7.4); 1.278(3.4); 0.008(0.8); 0.000(25.0) |
| 2.30 | 2.30 | Example I-22: $^1$H-NMR(400.0 MHz, d$_6$-DMSO): = 9.251(3.6); 8.311(4.2); 8.265(1.5); 8.242(1.6); 7.972(1.4); 7.955(1.7); 7.771(1.1); 7.750(1.2); 7.731(0.9); 4.156(0.6); 4.137(0.7); 4.123(0.8); 4.104(0.6); 3.861(16.0); 3.773(0.4); 3.371(0.6); 3.354(0.8); 3.317(236.7); 3.284(0.4); 2.675(1.1); 2.671(1.6); 2.666(1.2); 2.524(3.8); 2.510(92.6); 2.506(189.6); 2.501(251.2); 2.497(183.2); 2.492(90.7); 2.337(0.5); 2.333(1.1); 2.328(1.5); 2.324(1.1); 2.319(0.5); 1.287(2.8); 1.268(6.2); 1.249(2.8); 0.008(2.1); 0.000(63.0); −0.008(2.7) |
| 2.64 | 2.66 | Example I-23: $^1$H-NMR(400.0 MHz, d$_6$-DMSO): = 9.275(5.0); 9.048(2.8); 9.029(2.9); 8.302(5.4); 8.243(3.5); 7.492(1.9); 7.489(2.0); 7.470(1.9); 5.755(0.6); 4.399(0.4); 4.078(16.0); 3.920(1.2); 3.902(3.8); 3.883(3.8); 3.865(1.3); 3.318(390.5); 2.668(2.1); 2.501(361.0); 2.327(2.1); 1.303(4.0); 1.285(8.2); 1.266(3.9); 1.233(0.6); 0.146(0.4); 0.000(79.5); −0.002(73.2); −0.150(0.4) |
| 2.90 | 2.92 | Example I-24: $^1$H-NMR(400.0 MHz, d$_6$-DMSO): = 9.290(2.1); 9.276(6.1); 8.314(5.0); 8.250(1.9); 8.231(2.0); 7.544(1.2); 7.525(2.2); 7.507(1.1); 4.083(16.0); 3.941(1.1); 3.923(3.6); 3.904(3.7); 3.886(1.2); 3.323(397.4); 2.671(1.6); 2.505(229.6); 2.502(274.8); 2.328(1.5); 1.325(3.8); 1.306(8.1); 1.288(3.7); 0.000(19.3) |
| 3.21 | 3.29 | Example I-25: $^1$H-NMR(400.0 MHz, d$_6$-DMSO): = 9.539(1.9); 9.522(2.0); 9.254(4.3); 8.265(4.6); 8.122(1.8); 8.104(1.9); 7.399(1.1); 7.381(2.2); 7.363(1.1); 4.448(16.0); 3.736(0.8); 3.718(1.0); 3.703(1.3); 3.684(1.2); 3.666(0.4); 3.591(0.4); 3.573(1.2); 3.554(1.3); 3.539(1.0); 3.521(0.8); 3.324(241.3); 2.676(0.6); 2.671(0.7); 2.507(101.0); 2.502(127.1); 2.498(96.3); 2.329(0.7); 1.412(3.9); 1.393(8.3); 1.374(3.8); 0.000(10.6) |
| | 3.35 | Example I-26: $^1$H-NMR(400.0 MHz, d$_6$-DMSO): = 8.111(4.3); 7.908(2.1); 7.887(2.5); 7.803(0.4); 7.685(2.7); 7.672(2.5); 7.665(2.5); 7.650(2.5); 7.433(1.5); 7.415(2.0); 7.394(1.4); 7.225(0.4); 6.941.6(2.3); 6.924(2.1); 4.155(2.1); 3.999(16.0); 3.908(2.0); 3.336(185.7); 3.172(14.9); 3.055(0.7); 3.037(0.7); 2.993(1.6); |

| LOGP_NEUTRAL | LOGP_HCOOH | NMR |
|---|---|---|
| | | 2.975(4.9); 2.957(5.0); 2.938(1.6); 2.678(0.8); 2.509(146.0); 2.505(111.6); 2.335(0.8); 1.097(0.8); 1.079(1.6); 1.062(6.1); 1.044(11.6); 1.025(5.4) |
| | 4.09 | Example I-27: $^1$H-NMR(400.0 MHz, $d_6$-DMSO): = 8.165(1.9); 8.143(5.2); 7.935(1.8); 7.914(2.2); 7.884(1.9); 7.866(2.2); 7.711(1.8); 7.690(1.5); 7.655(1.3); 7.635(1.5); 7.615(1.0); 4.107(0.4); 4.094(0.4); 4.013(16.0); 3.908(2.6); 3.337(150.3); 3.182(2.5); 3.169(2.4); 2.974(1.1); 2.956(3.4); 2.937(3.4); 2.919(1.1); 2.682(0.5); 2.678(0.6); 2.513(85.0); 2.509(111.8); 2.505(86.7); 2.336(0.6); 1.015(4.0); 0.997(8.3); 0.978(3.9) |
| | 4.47 | Example I-28: $^1$H-NMR(400.0 MHz, $d_6$-DMSO): = 9.082(2.7); 8.140(3.5); 8.046(1.9); 8.022(2.3); 7.932(1.8); 7.911(2.5); 7.795(1.8); 7.791(1.8); 7.772(1.5); 7.768(1.5); 7.703(2.0); 7.681(1.6); 7.679(1.6); 4.167(16.0); 3.909(1.6); 3.337(159.2); 3.137(1.4); 3.119(4.5); 3.101(4.6); 3.082(1.5); 2.679(0.6); 2.514(80.2); 2.510(107.6); 2.505(84.3); 2.336(0.6); 1.114(4.8); 1.096(10.0); 1.077(4.7) |
| | 4.12 | Example I-29: $^1$H-NMR(400.0 MHz, $d_6$-DMSO): = 8.979(1.9); 8.961(2.0); 8.873(1.0); 8.349(3.0); 8.140(3.4); 8.120(1.2); 7.930(1.8); 7.909(2.4); 7.893(0.8); 7.884(0.9); 7.860(0.9); 7.702(2.0); 7.682(2.1); 7.665(0.6); 7.605(0.6); 7.602(0.6); 7.581(0.5); 7.467(1.8); 7.449(1.7); 4.166(16.0); 4.150(5.0); 3.908(1.9); 3.338(175.6); 3.129(1.4); 3.111(4.4); 3.092(4.5); 3.079(1.9); 3.075(1.7); 3.061(1.5); 3.042(0.5); 2.678(0.7); 2.513(89.3); 2.509(114.2); 2.505(88.1); 2.336(0.6); 1.111(5.9); 1.093(12.1); 1.074(5.7) |
| | 4.50 | Example I-30: $^1$H-NMR(400.0 MHz, $d_6$-DMSO): = 8.980(1.9); 8.962(2.0); 8.873(1.7); 8.350(3.0); 8.140(3.4); 8.120(2.0); 7.930(1.9); 7.910(2.6); 7.892(1.3); 7.885(1.5); 7.861(1.5); 7.702(2.0); 7.683(2.5); 7.665(1.0); 7.607(1.0); 7.602(1.0); 7.583(0.9); 7.579(0.8); 7.469(1.7); 7.465(1.7); 7.451(1.7); 7.447(1.7); 4.166(16.0); 4.150(8.2); 3.908(2.9); 3.338(300.3); 3.130(1.4); 3.111(4.2); 3.093(4.5); 3.079(2.7); 3.075(2.0); 3.061(2.4); 3.043(0.8); 2.678(1.0); 2.513(134.3); 2.509(176.3); 2.505(139.6); 2.336(1.0); 1.111(6.2); 1.093(12.4); 1.075(5.9) |
| | 3.95 | Example I-31: $^1$H-NMR(400.0 MHz, $d_6$-DMSO): = 8.116(4.9); 7.909(2.1); 7.888(2.5); 7.686(3.0); 7.665(2.5); 7.607(2.6); 7.585(3.5); 7.484(1.9); 7.465(2.7); 7.444(1.5); 7.310(1.3); 7.289(2.6); 7.267(2.6); 7.245(1.0); 7.067(3.4); 7.049(3.0); 4.150(0.4); 4.005(16.0); 3.908(4.6); 3.341(289.7); 3.228(1.7); 3.210(5.1); 3.191(5.2); 3.173(1.8); 3.005(1.7); 2.987(5.2); 2.968(5.3); 2.950(1.8); 2.678(0.9); 2.571(0.4); 2.509(159.2); 2.335(0.9); 1.657(3.1); 1.406(5.6); 1.387(11.5); 1.369(5.4); 1.264(0.4); 1.239(0.7); 1.065(6.2); 1.047(12.4); 1.028(5.8) |
| | 4.23 | Example I-32: $^1$H-NMR(400.0 MHz, $d_6$-DMSO): = 8.630(2.6); 8.612(2.7); 8.320(0.4); 8.105(5.6); 7.898(2.2); 7.877(2.5); 7.675(3.6); 7.653(2.9); 7.572(4.5); 7.089(3.3); 7.086(3.2); 7.071(3.2); 7.068(3.1); 4.151(15.5); 3.908(6.8); 3.516(0.4); 3.458(0.4); 3.337(473.1); 3.214(2.4); 3.196(7.3); 3.178(7.5); 3.159(2.4); 3.060(2.0); 3.041(6.2); 3.023(6.3); 3.005(2.2); 2.678(1.9); 2.513(252.5); 2.509(333.0); 2.505(259.0); 2.336(1.8); 1.367(7.8); |

| LOGP_NEUTRAL | LOGP_HCOOH | NMR |
|---|---|---|
| | | 1.349(16.0); 1.331(7.5); 1.305(0.3); 1.256(0.5); 1.239(0.5); 1.091(7.6); 1.079(15.4); 1.060(7.3); 0.006(0.6) |
| | 3.01 | Example I-33: $^1$H-NMR(400.0 MHz, $d_6$-DMSO): = 8.970(2.1); 8.952(2.1); 8.123(2.8); 7.943(1.7); 7.922(2.1); 7.776(2.6); 7.724(1.6); 7.721(1.6); 7.703(1.3); 7.700(1.3); 7.258(1.5); 7.254(1.5); 7.240(1.5); 7.236(1.5); 3.969(16.0); 3.922(1.0); 3.909(2.9); 3.903(3.2); 3.885(3.2); 3.867(1.0); 3.337(104.5); 2.683(0.4); 2.678(0.5); 2.514(58.2); 2.509(78.4); 2.505(61.2); 2.500(37.7); 2.336(0.5); 1.291(3.4); 1.273(7.6); 1.254(3.3) |
| | 3.72 | Example I-34: $^1$H-NMR(400.0 MHz, $d_6$-DMSO): = 9.272(1.8); 9.253(1.9); 8.550(2.6); 8.157(3.0); 7.964(1.7); 7.943(2.1); 7.748(1.7); 7.727(1.4); 7.665(1.5); 7.647(1.5); 4.018(1.1); 3.998(16.0); 3.982(3.2); 3.964(1.0); 3.908(1.6); 3.336(143.8); 2.678(0.6); 2.509(106.9); 2.335(0.6); 1.332(3.2); 1.314(6.8); 1.296(3.1) |
| | 2.98 | Example I-35: $^1$H-NMR(400.0 MHz, $d_6$-DMSO): = 8.867(2.8); 8.121(3.1); 7.941(1.8); 7.919(2.3); 7.910(2.2); 7.887(2.4); 7.721(1.7); 7.700(1.4); 7.639(1.7); 7.636(1.8); 7.616(1.5); 7.613(1.5); 3.954(16.0); 3.918(1.0); 3.908(2.1); 3.900(3.4); 3.881(3.3); 3.863(1.0); 3.336(88.8); 2.678(0.4); 2.513(51.9); 2.509(68.8); 2.505(55.0); 2.454(10.4); 2.336(0.4); 1.305(3.5); 1.287(7.7); 1.268(3.4) |
| | 3.70 | Example I-36: $^1$H-NMR(400.0 MHz, $d_6$-DMSO): = 9.422(3.3); 8.213(2.0); 8.189(2.5); 8.160(3.8); 8.031(2.2); 8.007(1.7); 7.967(2.1); 7.945(2.5); 7.749(2.1); 7.727(1.7); 4.088(1.2); 4.070(3.5); 4.051(3.6); 4.033(1.3); 4.005(16.0); 3.908(2.0); 3.335(209.2); 2.678(0.9); 2.509(145.5); 2.335(0.8); 1.352(3.8); 1.333(7.9); 1.315(3.7) |
| | 3.41 | Example I-37: $^1$H-NMR(400.0 MHz, $d_6$-DMSO): = 8.664(2.3); 8.647(2.3); 8.100(4.9); 7.896(1.9); 7.875(2.2); 7.670(3.2); 7.649(2.6); 7.587(4.0); 7.075(3.0); 7.058(2.9); 4.139(13.9); 3.908(1.9); 3.339(213.0); 3.183(0.4); 3.170(0.4); 3.047(1.7); 3.029(5.0); 3.010(5.0); 2.992(1.8); 2.679(0.8); 2.509(125.8); 2.457(16.0); 2.336(0.7); 1.084(5.8); 1.066(11.7); 1.047(5.7) |
| | 3.57 | Example I-38: $^1$H-NMR(400.0 MHz, $d_6$-DMSO): = 8.578(2.9); 8.102(4.1); 7.898(1.6); 7.877(1.9); 7.733(2.3); 7.710(2.6); 7.672(2.6); 7.651(2.1); 7.410(2.1); 7.387(1.8); 4.142(12.6); 3.908(2.4); 3.342(304.3); 3.061(1.6); 3.042(4.8); 3.024(4.9); 3.006(1.6); 2.679(0.8); 2.675(0.7); 2.514(108.0); 2.510(145.7); 2.505(113.6); 2.436(16.0); 2.336(0.8); 1.095(5.9); 1.077(12.2); 1.058(5.8) |
| 2.29 | 2.30 | Example I-39: $^1$H-NMR(400.0 MHz, $d_6$-DMSO): = 9.343(2.2); 9.325(2.2); 9.290(4.5); 9.279(0.6); 8.322(4.7); 8.306(2.8); 8.287(2.3); 7.605(1.7); 7.587(3.1); 7.569(1.6); 4.105(16.0); 4.083(1.9); 3.982(1.0); 3.963(3.5); 3.945(3.6); 3.926(1.1); 3.875(0.4); 3.857(0.7); 3.792(1.0); 3.774(3.4); 3.755(3.5); 3.737(1.1); 3.319(170.9); 2.675(0.6); 2.671(0.8); 2.667(0.6); 2.506(102.2); 2.502(137.0); 2.497(105.1); 2.333(0.6); 2.329(0.8); 2.324(0.6); 2.073(1.5); 1.353(3.7); 1.335(8.1); 1.316(3.6); 1.299(0.5); 1.281(0.9); 1.262(0.4); 1.211(3.7); |

| LOGP_NEUTRAL | LOGP_HCOOH | NMR |
|---|---|---|
| | | 1.193(8.0); 1.174(3.6); 0.146(0.6); 0.000(115.2); −0.008(5.8); −0.150(0.6) |
| 2.59 | 2.51 | Example I-40: ¹H-NMR(400.0 MHz, d₆-DMSO): = 19.785(0.6); 18.114(0.6); 13.547(5.4); 10.632(1.0); 9.399(0.5); 9.227(4.7); 9.209(5.2); 9.138(0.6); 8.314(1.9); 7.915(4.3); 7.892(5.2); 7.865(0.6); 7.840(0.7); 7.768(11.2); 7.721(2.8); 7.704(3.8); 7.684(2.7); 7.526(11.2); 7.353(0.7); 7.343(2.9); 7.325(4.8); 7.308(2.6); 4.201(2.3); 4.183(7.0); 4.165(7.1); 4.147(2.3); 3.821(0.6); 3.818(0.6); 3.801(0.9); 3.781(0.8); 3.503(0.5); 3.456(0.6); 3.414(0.7); 3.398(0.9); 3.317(812.1); 3.024(0.6); 2.897(0.5); 2.754(0.6); 2.741(0.9); 2.726(0.8); 2.670(8.9); 2.620(1.3); 2.504(1263.4); 2.501(1446.2); 2.328(8.0); 1.294(7.8); 1.275(16.0); 1.257(8.4); 1.235(3.1); 1.192(1.1); 1.175(1.8); 1.155(1.1); 0.856(0.7); 0.146(5.2); 0.117(0.6); 0.003(638.7); 0.000(1099.3); −0.009(118.6); −0.150(5.2); −3.158(0.5) |
| 2.62 | 2.59 | Example I-41: ¹H-NMR(601.6 MHz, CD3CN): = 9.118(0.9); 9.117(1.5); 9.115(0.9); 9.107(0.9); 9.105(1.5); 9.103(0.9); 7.803(0.8); 7.801(1.4); 7.788(1.0); 7.786(1.6); 7.635(0.8); 7.633(0.9); 7.624(0.9); 7.622(1.1); 7.621(0.9); 7.618(0.8); 7.609(0.8); 7.607(0.8); 7.500(3.8); 7.423(4.0); 7.230(0.8); 7.228(0.8); 7.218(1.4); 7.216(1.4); 7.206(0.7); 7.204(0.7); 5.444(1.5); 3.917(16.0); 3.842(1.1); 3.830(3.5); 3.818(3.6); 3.806(1.2); 2.118(25.1); 1.962(0.9); 1.954(2.3); 1.950(3.0); 1.946(15.0); 1.942(25.6); 1.938(37.5); 1.933(25.8); 1.929(13.1); 1.341(0.5); 1.333(3.7); 1.321(7.7); 1.308(3.7); 1.285(0.7); 1.270(0.6); 0.000(4.6) |
| | 3.34 | Example I-42: ¹H-NMR(400.0 MHz, d₆-DMSO): = 9.115(2.6); 9.112(2.6); 8.140(2.7); 8.060(1.9); 8.036(2.4); 7.953(1.6); 7.931(2.0); 7.852(1.7); 7.847(1.6); 7.828(1.4); 7.823(1.3); 7.736(1.5); 7.714(1.2); 4.021(0.9); 4.002(3.1); 3.986(16.0); 3.966(1.0); 3.908(1.9); 3.339(121.9); 2.678(0.5); 2.674(0.4); 2.513(66.4); 2.509(86.8); 2.505(66.0); 2.340(0.4); 2.336(0.5); 2.332(0.4); 1.336(3.1); 1.318(6.9); 1.299(3.1) |
| | 3.60 | Example I-43: ¹H-NMR(601.6 MHz, CD3CN): = 9.287(3.0); 9.275(3.1); 8.453(4.6); 8.281(2.9); 8.267(3.1); 7.809(2.8); 7.793(4.1); 7.792(4.4); 7.777(2.4); 7.775(2.4); 7.633(1.7); 7.632(1.8); 7.622(2.1); 7.620(2.5); 7.619(2.3); 7.617(1.9); 7.607(1.9); 7.605(1.9); 7.222(1.6); 7.220(1.6); 7.211(3.0); 7.209(3.0); 7.199(1.6); 7.197(1.6); 7.174(0.4); 7.162(0.4); 4.042(2.3); 4.030(7.3); 4.017(7.4); 4.005(2.5); 2.334(1.8); 2.260(0.8); 2.049(0.4); 1.962(2.5); 1.954(3.6); 1.950(4.4); 1.946(23.2); 1.942(39.6); 1.938(57.2); 1.934(40.2); 1.930(21.6); 1.823(0.3); 1.384(7.7); 1.372(16.0); 1.360(7.8); 1.336(0.7); 1.325(0.9); 1.313(0.8); 1.302(0.6); 0.000(1.8) |
| 2.52 | 2.53 | Example I-44: ¹H-NMR(400.0 MHz, d₆-DMSO): = 9.146(3.9); 9.128(4.0); 8.979(6.3); 8.966(5.9); 8.313(0.8); 8.032(3.5); 8.009(4.3); 7.799(2.2); 7.782(2.7); 7.779(2.7); 7.759(2.0); 7.756(1.7); 7.438(2.2); 7.421(3.9); 7.418(3.4); 7.403(2.0); 7.400(1.6); 3.955(2.1); 3.937(6.9); 3.919(7.1); 3.900(2.3); 3.318(421.3); 2.676(1.9); 2.671(2.4); 2.667(1.7); 2.524(6.2); 2.510(173.6); 2.506(318.7); 2.502(395.9); 2.498(276.1); 2.333(1.9); 2.329(2.3); 2.324(1.6); 1.352(7.3); 1.333(16.0); 1.315(7.1); 0.147(1.0); 0.000(229.7); −0.008(7.4); −0.149(1.0) |
| 3.22 | 3.20 | Example I-45: ¹H-NMR(400.0 MHz, d₆-DMSO): = 9.212(3.8); 8.587(2.3); 8.314(0.5); 8.249(4.1); 7.750(1.9); 7.727(2.1); 7.430(1.5); 7.426(1.5); 7.407(1.3); 7.403(1.4); 6.837(0.4); 4.276(16.0); 3.316(184.0); 3.058(1.3); 3.040(3.9); 3.022(4.0); 3.003(1.3); 2.811(0.5); 2.798(0.5); 2.675(1.2); 2.671(1.6); 2.666(1.2); 2.524(3.4); 2.510(94.0); 2.506(199.6); 2.501(280.0); 2.497(209.5); 2.434(9.2); 2.366(0.9); 2.333(1.3); 2.328(1.7); 2.324(1.3); 1.458(0.3); 1.138(0.3); 1.128(0.3); 1.091(4.2); 1.072(8.9); 1.054(4.1); 0.146(0.9); 0.008(6.1); 0.000(194.1); −0.008(6.6); −0.150(0.9) |
| | 2.73 | Example I-46: ¹H-NMR(400.0 MHz, d₆-DMSO): = 8.092(3.0); 7.924(1.8); 7.902(2.2); 7.861(1.5); 7.839(2.0); 7.733(1.5); 7.715(1.9); 7.707(2.0); 7.693(1.4); 7.685(1.5); 7.273(1.7); 7.256(1.6); 3.909(2.2); 3.836(16.0); 3.824(3.7); 3.805(3.4); 3.787(1.1); 3.335(97.7); 3.051(11.2); 2.678(0.7); 2.674(0.5); 2.513(82.6); 2.509(109.3); 2.505(84.8); 2.336(0.6); 1.347(3.7); 1.329(8.1); 1.310(3.6) |
| | 3.51 | Example I-47: ¹H-NMR(400.0 MHz, d₆-DMSO): = 9.494(5.8); 9.018(6.4); 8.990(6.3); 8.253(3.6); 8.229(4.6); 8.061(3.8); 8.037(3.0); 4.069(2.2); 4.051(7.0); 4.033(7.1); 4.014(2.2); 3.909(4.4); 3.330(268.6); 2.678(1.9); 2.509(326.6); 2.336(1.8); 1.401(7.4); 1.382(16.0); 1.364(7.3); 1.241(0.4); 0.006(0.5) |
| 2.36 | 2.43 | Example I-48: ¹H-NMR(400.0 MHz, d₆-DMSO): = 9.267(3.9); 8.849(2.4); 8.284(4.1); 7.922(1.9); 7.899(2.2); 7.654(1.6); 7.651(1.6); 7.631(1.4); 7.628(1.4); 4.056(16.0); 3.876(1.0); 3.857(3.3); 3.839(3.3); 3.820(1.0); 3.319(146.9); 2.675(0.5); 2.671(0.7); 2.666(0.5); 2.524(1.6); 2.511(37.9); 2.506(78.9); 2.502(109.4); 2.497(81.1); 2.493(38.6); 2.456(9.2); 2.333(0.5); 2.329(0.6); 2.324(0.5); 2.073(0.6); 1.296(3.5); 1.277(7.7); 1.259(3.4); 0.146(0.3); 0.008(2.6); 0.000(79.4); −0.008(2.6); −0.150(0.4) |
| | 3.53 | Example I-49: ¹H-NMR(400.0 MHz, d₆-DMSO): = 9.325(4.0); 9.307(4.1); 9.011(6.1); 8.987(6.2); 8.605(5.7); 7.694(3.5); 7.690(3.0); 7.675(3.4); 7.671(2.9); 4.013(2.1); 3.995(6.9); 3.976(6.9); 3.958(2.2); 3.908(4.2); 3.335(266.7); 3.181(0.7); 3.168(0.7); 2.678(1.3); 2.509(217.7); 2.505(163.4); 2.335(1.2); 1.552(0.3); 1.534(0.4); 1.372(7.4); 1.354(16.0); 1.336(7.2); 1.255(0.4); 1.240(0.5); 0.005(0.3) |
| 4.14 | | Example I-50: ¹H-NMR(400.0 MHz, d₆-DMSO): = 8.965(3.7); 8.947(3.8); 8.909(6.6); 8.898(6.5); 8.388(5.4); 7.483(3.2); 7.465(3.1); 3.908(3.9); 3.338(306.5); 3.265(0.4); 3.182(0.7); 3.169(0.6); 3.122(2.4); 3.104(7.4); 3.085(7.6); 3.067(2.5); 2.678(1.1); 2.509(193.4); 2.337(1.0); 1.238(0.4); 1.150(7.9); 1.131(16.0); 1.113(7.6) |
| 3.20 | 3.21 | Example I-51: ¹H-NMR(400.0 MHz, d₆-DMSO): = 9.245(4.1); 9.227(4.2); 9.122(5.6); 9.057(5.6); 8.313(1.1); 8.012(3.6); 7.989(4.4); 7.763(2.5); 7.746(2.9); 7.723(2.2); 7.396(2.4); 7.378(4.2); 7.361(2.9); 4.112(2.2); 4.093(7.2); 4.075(7.3); 4.056(2.3); 3.315(247.1); 2.670(3.5); 2.505(396.4); 2.501(565.6); 2.497(456.3); 2.328(3.2); 1.356(7.3); 1.337(16.0); 1.319(7.3); 1.257(0.3); 1.235(1.8); 0.146(2.2); 0.008(15.5); 0.000(443.8); −0.008(20.1); −0.150(2.0) |

| LOGP_NEUTRAL | LOGP_HCOOH | NMR |
|---|---|---|
| 3.39 | 3.43 | Example I-52: $^1$H-NMR(400.0 MHz, d$_6$-DMSO): = 8.821(2.9); 8.803(2.0); 8.786(2.0); 8.619(3.0); 7.840(1.9); 7.818(2.2); 7.569(1.1); 7.550(1.4); 7.530(1.1); 7.251(1.2); 7.234(2.2); 7.217(1.1); 4.359(0.6); 4.341(0.6); 4.198(16.0); 3.318(102.7); 3.085(1.3); 3.066(4.0); 3.048(4.0); 3.030(1.3); 2.671(1.1); 2.501(185.6); 2.328(1.1); 1.397(0.8); 1.359(0.6); 1.341(1.1); 1.323(0.6); 1.100(4.1); 1.081(8.3); 1.063(3.9); 0.000(40.5) |
| 2.78 | 2.84 | Example I-53: $^1$H-NMR(400.0 MHz, d$_6$-DMSO): = 8.881(2.3); 8.877(2.4); 8.865(2.4); 8.662(2.4); 8.658(2.3); 8.314(0.3); 7.925(1.9); 7.902(2.2); 7.651(1.6); 7.648(1.6); 7.628(1.3); 7.625(1.4); 4.162(0.5); 3.963(16.0); 3.905(0.9); 3.886(3.2); 3.868(3.3); 3.850(1.0); 3.315(38.6); 2.675(0.7); 2.671(1.0); 2.666(0.7); 2.524(2.7); 2.510(55.9); 2.506(115.0); 2.501(159.0); 2.497(119.6); 2.493(58.6); 2.455(9.0); 2.333(0.7); 2.328(0.9); 2.324(0.7); 2.073(0.7); 1.305(3.4); 1.287(7.6); 1.269(3.3); 0.008(1.5); 0.000(40.8); −0.008(1.6) |
| 2.37 | 2.41 | Example I-54: $^1$H-NMR(400.0 MHz, d$_6$-DMSO): = 9.265(3.8); 8.582(2.4); 8.576(2.4); 8.314(0.5); 8.283(4.1); 7.948(2.3); 7.923(2.6); 7.587(1.9); 7.581(1.9); 7.563(1.6); 7.557(1.7); 4.425(0.4); 4.069(16.0); 3.917(16.0); 3.903(3.4); 3.885(3.2); 3.866(1.3); 3.315(56.6); 2.675(0.9); 2.670(1.3); 2.666(1.0); 2.524(3.5); 2.510(71.9); 2.506(152.7); 2.501(215.5); 2.497(165.6); 2.492(83.1); 2.333(0.9); 2.328(1.2); 2.324(1.0); 1.988(0.3); 1.308(3.3); 1.290(7.7); 1.271(3.3); 0.008(2.2); 0.000(65.1); −0.008(2.7) |
| 2.48 | 2.54 | Example I-55: $^1$H-NMR(400.0 MHz, d$_6$-DMSO): = 9.575(0.4); 9.235(4.7); 9.145(0.6); 8.869(2.7); 8.863(2.7); 8.607(0.6); 8.314(1.4); 8.222(5.0); 8.183(0.7); 7.888(2.7); 7.863(3.0); 7.454(1.7); 7.448(1.7); 7.429(1.6); 7.423(1.6); 4.425(16.0); 4.070(0.8); 4.018(2.3); 3.917(1.2); 3.901(0.9); 3.867(15.8); 3.848(0.4); 3.804(0.8); 3.736(0.5); 3.718(1.0); 3.699(1.0); 3.685(1.5); 3.666(1.3); 3.648(0.6); 3.565(0.5); 3.547(1.3); 3.528(1.6); 3.513(0.9); 3.495(1.5); 3.487(0.5); 3.476(0.6); 3.380(0.5); 3.317(383.6); 2.890(0.4); 2.743(0.4); 2.671(5.4); 2.655(0.7); 2.650(0.6); 2.630(1.1); 2.574(1.0); 2.556(1.3); 2.505(702.5); 2.501(918.0); 2.498(711.7); 2.409(0.4); 2.347(0.6); 2.328(5.4); 1.395(3.9); 1.376(8.1); 1.358(3.8); 1.236(0.9); 1.179(0.6); 1.161(0.6); 0.147(1.2); 0.000(216.8); −0.149(1.1) |
|  | 2.89 | Example I-56: $^1$H-NMR(400.0 MHz, d$_6$-DMSO): = 8.974(5.0); 8.963(4.7); 8.918(4.2); 7.952(3.0); 7.929(3.6); 7.674(2.7); 7.651(2.3); 3.940(1.6); 3.922(5.1); 3.909(5.5); 3.903(5.4); 3.885(1.6); 3.338(380.9); 3.182(0.7); 3.169(0.6); 2.678(1.3); 2.575(0.4); 2.513(165.9); 2.509(212.8); 2.456(16.0); 2.336(1.2); 1.360(5.5); 1.342(11.9); 1.324(5.4); 1.306(0.4); 1.265(0.5); 1.241(1.3); 0.860(0.3); 0.006(0.3) |
|  | 4.11 | Example I-57: $^1$H-NMR(400.0 MHz, d$_6$-DMSO): = 8.930(6.0); 8.907(6.1); 8.206(0.5); 8.192(3.5); 8.170(3.7); 7.942(0.4); 7.924(0.5); 7.906(3.4); 7.888(3.9); 7.675(2.3); 7.654(2.8); 7.635(2.1); 3.908(3.3); 3.333(211.2); 3.078(2.1); 3.059(6.5); 3.041(6.5); 3.022(2.2); 2.682(0.8); 2.678(1.1); 2.674(0.8); 2.513(137.8); 2.509(182.9); 2.505(141.8); 2.340(0.8); 2.336(1.0); 2.331(0.8); 1.236(0.3); 1.119(7.8); 1.101(16.0); 1.082(7.5) |
|  | 4.14 | Example I-58: $^1$H-NMR(400.0 MHz, d$_6$-DMSO): = 9.064(4.4); 8.912(5.9); 8.902(5.5); 8.062(2.9); 8.038(3.6); 7.827(2.9); 7.823(2.9); 7.803(2.4); 7.799(2.4); 3.908(5.5); 3.516(0.4); 3.337(425.1); 3.132(2.3); 3.113(7.4); 3.095(7.6); 3.077(2.4); 2.683(1.3); 2.678(1.6); 2.513(198.0); 2.509(266.5); 2.505(205.0); 2.340(1.0); 2.336(1.4); 2.331(1.0); 1.304(0.5); 1.265(0.6); 1.240(1.5); 1.165(7.8); 1.146(16.0); 1.128(7.4); 0.859(0.3); 0.006(0.4) |
| 2.49 | 2.58 | Example I-59: $^1$H-NMR(400.0 MHz, d$_6$-DMSO): = 9.100(1.9); 9.082(2.0); 8.889(2.5); 8.886(2.6); 8.674(2.7); 8.671(2.5); 8.012(1.8); 7.990(2.1); 7.782(1.1); 7.765(1.3); 7.745(0.9); 7.742(0.9); 7.420(1.0); 7.403(1.9); 7.385(0.9); 3.990(16.0); 3.936(1.0); 3.918(3.4); 3.900(3.5); 3.881(1.1); 3.319(47.0); 2.672(0.4); 2.507(42.5); 2.502(57.4); 2.498(44.2); 2.329(0.3); 1.989(0.4); 1.309(3.6); 1.291(7.8); 1.273(3.5); 1.203(0.4); 1.195(0.4); 1.176(0.3) |
| 3.15 | 3.20 | Example I-60: $^1$H-NMR(400.0 MHz, d$_6$-DMSO): = 8.867(13.5); 8.782(3.2); 8.765(3.4); 8.313(2.5); 7.839(3.1); 7.816(3.6); 7.587(1.7); 7.573(1.9); 7.570(2.1); 7.564(1.6); 7.550(1.7); 7.281(0.4); 7.259(2.1); 7.244(3.3); 7.227(1.7); 3.468(0.3); 3.410(0.4); 3.317(1058.9); 3.264(0.4); 3.066(2.4); 3.047(7.5); 3.029(7.5); 3.011(2.6); 2.994(0.4); 2.891(0.6); 2.741(0.3); 2.731(0.5); 2.675(4.3); 2.670(6.0); 2.666(4.6); 2.630(0.4); 2.595(0.5); 2.524(13.5); 2.510(349.7); 2.506(739.6); 2.501(1036.0); 2.497(768.9); 2.492(365.6); 2.434(0.4); 2.332(4.4); 2.328(5.9); 2.324(4.3); 1.652(0.4); 1.127(7.6); 1.109(16.0); 1.091(7.4); 0.146(5.1); 0.008(34.4); 0.000(1123.6); −0.008(38.9); −0.066(0.4); −0.076(0.3); −0.150(5.2); −3.059(0.3) |

Use Examples

*Ctenocephalides felis*—In Vitro Contact Tests with Adult Cat Fleas

For the coating of the test tubes, 9 mg of active compound are first dissolved in 1 ml of acetone p.a. and then diluted to the desired concentration with acetone p.a. 250 µl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 cm$^2$, given homogeneous distribution, an area-based dose of 5 µg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the test tubes are stood upright and the fleas are knocked to the base of the tube. Fleas which remain motionless at the base or move in an uncoordinated manner are considered to be dead or moribund.

A substance shows good efficacy against *Ctenocephalides felis* if at least 80% efficacy was achieved in this test at an application rate of 5 µg/cm$^2$. 100% efficacy means that all the fleas were dead or moribund. 0% efficacy means that no fleas were harmed.

In this test, for example, the following compounds from the preparation examples show an efficacy of 100% at an application rate of 5 µg/cm² (=500 g/ha): I-1, I-4, I-6, I-17, I-18, I-23, I-33, I-34, I-35, I-59

*Rhipicephalus sanguineus*—In Vitro Contact Tests with Adult Brown Dog Ticks

For the coating of the test tubes, 9 mg of active compound are first dissolved in 1 ml of acetone p.a. and 20 then diluted to the desired concentration with acetone p.a. 250 µl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 cm², given homogeneous distribution, an area-based dose of 5 µg/cm² is achieved.

After the solvent has evaporated off, the tubes are populated with 5-10 adult dog ticks (*Rhipicephalus sanguineus*), sealed with a perforated plastic lid and incubated in a horizontal position in the dark at room temperature and ambient humidity. After 48 h, efficacy is determined. To this end, the ticks are knocked to the base of the tube and incubated on a hotplate at 45-50° C. for not more than 5 min. Ticks which remain motionless on the base or move in such an uncoordinated manner that they are unable to deliberately avoid the heat by climbing upwards are considered to be dead or moribund.

A substance shows good activity against *Rhipicephalus sanguineus* if, in this test, an efficacy of at least 80% was achieved at an application rate of 5 µg/cm². An efficacy of 100% means that all the ticks were dead or moribund. 0% efficacy means that none of the ticks were harmed.

In this test, for example, the following compounds from the preparation examples show an efficacy of 100% at an application rate of 5 µg/cm²: (=500 g/ha): I-59

In this test, for example, the following compounds from the preparation examples show an efficacy of 80% at an application rate of 5 µg/cm² (=500 g/ha): I-35

*Boophilus microplus*—Injection Test
Solvent: dimethyl sulphoxide

To produce a suitable preparation of active compound, 10 mg of active compound are mixed with 0.5 ml of solvent and the concentrate is diluted with solvent to the desired concentration.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compounds from the preparation examples show an efficacy of 95% at an application rate of 20 µg/animal: 1-18

*Ctenocephalides felis*—Oral Test
Solvent: dimethyl sulphoxide

To produce a suitable preparation of active compound, 10 mg of active compound are mixed with 0.5 ml of dimethyl sulphoxide. Dilution with citrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed onto the chamber. The cylinder contains the blood/active compound preparation, which can be imbibed by the fleas through the parafilm membrane.

After 2 days, the kill in % is determined. 100% means that all of the fleas have been killed; 0% means that none of the fleas have been killed.

In this test, for example, the following compounds from the preparation examples show an efficacy of 100% at an application rate of 100 ppm: I-6, I-17, I-18

In this test, for example, the following compounds from the preparation examples show an efficacy of 98% at an application rate of 100 ppm: I-1

In this test, for example, the following compounds from the preparation examples show an efficacy of 90% at an application rate of 100 ppm: I-4

In this test, for example, the following compounds from the preparation examples show an efficacy of 80% at an application rate of 100 ppm: I-59

*Haemonchus contortus* Test
Solvent: Dimethyl Sulphoxide

To produce a suitable preparation of active compound, 10 mg of active compound are mixed with 0.5 ml of dimethyl sulphoxide and the concentrate is diluted with "Ringer's solution" to the desired concentration.

Vessels containing the active compound preparation of the desired concentration are populated with about 40 larvae of the red stomach worm (*Haemonchus contortus*).

After 5 days, the kill in % is determined. 100% means that all the larvae have been killed; 0% means that none of the larvae have been killed.

In this test, for example, the following compounds from the preparation examples show an efficacy of 80% at an application rate of 20 ppm: I-59

*Lucilia cuprina* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

About 20 L1 larvae of the Australian sheep blowfly (*Lucilia cuprina*) are transferred into a test vessel containing minced horsemeat and the active compound preparation of the desired concentration.

After 2 days, the kill in % is determined. 100% means that all the larvae have been killed; 0% means that no larvae have been killed.

In this test, for example, the following compounds from the preparation examples show an efficacy of 100% at an application rate of 100 ppm: I-1, I-4, I-6, I-10, I-17, I-18, I-59

*Musca domestica* Test
Solvent: dimethyl sulphoxide

To produce a suitable preparation of active compound, 10 mg of active compound are mixed with 0.5 ml of dimethyl sulphoxide, and the concentrate is diluted with water to the desired concentration.

Vessels containing a sponge treated with sugar solution and the active compound preparation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples show an efficacy of 90% at an application rate of 20 ppm: I-6

In this test, for example, the following compounds from the preparation examples show an efficacy of 80% at an application rate of 20 ppm: I-59

In this test, for example, the following compounds from the preparation examples show an efficacy of 95% at an application rate of 4 ppm: I-18

In this test, for example, the following compounds from the preparation examples show an efficacy of 85% at an application rate of 4 ppm: I-1

In this test, for example, the following compounds from the preparation examples show an efficacy of 80% at an application rate of 4 ppm: I-4, I-17

*Meloidogyne incognita* Test
Solvent: 125.0 parts by weight of acetone

To produce a suitable preparation of active compound, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples show an efficacy of 100% at an application rate of 20 ppm: I-52

*Myzus persicae*—Spray Test
Solvent: 78 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active compound preparation of the desired concentration.

After 5-6 days, the efficacy in % is determined. 100% means that all the aphids have been killed; 0% means that no aphids have been killed.

In this test, for example, the following compounds from the preparation examples show an efficacy of 100% at an application rate of 500 g/ha: I-17, I-21, I-53

In this test, for example, the following compounds from the preparation examples show an efficacy of 90% at an application rate of 500 g/ha: I-1, I-2, I-4, I-6, I-7, I-11, I-19, I-22, I-35, I-41, I-46, I-48, I-54, I-59

*Phaedon cochleariae*—Spray Test
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 100% at an application rate of 500 g/ha: I-6, I-8, I-9, I-10, I-11, I-13, I-16, I-17, I-18, I-19, I-21, I-22, I-23, I-24, I-25, I-29, I-34, I-36, I-39, I-40, I-41, I-42, I-44, I-47, I-49, I-50, I-52, I-59

In this test, for example, the following compounds from the preparation examples show an efficacy of 83% at an application rate of 500 g/ha: I-1, I-12, I-26, I-30, I-46

In this test, for example, the following compounds from the preparation examples show an efficacy of 83% at an application rate of 100 g/ha: I-43

*Spodoptera frugiperda*—Spray Test
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Leaf discs of maize (*Zea mays*) are sprayed with an active compound preparation of the desired concentration and, after drying, populated with caterpillars of the armyworm (*Spodoptera frugiperda*).

After 7 days, the efficacy in % is determined. 100% means that all the caterpillars have been killed; 0% means that no caterpillars have been killed.

In this test, for example, the following compounds from the preparation examples show an efficacy of 100% at an application rate of 500 g/ha: I-1, I-3, I-4, I-5, I-6, I-7, I-8, I-10, I-11, I-13, I-16, I-17, I-18, I-19, I-21, I-23, I-24, I-25, I-28, I-29, I-30, I-34, I-35, I-36, I-39, I-42, I-48, I-49, I-50, I-53, I-54, I-59

In this test, for example, the following compounds from the preparation examples show an efficacy of 83% at an application rate of 500 g/ha: I-12, I-33, I-41, I-44, I-47

*Tetranychus urticae*—Spray Test, OP-Resistant
Solvent: 78.0 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of bean leaves (*Phaseolus vulgaris*) infested with all stages of the greenhouse red spider mite (*Tetranychus urticae*) are sprayed with an active compound preparation of the desired concentration.

After 6 days, the efficacy in % is determined. 100% means that all the spider mites have been killed; 0% means that no spider mites have been killed.

In this test, for example, the following compounds from the preparation examples show an efficacy of 90% at an application rate of 500 g/ha: I-59

*Myzus persicae* Spray Test
Solvent: 14 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bell pepper plants (*Capsicum annuum*) severely infested with the green peach aphid (*Myzus persicae*) are treated by spraying with the active compound preparation in the desired concentration.

After 6 days, the kill in % is determined. 100% means that all of the aphids have been killed; 0% means that none of the aphids have been killed.

In this test, for example, the following compounds from the preparation examples show an efficacy of 100% at an application rate of 100 ppm: I-10

The invention claimed is:
1. A compound of formula (I)

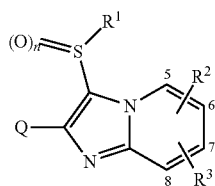

wherein
$R^1$ is ethyl,
$R^3$ is hydrogen,
Q is

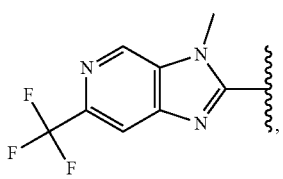 [SMILES: *c1nc2cc(C(F)(F)F)ncc2n1C]

where the bond from Q to the remainder of the molecule is identified by a wavy line,
n is 0, and
$R^2$ is selected from the group consisting of H, 8-CF$_3$, 8-Cl, 8-SC$_2$H$_5$, 5-CF$_3$ and 6-CH$_3$;
or
$R^1$ is ethyl,
$R^3$ is hydrogen,
Q is

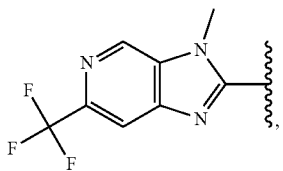

where the bond from Q to the remainder of the molecule is identified by a wavy line, n is 1, and
$R^2$ is selected from the group consisting of 6-Cl, 6-CF$_3$, 7-CF$_3$, 5-CF$_3$, 8-CF$_3$ and 6-OCH$_3$;
or
$R^1$ is ethyl,
$R^3$ is hydrogen,
Q is

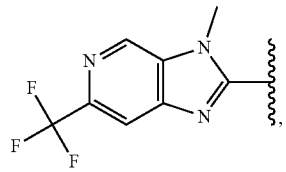 [SMILES: *c1nc2cc(C(F)(F)F)ncc2n1C]

where the bond from Q to the remainder of the molecule is identified by a wavy line,
n is 2, and
$R^2$ is selected from the group consisting of H, 8-Cl, 5-CF$_3$, 8-CF$_3$, 8-SO$_2$C$_2$H$_5$, 6-CH$_3$ and 6-OCH$_3$;
or
$R^1$ is ethyl,
$R^3$ is hydrogen,
Q is

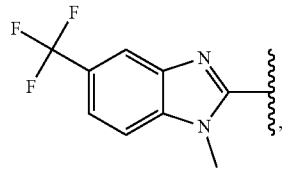 [SMILES: *c1nc2cc(C(F)(F)F)ccc2n1C]

where the bond from Q to the remainder of the molecule is identified by a wavy line,
n is 0, and
$R^2$ is selected from the group consisting of H, 5-CH$_3$, 5-CF$_3$, 6-CF$_3$, 6-Cl, 7-CF$_3$, 5-SC$_2$H$_5$, 7-SC$_2$H$_5$, 7-CH$_3$ and 6-CH$_3$;
or
$R^1$ is ethyl,
$R^3$ is hydrogen,
Q is

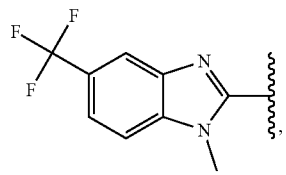 [SMILES: *c1nc2cc(C(F)(F)F)ccc2n1C]

where the bond from Q to the remainder of the molecule is identified by a wavy line,
n is 1, and
$R^2$ is hydrogen;
or
$R^1$ is ethyl,
$R^3$ is hydrogen, Q is

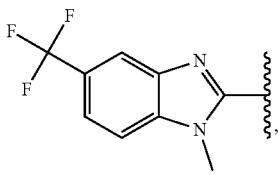

where the bond from Q to the remainder of the molecule is identified by a wavy line, n is 2, and R² is selected from the group consisting of H, 7-CH₃, 7-CF₃, 6-CH₃, 6-CF₃, 6-Cl and 5-CH₃;

or

R¹ is ethyl,

R³ is hydrogen,

Q is

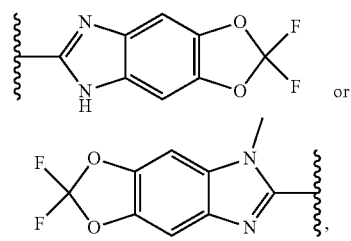

or where the bond from Q to the remainder of the molecule is identified by a wavy line, n is 2, and R² is H.

2. The compound formula (I) according to claim 1, wherein

R¹ is ethyl,

R³ is hydrogen,

Q is

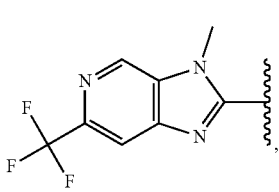

where the bond from Q to the remainder of the molecule is identified by a wavy line, n is 0, and R² is selected from the group consisting of H, 8-CF₃, 8-Cl, 8-SC₂H₅, 5-CF₃ and 6-CH₃.

3. The compound formula (I) according to claim 1, wherein

R¹ is ethyl,

R³ is hydrogen,

Q is

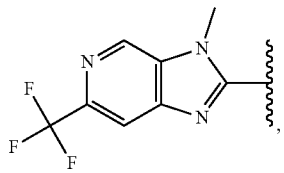 [SMILES: *c1nc2cc(C(F)(F)F)ncc2n1C]

where the bond from Q to the remainder of the molecule is identified by a wavy line, n is 1, and R² is selected from the group consisting of 6-Cl, 6-CF₃, 7-CF₃, 5-CF₃, 8-CF₃ and 6-OCH3.

4. The compound formula (I) according to claim 1, wherein

R¹ is ethyl,

R³ is hydrogen,

Q is

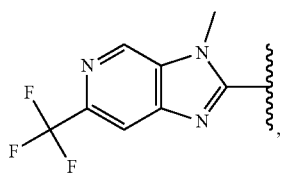 [SMILES: *c1nc2cc(C(F)(F)F)ncc2n1C]

where the bond from Q to the remainder of the molecule is identified by a wavy line, n is 2, and R² is selected from the group consisting of H, 8-Cl, 5-CF₃, 8-CF₃, 8-SO₂C₂H₅, 6-CH₃ and 6-OCH₃.

5. The compound formula (I) according to claim 1, wherein

R¹ is ethyl,

R³ is hydrogen,

Q is

where the bond from Q to the remainder of the molecule is identified by a wavy line, n is 0, and R² is selected from the group consisting of H, 5-CH₃, 5-CF₃, 6-CF₃, 6-Cl, 7-CF₃, 5-SC₂H₅, 7-SC₂H₅, 7-CH₃ and 6-CH₃.

6. The compound formula (I) according to claim 1, wherein

R¹ is ethyl,

R³ is hydrogen,

Q is

where the bond from Q to the remainder of the molecule is identified by a wavy line,
n is 1, and
$R^2$ is hydrogen.

7. The compound formula (I) according to claim 1, wherein
$R^1$ is ethyl,
$R^3$ is hydrogen,
Q is

where the bond from Q to the remainder of the molecule is identified by a wavy line,
n is 2, and
$R^2$ is selected from the group consisting of H, 7-$CH_3$, 7-$CF_3$, 6-$CH_3$, 6-$CF_3$, 6-Cl and 5-$CH_3$.

8. The compound formula (I) according to claim 1, wherein
$R^1$ is ethyl,
$R^3$ is hydrogen,
Q is

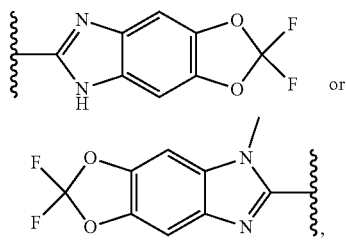

where the bond from Q to the remainder of the molecule is identified by a wavy line,
n is 2, and
$R^2$ is H.

9. The compound formula (I) according to claim 4, wherein
$R^2$ is hydrogen.

10. A method for controlling one or more animal pests, comprising allowing a compound of the formula (I) according to claim 1 or an agrochemical formulation thereof to act on the animal pests and/or a habitat thereof.

11. An agrochemical formulation comprising one or more compounds according to claim 1 and also one or more extenders and/or surfactants.

12. The agrochemical formulation according to claim 11, additionally comprising a further agrochemically active compound.

13. The method according to claim 10, wherein said one or more animal pests comprise insects, arachnids, helminths, nematodes or molluscs.

14. A product comprising a compound of the formula (I) according to claim 1 or an agrochemical formulation thereof for controlling one or more animal pests.

* * * * *